(12) United States Patent
Kaneko et al.

(10) Patent No.: US 8,232,287 B2
(45) Date of Patent: Jul. 31, 2012

(54) PYRIMIDYL INDOLINE COMPOUND

(75) Inventors: Toshio Kaneko, Tokyo (JP); Takeshi Shida, Tokyo (JP); Takayuki Baba, Tokyo (JP); Koji Matsumoto, Tokyo (JP); Kazumasa Aoki, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 22 days.

(21) Appl. No.: 12/738,200

(22) PCT Filed: Oct. 15, 2008

(86) PCT No.: PCT/JP2008/068607
§ 371 (c)(1),
(2), (4) Date: Jul. 23, 2010

(87) PCT Pub. No.: WO2009/051119
PCT Pub. Date: Apr. 23, 2009

(65) Prior Publication Data
US 2010/0292259 A1    Nov. 18, 2010

(30) Foreign Application Priority Data

Oct. 16, 2007 (JP) ................................. 2007-268937

(51) Int. Cl.
*A01N 43/54* (2006.01)
(52) U.S. Cl. ........................ 514/269; 544/319
(58) Field of Classification Search .................. 514/269; 544/319
See application file for complete search history.

(56) References Cited

U.S. PATENT DOCUMENTS

| | | | |
|---|---|---|---|
| 5,866,589 A * | 2/1999 | Romero et al. | ............... 514/318 |
| 7,101,869 B2 | 9/2006 | Blumenkopf et al. | |
| 7,335,657 B2 * | 2/2008 | Cirillo et al. | ................. 514/249 |
| 7,470,699 B2 | 12/2008 | Jones et al. | |
| 2006/0155128 A1 | 7/2006 | Jones et al. | |
| 2007/0021405 A1 | 1/2007 | Abouabdellah | |
| 2007/0078150 A1 | 4/2007 | Jones et al. | |
| 2007/0155763 A1 | 7/2007 | Jones et al. | |
| 2007/0167473 A1 | 7/2007 | Jones et al. | |
| 2009/0318477 A1 * | 12/2009 | Katamreddy | ............... 514/265.1 |
| 2010/0063081 A1 | 3/2010 | Bradly et al. | |

FOREIGN PATENT DOCUMENTS

| | | |
|---|---|---|
| EA | 8148 | 4/2007 |
| EP | 1 529 043 | 5/2005 |
| EP | 1 242 403 B1 | 1/2006 |
| EP | 1 644 357 B1 | 12/2007 |
| EP | 1 911 756 A2 | 4/2008 |
| EP | 1 923 390 A1 | 5/2008 |
| EP | 1 756 084 B1 | 11/2008 |
| JP | 2003-515602 A | 5/2003 |
| RU | 2376305 | 4/2008 |
| WO | WO 01/40215 A1 | 6/2001 |
| WO | WO 2005/007647 A1 | 1/2005 |
| WO | WO 2005/121121 A2 | 12/2005 |
| WO | WO 2006/083491 A2 | 8/2006 |
| WO | WO 2007/003962 | 1/2007 |

OTHER PUBLICATIONS

International Search Report for International Application No. PCT/JP2008/068607, mailed on Nov. 18, 2008 (English & Japanese).
English translation of the Decision to Grant issued by the Patent Office of the Russian Federation on Apr. 23, 2012.

* cited by examiner

*Primary Examiner* — James O Wilson
*Assistant Examiner* — Alexander R Pagano
(74) *Attorney, Agent, or Firm* — Locke Lord LLP

(57) ABSTRACT

It is intended to provide a pyrimidyl indoline compound which structurally differs from compounds used as active ingredients in conventional oral hypoglycemic agents and has excellent hypoglycemic effect. The present invention provides a compound represented by the general formula (I) or a pharmaceutically acceptable salt thereof:

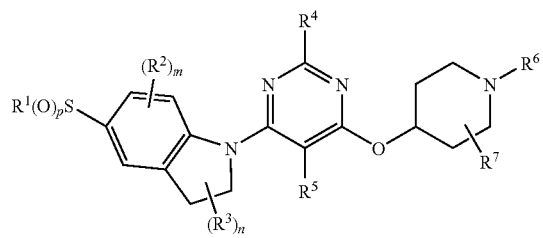

(I)

24 Claims, No Drawings

PYRIMIDYL INDOLINE COMPOUND

This application is a national phase entry under 35 USC §371 of International Application Number PCT/JP2008/068607, filed on Oct. 15, 2008, entitled "PYRIMIDYL INDOLINE COMPOUND", which claims the benefit of Japanese Patent Application Number 2007-268937, filed on Oct. 16, 2007, all of which are hereby incorporated by reference.

FIELD OF THE INVENTION

The present invention relates to a novel pyrimidyl indoline compound having a hypoglycemic effect or a pharmaceutically acceptable salt thereof, and to a pharmaceutical composition comprising the compound or pharmaceutically acceptable salt thereof as an active ingredient.

BACKGROUND OF THE INVENTION

Diabetes mellitus is a metabolic disease mainly characterized by a chronic hyperglycemic state caused by a shortage of insulin action. For treating diabetes mellitus, drug therapy is generally practiced together with diet and exercise therapies. For example, a biguanide or thiazolidinedione agent which improves insulin resistance, a sulfonylurea or glinide agent which promotes insulin secretion from pancreatic β cells, or an α-glucosidase inhibitor which inhibits sugar absorption is used as an oral hypoglycemic agent, a type of therapeutic drug for diabetes mellitus.

However, these agents have been reported to have side effects such as: lactic acidosis (biguanide agent); weight gain and edema (thiazolidinedione agent); hypoglycemia and secondary failure due to long-term use (sulfonylurea and glinide agents); and diarrhea α-glucosidase inhibitor). Thus, there is a need to develop an oral hypoglycemic agent that can solve such problems.

Moreover, pyrimidine compounds, piperidine-1-carboxylate compounds, and the like have also been developed in recent years as oral hypoglycemic agents having a novel structure (see e.g., Patent Documents 1 to 4).

Patent Document 1: Pamphlet of International Publication No. WO 05/7647
Patent Document 2: Pamphlet of International Publication No. WO 05/121121
Patent Document 3: U.S. Patent Application No. 2007/167473
Patent Document 4: Pamphlet of International Publication No. WO 07/3962

SUMMARY OF THE INVENTION

Problems to be Solved by the Invention

Thus, an object of the present invention is to provide a pyrimidyl indoline compound which structurally differs from compounds used as active ingredients in conventional oral hypoglycemic agents and which has an excellent hypoglycemic effect, or a pharmaceutically acceptable salt thereof, and to provide a pharmaceutical composition having excellent therapeutic and/or preventive effects on type 1 diabetes mellitus, type 2 diabetes mellitus, pregnancy diabetes, hyperglycemia caused by other factors, impaired glucose tolerance (IGT), diabetes-related disease (e.g., adiposity, hyperlipemia, hypercholesterolemia, lipid metabolism abnormality, hypertension, fatty liver, metabolic syndrome, edema, cardiac failure, angina pectoris, myocardial infarction, arteriosclerosis, hyperuricemia, and gout), or complications from diabetes (e.g., retinopathy, nephropathy, neuropathy, cataract, foot gangrene, infectious disease, and ketosis).

Means for Solving the Problems

The present invention provides
(1) a compound represented by the general formula (I) or a pharmaceutically acceptable salt thereof:

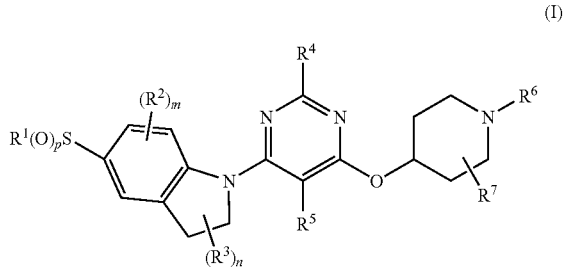

(I)

wherein
p is 1 or 2;
$R^1$ is a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an amino group, or a mono- or di(C1-C6 alkyl)amino group;

substituent group α is the group consisting of a halogen atom, a hydroxyl group, a C1-C6 alkoxy group, a C3-C7 cycloalkyl group which may have 1 to 3 substituents selected from substituent group β, an amino group, a mono- or di(C1-C6 alkyl)amino group, an aryl group which may have 1 to 3 substituents selected from substituent group β, and a heteroaryl group which may have 1 to 3 substituents selected from substituent group β;

substituent group β is the group consisting of a halogen atom, a hydroxyl group, a C1-C6 alkyl group, and a C1-C6 alkoxy group;

m is an integer of 0 to 3;
each $R^2$ may be the same or different and is a halogen atom, a C1-C6 alkyl group, a C1-C6 alkoxy group, or a C1-C6 alkoxy-C1-C6 alkyl group;
n is an integer of 0 to 4;
each $R^3$ may be the same or different and is a halogen atom, a C1-C6 alkyl group, a C1-C6 alkoxy group, or a C1-C6 alkoxy-C1-C6 alkyl group;
$R^4$ and $R^5$ are each independently a hydrogen atom, a halogen atom, a C1-C6 alkyl group, a C1-C6 alkoxy group, or a C1-C6 alkoxy-C1-C6 alkyl group;
$R^6$ is —C(O)O—$R^{6a}$, —C(O)—$R^{6b}$, or —S(O)$_2$—$R^{6c}$;
$R^{6a}$ is a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an aryl group which may have 1 to 3 substituents selected from substituent group β, or a heteroaryl group which may have 1 to 3 substituents selected from substituent group β;

$R^{6b}$ is a hydrogen atom, a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an amino group, a mono- or di(C1-C6 alkyl)amino group, an aryl group which may have 1 to 3 substituents selected from substituent group β, or a heteroaryl group which may have 1 to 3 substituents selected from substituent group β;

$R^{6c}$ is a C1-C6 alkyl group; and $R^7$ is a hydrogen atom, a halogen atom, or a C1-C6 alkyl group;

(2) the compound according to the above (1) or a pharmaceutically acceptable salt thereof, wherein $R^1$ is a C1-C6 alkyl group which may have 1 to 3 substituents selected from substituent group α, a C3-C7 cycloalkyl group which may have 1 to 3 substituents selected from substituent group β, an amino group, or a mono- or di(C1-C6 alkyl)amino group;

(3) the compound according to the above (1) or (2) or a pharmaceutically acceptable salt thereof, wherein $R^1$ is a C1-C6 alkyl group which may have 1 to 3 substituents selected from substituent group α or a C3-C7 cycloalkyl group which may have 1 to 3 substituents selected from substituent group β;

(4) the compound according to any one of the above (1) to (3) or a pharmaceutically acceptable salt thereof, wherein m is 0;

(5) the compound according to any one of the above (1) to (3) or a pharmaceutically acceptable salt thereof, wherein m is 1, and $R^2$ is a halogen atom;

(6) the compound according to any one of the above (1) to (5) or a pharmaceutically acceptable salt thereof, wherein n is 0;

(7) the compound according to any one of the above (1) to (5) or a pharmaceutically acceptable salt thereof, wherein n is 1, and $R^3$ is a halogen atom;

(8) the compound according to any one of the above (1) to (7) or a pharmaceutically acceptable salt thereof, wherein $R^4$ is a hydrogen atom;

(9) the compound according to any one of the above (1) to (8) or a pharmaceutically acceptable salt thereof, wherein $R^5$ is a hydrogen atom, a C1-C6 alkyl group, or a C1-C6 alkoxy group;

(10) the compound according to any one of the above (1) to (9) or a pharmaceutically acceptable salt thereof, wherein $R^5$ is a hydrogen atom or a C1-C6 alkoxy group;

(11) the compound according to any one of the above (1) to (10) or a pharmaceutically acceptable salt thereof, wherein $R^6$ is —C(O)O—$R^{6a}$;

(12) the compound according to any one of the above (1) to (11) or a pharmaceutically acceptable salt thereof, wherein $R^{6a}$ is a C1-C6 alkyl group which may have 1 to 3 substituents selected from substituent group α, a C3-C7 cycloalkyl group which may have 1 to 3 substituents selected from substituent group β, an aryl group which may have 1 to 3 substituents selected from substituent group β, or a heteroaryl group which may have 1 to 3 substituents selected from substituent group β;

(13) the compound according to any one of the above (1) to (10) or a pharmaceutically acceptable salt thereof, wherein $R^6$ is —C(O)—$R^{6b}$;

(14) the compound according to any one of the above (1) to (10) and (13) or a pharmaceutically acceptable salt thereof, wherein $R^{6b}$ is a C1-C6 alkyl group which may have 1 to 3 substituents selected from substituent group α or an aryl group which may have 1 to 3 substituents selected from substituent group β;

(15) the compound according to any one of the above (1) to (10), (13), and (14) or a pharmaceutically acceptable salt thereof, wherein $R^{6b}$ is a C1-C6 alkyl group which may have 1 to 3 substituents selected from substituent group α;

(16) the compound according to any one of the above (1) to (10) or a pharmaceutically acceptable salt thereof, wherein $R^6$ is —S(O)$_2$—$R^{6c}$;

(17) the compound according to any one of the above (1) to (10) and (16) or a pharmaceutically acceptable salt thereof, wherein $R^{6c}$ is a C1-C4 alkyl group;

(18) the compound according to any one of the above (1) to (17) or a pharmaceutically acceptable salt thereof, wherein $R^7$ is a hydrogen atom, a fluorine atom, or a C1-C3 alkyl group;

(19) a compound represented by the general formula (II) or a pharmaceutically acceptable salt thereof:

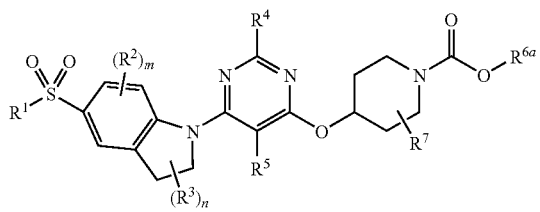

(II)

wherein $R^1$ is a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an amino group, or a mono- or di(C1-C6 alkyl)amino group;

substituent group α is the group consisting of a halogen atom, a hydroxyl group, a C1-C6 alkoxy group, a C3-C7 cycloalkyl group which may have 1 to 3 substituents selected from substituent group β, an amino group, a mono- or di(C1-C6 alkyl)amino group, an aryl group which may have 1 to 3 substituents selected from substituent group β, and a heteroaryl group which may have 1 to 3 substituents selected from substituent group β;

substituent group β is the group consisting of a halogen atom, a hydroxyl group, a C1-C6 alkyl group, and a C1-C6 alkoxy group;

m is an integer of 0 to 3;

each $R^2$ may be the same or different and is a halogen atom, a C1-C6 alkyl group, a C1-C6 alkoxy group, or a C1-C6 alkoxy-C1-C6 alkyl group;

n is an integer of 0 to 4;

each $R^3$ may be the same or different and is a halogen atom, a C1-C6 alkyl group, a C1-C6 alkoxy group, or a C1-C6 alkoxy-C1-C6 alkyl group;

$R^4$ and $R^5$ are each independently a hydrogen atom, a halogen atom, a C1-C6 alkyl group, a C1-C6 alkoxy group, or a C1-C6 alkoxy-C1-C6 alkyl group;

$R^{6a}$ is a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an aryl group which may have 1 to 3 substituents selected from substituent group β, or a heteroaryl group which may have 1 to 3 substituents selected from substituent group β; and $R^7$ is a hydrogen atom, a halogen atom, or a C1-C6 alkyl group;

(20) a compound selected from the group consisting of the following:

isopropyl 4-({6-[5-(methylsulfonyl)indolin-1-yl]pyrimidin-4-yl}oxy)piperidine-1-carboxylate;

isobutyl 4-({6-[5-(methylsulfonyl)indolin-1-yl]pyrimidin-4-yl}oxy)piperidine-1-carboxylate;

tert-butyl 4-({6-[5-(methylsulfonyl)indolin-1-yl]pyrimidin-4-yl}oxy)piperidine-1-carboxylate;

cyclobutyl 4-({6-[5-(methylsulfonyl)indolin-1-yl]pyrimidin-4-yl}oxy)piperidine-1-carboxylate;

cyclopentyl 4-({6-[5-(methylsulfonyl)indolin-1-yl]pyrimidin-4-yl}oxy)piperidine-1-carboxylate;

1-ethylpropyl 4-({6-[5-(methylsulfonyl)indolin-1-yl]pyrimidin-4-yl}oxy)piperidine-1-carboxylate;

cyclopropylmethyl 4-({6-[5-(methylsulfonyl)indolin-1-yl]pyrimidin-4-yl}oxy)piperidine-1-carboxylate;

3-furylmethyl 4-({6-[5-(methylsulfonyl)indolin-1-yl]pyrimidin-4-yl}oxy)piperidine-1-carboxylate;

1-cyclopropylethyl 4-({6-[5-(methylsulfonyl)indolin-1-yl]pyrimidin-4-yl}oxy)piperidine-1-carboxylate;

2-fluoroethyl 4-({6-[5-(methylsulfonyl)indolin-1-yl]pyrimidin-4-yl}oxy)piperidine-1-carboxylate;

2,2-difluoroethyl 4-({6-[5-(methylsulfonyl)indolin-1-yl]pyrimidin-4-yl}oxy)piperidine-1-carboxylate;

2,2,2-trifluoroethyl 4-({6-[5-(methylsulfonyl)indolin-1-yl]pyrimidin-4-yl}oxy)piperidine-1-carboxylate;

1-(6-{[1-(3-methylbutanoyl)piperidin-4-yl]oxy}pyrimidin-4-yl)-5-(methylsulfonyl)indoline;

isopropyl 4-({5-methoxy-6-[5-(methylsulfonyl)indolin-1-yl]pyrimidin-4-yl}oxy)piperidine-1-carboxylate;

tert-butyl 4-({5-methoxy-6-[5-(methylsulfonyl)indolin-1-yl]pyrimidin-4-yl}oxy)piperidine-1-carboxylate;

isopropyl 4-({6-[5-(ethylsulfonyl)indolin-1-yl]pyrimidin-4-yl}oxy)piperidine-1-carboxylate;

isobutyl 4-({6-[5-(ethylsulfonyl)indolin-1-yl]pyrimidin-4-yl}oxy)piperidine-1-carboxylate;

sec-butyl 4-({6-[5-(ethylsulfonyl)indolin-1-yl]pyrimidin-4-yl}oxy)piperidine-1-carboxylate;

cyclobutyl 4-({6-[5-(ethylsulfonyl)indolin-1-yl]pyrimidin-4-yl}oxy)piperidine-1-carboxylate;

cyclopropylmethyl 4-({6-[5-(ethylsulfonyl)indolin-1-yl]pyrimidin-4-yl}oxy)piperidine-1-carboxylate;

2,2-difluoroethyl 4-({6-[5-(ethylsulfonyl)indolin-1-yl]pyrimidin-4-yl}oxy)piperidine-1-carboxylate;

2,2,2-trifluoroethyl 4-({6-[5-(ethylsulfonyl)indolin-1-yl]pyrimidin-4-yl}oxy)piperidine-1-carboxylate;

tert-butyl 4-[(6-{5-[(2-fluoroethyl)sulfonyl]indolin-1-yl}pyrimidin-4-yl)oxy]piperidine-1-carboxylate;

tert-butyl 4-({6-[5-(propylsulfonyl)indolin-1-yl]pyrimidin-4-yl}oxy)piperidine-1-carboxylate;

2,2,2-trifluoroethyl 4-({6-[5-(propylsulfonyl)indolin-1-yl]pyrimidin-4-yl}oxy)piperidine-1-carboxylate;

tert-butyl 4-({6-[5-(cyclobutylsulfonyl)indolin-1-yl]pyrimidin-4-yl}oxy)piperidine-1-carboxylate;

tert-butyl 4-({6-[5-(methylsulfinyl)indolin-1-yl]pyrimidin-4-yl}oxy)piperidine-1-carboxylate;

2,2,2-trifluoroethyl 4-({6-[5-(methylsulfinyl)indolin-1-yl]pyrimidin-4-yl}oxy)piperidine-1-carboxylate; and isopropyl cis-3-fluoro-4-[6-(5-methanesulfonyl-2,3-dihydro-indol-1-yl)-pyrimidin-4-yloxy]-piperidine-1-carboxylate;

(21) a pharmaceutical composition comprising a compound according to any one of the above (1) to (20) or a pharmaceutically acceptable salt thereof as an active ingredient;

(22) the pharmaceutical composition according to the above (21), for treating and/or preventing type 1 diabetes mellitus, type 2 diabetes mellitus, or diabetes-related disease;

(23) the pharmaceutical composition according to the above (21), for treating and/or preventing adiposity;

(24) use of a compound according to any one of the above (1) to (20) or a pharmaceutically acceptable salt thereof for producing a pharmaceutical composition;

(25) the use according to the above (24), wherein the pharmaceutical composition is a composition for treating and/or preventing type 1 diabetes mellitus, type 2 diabetes mellitus, or diabetes-related disease;

(26) the use according to the above (24), wherein the pharmaceutical composition is a composition for treating and/or preventing adiposity;

(27) a method for treating and/or preventing disease, comprising administering a pharmacologically effective amount of a compound according to any one of the above (1) to (20) or a pharmaceutically acceptable salt thereof to a mammal;

(28) the method according to the above (27), wherein the disease is type 1 diabetes mellitus, type 2 diabetes mellitus, or diabetes-related disease;

(29) the method according to the above (27), wherein the disease is adiposity; and

(30) the method according to any one of the above (27) to (29), wherein the mammal is a human.

ADVANTAGES OF THE INVENTION

The present invention can provide a pyrimidyl indoline compound having an excellent hypoglycemic effect or a pharmaceutically acceptable salt thereof and a pharmaceutical composition having excellent therapeutic and/or preventive effects on type 1 diabetes mellitus, type 2 diabetes mellitus, pregnancy diabetes, hyperglycemia caused by other factors, impaired glucose tolerance (IGT), diabetes-related disease (e.g., adiposity, hyperlipemia, hypercholesterolemia, lipid metabolism abnormality, hypertension, fatty liver, metabolic syndrome, edema, cardiac failure, angina pectoris, myocardial infarction, arteriosclerosis, hyperuricemia, and gout), or complications from diabetes (e.g., retinopathy, nephropathy, neuropathy, cataract, foot gangrene, infectious disease, and ketosis).

DETAILED DESCRIPTION OF THE INVENTION

In the present specification, "p" in $S(O)_p$ represents the number of oxygen atoms bound to the sulfur atom.

In the present specification, a "C1-C6 alkyl group" refers to a linear or branched alkyl group having 1 to 6 carbon atoms and includes methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl groups.

In the present specification, a "C3-C7 cycloalkyl group" refers to a saturated cyclic hydrocarbon group having 3 to 7 carbon atoms and includes cyclopropyl, cyclobutyl, cyclopentyl, cyclohexyl, and cycloheptyl groups.

In the present specification, a "C2-C6 alkynyl group" refers to a linear or branched alkynyl group having 2 to 6 carbon atoms and includes ethynyl, 2-propynyl, 1-methyl-2-propynyl, 2-ethyl-2-propynyl, 2-butynyl, 1-methyl-2-butynyl, 3-butynyl, 2-pentynyl, 1-methyl-2-pentynyl, and 2-hexynyl groups.

In the present specification, a "C2-C6 alkenyl group" refers to a linear or branched alkenyl group having 2 to 6 carbon atoms and includes ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 1-ethyl-3-butenyl, 1-pentenyl, and 1-hexenyl groups.

In the present specification, a "mono- or di(C1-C6 alkyl) amino group" refers to a group in which one or two of the "C1-C6 alkyl groups" bind to an amino group. Examples of the mono(C1-C6 alkyl)amino group include methylamino, ethylamino, propylamino, isopropylamino, butylamino, isobutylamino, sec-butylamino, tert-butylamino, pentylamino, isopentylamino, 2-methylbutylamino, neopentylamino, 1-ethylpropylamino, hexylamino, isohexylamino, 4-methylpentylamino, 3-methylpentylamino, 2-methylpentylamino, and 1-methylpentylamino groups. Examples of the di(C1-C6 alkyl)amino group include dimethylamino, diethylamino, N-ethyl-N-methylamino, dipropylamino, dibutylamino, dipentylamino, and dihexylamino groups.

In the present specification, a "halogen atom" refers to a fluorine, chlorine, bromine, or iodine atom.

In the present specification, a "C1-C6 alkoxy group" refers to a group in which the "C1-C6 alkyl group" binds to an oxygen atom and includes methoxy, ethoxy, propoxy, isopropoxy, butoxy, isobutoxy, sec-butoxy, tert-butoxy, pentoxy, isopentoxy, 2-methylbutoxy, neopentoxy, hexyloxy, 4-methylpentoxy, 3-methylpentoxy, and 2-methylpentoxy groups.

In the present specification, an "aryl group" refers to an aromatic hydrocarbon group having 5 to 14 carbon atoms and includes phenyl, indenyl, naphthyl, phenanthrenyl, and anthracenyl groups.

In the present specification, a "heteroaryl group" refers to a 5- to 8-membered aromatic heterocyclic ring containing 1 to 5 heteroatoms which may be the same or different and are selected from the group consisting of oxygen, sulfur, and nitrogen atoms, and includes furanyl, thienyl, pyrrolyl, oxazolyl, isoxazolyl, thiazolyl, thianyl, pyridyl, pyridazinyl, pyrimidinyl, pyrazolyl, imidazolyl, triazinyl, thiadiazolyl, imidazothiazolyl, benzisoxazolyl, chromenyl, quinolyl, benzothianyl, quinoxalinyl, and benzotriazinyl groups.

In the present specification, a "C1-C6 alkoxy-C1-C6 alkyl group" refers to a group in which the "C1-C6 alkyl group" is substituted by the "C1-C6 alkoxy group" and includes methoxymethyl, methoxyethyl, methoxypropyl, methoxybutyl, ethoxymethyl, ethoxyethyl, ethoxypropyl, ethoxybutyl, butoxymethyl, butoxyethyl, butoxypropyl, and butoxybutyl groups.

A "pharmaceutically acceptable salt" refers to a salt that is formed by reacting a compound of the present invention with an acid or a base.

Examples of the salt include: hydrohalides such as hydrofluoride, hydrochloride, hydrobromide, and hydroiodide; inorganic acid salts such as hydrochloride, nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, ascorbate, tartrate, oxalate, and maleate; alkali metal salts such as sodium salt, potassium salt, and lithium salt; alkaline-earth metal salts such as calcium salt and magnesium salt; metal salts such as aluminum salt and iron salt; inorganic salts such as ammonium salt; amine salts such as organic salts, for example, t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, and tris(hydroxymethyl)aminomethane salt; and amino acid salts such as glycine salt, lysine salt, arginine salt, ornithine salt, glutamate, and aspartate.

The compound of the present invention represented by the general formula (I) or (II), when left in the air or recrystallized, may associate with adsorbed water through water absorption to form a hydrate. Such a hydrate is also encompassed by the salt of the present invention.

The compound of the present invention represented by the general formula (I) or (II) may have an asymmetric carbon atom in its molecule and therefore includes optical isomers. All these isomers and mixtures of these isomers are represented by a single formula, i.e., the general formula (I) or (II). Thus, the compound of the present invention represented by the general formula (I) or (II) also encompasses all such optical isomers and mixtures of these optical isomers in any ratio.

In the general formula (I) or (II), $R^1$ is preferably a C1-C6 alkyl group which may have 1 to 3 substituents selected from substituent group α, a C3-C7 cycloalkyl group which may have 1 to 3 substituents selected from substituent group β, an amino group, or a mono(C1-C6 alkyl)amino group, more preferably a C1-C6 alkyl group which may have 1 to 3 substituents selected from substituent group α or a C3-C7 cycloalkyl group which may have 1 to 3 substituents selected from substituent group β, even more preferably a methyl, ethyl, propyl, isobutyl, 2-fluoroethyl, or cyclobutyl group.

In the general formula (I) or (II), m is preferably 0 or 1, more preferably 0.

In the general formula (I) or (II), each $R^2$ may be the same or different and is preferably a halogen atom.

In the general formula (I) or (II), n is preferably 0 or 1, more preferably 0.

In the general formula (I) or (II), each $R^3$ may be the same or different and is preferably a halogen atom.

In the general formula (I) or (II), $R^4$ is preferably a hydrogen atom.

In the general formula (I) or (II), $R^5$ is preferably a hydrogen atom, a C1-C6 alkyl group, or a C1-C6 alkoxy group, more preferably a hydrogen atom or a C1-C6 alkoxy group, even more preferably a hydrogen atom or a methoxy group.

In the general formula (I) or (II), $R^{6a}$ is preferably a C1-C6 alkyl group which may have 1 to 3 substituents selected from substituent group α, a C3-C7 cycloalkyl group which may have 1 to 3 substituents selected from substituent group β, an aryl group which may have 1 to 3 substituents selected from substituent group β, or a heteroaryl group which may have 1 to 3 substituents selected from substituent group β, more preferably a C1-C6 alkyl group which may have 1 to 3 substituents selected from substituent group α, a C3-C7 cycloalkyl group which may have 1 to 3 substituents selected from substituent group β, or a heteroaryl group which may have 1 to 3 substituents selected from substituent group β, even more preferably an isopropyl, isobutyl, sec-butyl, tert-butyl, 1-ethylpropyl, 2-fluoroethyl, 2,2-difluoroethyl, 2,2,2- trifluoroethyl, cyclopentylmethyl, 1-cyclopropylethyl, cyclopentyl, cyclobutyl, or 3-furylmethyl group.

In the general formula (I), $R^{6b}$ is preferably a C1-C6 alkyl group which may have 1 to 3 substituents selected from substituent group α or an aryl group which may have 1 to 3 substituents selected from substituent group β, more preferably a C1-C6 alkyl group which may have 1 to 3 substituents selected from substituent group α, even more preferably an isobutyl group.

In the general formula (I), $R^{6c}$ is preferably a C1-C4 alkyl group, more preferably a butyl group.

In the general formula (I) or (II), $R^7$ is preferably a hydrogen atom, a fluorine atom, or a C1-C3 alkyl group, more preferably a hydrogen atom or a methyl group.

Specific examples of the compound of the present invention represented by the general formula (I) can include compounds described in Table 1 below. However, the present invention is not intended to be limited to these compounds. In Table 1 below, the following abbreviations are used:
Aly: allyl group
Bn: benzyl group
Bu: butyl group
cBu: cyclobutyl group
cHp: cycloheptyl group
cHx: cyclohexyl group
cPn: cyclopentyl group
cPr: cyclopropyl group
Et: ethyl group
Ety: ethynyl group
Fur: furyl group
Hx: n-hexyl group
iBu: isobutyl group
iPr: isopropyl group
Me: methyl group
NPn: 2,2-dimethyl-1-propyl group
Ph: phenyl group
Pn: n-pentyl group
Prpe: propenyl group
Pyr: pyridyl group
sBu: sec-butyl group
tBu: tert-butyl group In the column $R^2$, the symbol "—" indicates that m is 0. In the column $R^3$, the symbol "—" indicates that n is 0.

TABLE 1

(I)

[Chemical structure showing a substituted indoline-pyrimidine-piperidine compound with substituents $R^1(O)_pS$, $(R^2)_m$, $(R^3)_n$, $R^4$, $R^5$, $R^6$, $R^7$]

| No. | $S(O)_pR^1$ | $R^2$ | $R^3$ | $R^4$ | $R^5$ | $R^6$ | $R^7$ |
|---|---|---|---|---|---|---|---|
| 1 | S(O)₂Me | — | — | H | H | C(O)OMe | H |
| 2 | S(O)₂Me | — | — | H | H | C(O)OEt | H |
| 3 | S(O)₂Me | — | — | H | H | C(O)OPr | H |
| 4 | S(O)₂Me | — | — | H | H | C(O)O(iPr) | H |
| 5 | S(O)₂Me | — | — | H | H | C(O)OBu | H |
| 6 | S(O)₂Me | — | — | H | H | C(O)O(iBu) | H |
| 7 | S(O)₂Me | — | — | H | H | C(O)O(sBu) | H |
| 8 | S(O)₂Me | — | — | H | H | C(O)O(tBu) | H |
| 9 | S(O)₂Me | — | — | H | H | C(O)O(cBu) | H |
| 10 | S(O)₂Me | — | — | H | H | C(O)OPn | H |
| 11 | S(O)₂Me | — | — | H | H | C(O)O(cPn) | H |
| 12 | S(O)₂Me | — | — | H | H | C(O)OHx | H |
| 13 | S(O)₂Me | — | — | H | H | C(O)O(1-Et-Pr) | H |
| 14 | S(O)₂Me | — | — | H | H | C(O)O(1,1-di-Me-Pr) | H |
| 15 | S(O)₂Me | — | — | H | H | C(O)O(1-Me-cBu) | H |
| 16 | S(O)₂Me | — | — | H | H | C(O)O(1-Me-cPn) | H |
| 17 | S(O)₂Me | — | — | H | H | C(O)O(1-Me-cHx) | H |
| 18 | S(O)₂Me | — | — | H | H | C(O)O(NPn) | H |
| 19 | S(O)₂Me | — | — | H | H | C(O)OCH₂(cPr) | H |
| 20 | S(O)₂Me | — | — | H | H | C(O)OCH₂(cBu) | H |
| 21 | S(O)₂Me | — | — | H | H | C(O)OCH₂(cPn) | H |
| 22 | S(O)₂Me | — | — | H | H | C(O)OCH₂(cHx) | H |
| 23 | S(O)₂Me | — | — | H | H | C(O)OCH₂(cHp) | H |
| 24 | S(O)₂Me | — | — | H | H | C(O)OCH₂(1-Me-cPr) | H |
| 25 | S(O)₂Me | — | — | H | H | C(O)OCH₂(2-Fur) | H |
| 26 | S(O)₂Me | — | — | H | H | C(O)OCH₂(3-Fur) | H |
| 27 | S(O)₂Me | — | — | H | H | C(O)OCH₂(cPn) | H |
| 28 | S(O)₂Me | — | — | H | H | C(O)OCHMe(cPr) | H |
| 29 | S(O)₂Me | — | — | H | H | C(O)OCH(cPr)₂ | H |
| 30 | S(O)₂Me | — | — | H | H | C(O)O(CH₂)₂(cPr) | H |
| 31 | S(O)₂Me | — | — | H | H | C(O)O(Aly) | H |
| 32 | S(O)₂Me | — | — | H | H | C(O)O(2-F-2-Prpe) | H |
| 33 | S(O)₂Me | — | — | H | H | C(O)OCH₂(Ety) | H |
| 34 | S(O)₂Me | — | — | H | H | C(O)O(CH₂)₂F | H |
| 35 | S(O)₂Me | — | — | H | H | C(O)OCH₂CHMeF | H |
| 36 | S(O)₂Me | — | — | H | H | C(O)O(CH₂)₂Cl | H |
| 37 | S(O)₂Me | — | — | H | H | C(O)O(CH₂)₂OH | H |

TABLE 1-continued

| No. | S(O)$_p$R$^1$ | R$^2$ | R$^3$ | R$^4$ | R$^5$ | R$^6$ | R$^7$ |
|---|---|---|---|---|---|---|---|
| 38 | S(O)$_2$Me | — | — | H | H | C(O)OCH$_2$[(R)—CHMe(OH)] | H |
| 39 | S(O)$_2$Me | — | — | H | H | C(O)OCH$_2$[(S)—CHMe(OH)] | H |
| 40 | S(O)$_2$Me | — | — | H | H | C(O)O(CH$_2$)$_2$OMe | H |
| 41 | S(O)$_2$Me | — | — | H | H | C(O)O(CH$_2$)$_2$OEt | H |
| 42 | S(O)$_2$Me | — | — | H | H | C(O)O(CH$_2$)$_2$OPr | H |
| 43 | S(O)$_2$Me | — | — | H | H | C(O)O(CH$_2$)$_2$NH$_2$ | H |
| 44 | S(O)$_2$Me | — | — | H | H | C(O)O(CH$_2$)$_2$NHMe | H |
| 45 | S(O)$_2$Me | — | — | H | H | C(O)O(CH$_2$)$_2$NMe$_2$ | H |
| 46 | S(O)$_2$Me | — | — | H | H | C(O)OPh | H |
| 47 | S(O)$_2$Me | — | — | H | H | C(O)O(4-F-Ph) | H |
| 48 | S(O)$_2$Me | — | — | H | H | C(O)O(4-OMe-Ph) | H |
| 49 | S(O)$_2$Me | — | — | H | H | C(O)OBn | H |
| 50 | S(O)$_2$Me | — | — | H | H | C(O)OCH$_2$(4-F-Ph) | H |
| 51 | S(O)$_2$Me | — | — | H | H | C(O)OCH$_2$(4-OMe-Ph) | H |
| 52 | S(O)$_2$Me | — | — | H | H | C(O)OCHMePh | H |
| 53 | S(O)$_2$Me | — | — | H | H | C(O)OCH$_2$CHF$_2$ | H |
| 54 | S(O)$_2$Me | — | — | H | H | C(O)OCH$_2$CF$_3$ | H |
| 55 | S(O)$_2$Me | — | — | H | H | C(O)OCH(CH$_2$F)$_2$ | H |
| 56 | S(O)$_2$Me | — | — | H | H | C(O)O(2-F-1-Me-Et) | H |
| 57 | S(O)$_2$Me | — | — | H | H | C(O)OCH$_2$(2,2-di-F-cPr) | H |
| 58 | S(O)$_2$Me | — | — | H | H | C(O)OCH$_2$(1-F-cPr) | H |
| 59 | S(O)$_2$Me | — | — | H | H | C(O)OCH$_2$(2,2-di-F-cBu) | H |
| 60 | S(O)$_2$Me | — | — | H | H | C(O)H | H |
| 61 | S(O)$_2$Me | — | — | H | H | C(O)Me | H |
| 62 | S(O)$_2$Me | — | — | H | H | C(O)CHF$_2$ | H |
| 63 | S(O)$_2$Me | — | — | H | H | C(O)CF$_3$ | H |
| 64 | S(O)$_2$Me | — | — | H | H | C(O)Et | H |
| 65 | S(O)$_2$Me | — | — | H | H | C(O)Pr | H |
| 66 | S(O)$_2$Me | — | — | H | H | C(O)(iPr) | H |
| 67 | S(O)$_2$Me | — | — | H | H | C(O)(cPr) | H |
| 68 | S(O)$_2$Me | — | — | H | H | C(O)Bu | H |
| 69 | S(O)$_2$Me | — | — | H | H | C(O)(iBu) | H |
| 70 | S(O)$_2$Me | — | — | H | H | C(O)(cBu) | H |
| 71 | S(O)$_2$Me | — | — | H | H | C(O)Pn | H |
| 72 | S(O)$_2$Me | — | — | H | H | C(O)(cPn) | H |
| 73 | S(O)$_2$Me | — | — | H | H | C(O)(NPn) | H |
| 74 | S(O)$_2$Me | — | — | H | H | C(O)Hx | H |
| 75 | S(O)$_2$Me | — | — | H | H | C(O)(Aly) | H |
| 76 | S(O)$_2$Me | — | — | H | H | C(O)CH$_2$(Aly) | H |
| 77 | S(O)$_2$Me | — | — | H | H | C(O)(CH$_2$)$_2$(Ety) | H |
| 78 | S(O)$_2$Me | — | — | H | H | C(O)CH$_2$(cPr) | H |
| 79 | S(O)$_2$Me | — | — | H | H | C(O)(CH$_2$)$_2$(cPr) | H |
| 80 | S(O)$_2$Me | — | — | H | H | C(O)(CH$_2$)$_3$(cPr) | H |
| 81 | S(O)$_2$Me | — | — | H | H | C(O)CH$_2$CF$_3$ | H |
| 82 | S(O)$_2$Me | — | — | H | H | C(O)(CH$_2$)$_2$CF$_3$ | H |
| 83 | S(O)$_2$Me | — | — | H | H | C(O)(CH$_2$)$_3$CF$_3$ | H |
| 84 | S(O)$_2$Me | — | — | H | H | C(O)Ph | H |
| 85 | S(O)$_2$Me | — | — | H | H | C(O)(4-F-Ph) | H |
| 86 | S(O)$_2$Me | — | — | H | H | C(O)(4-OMe-Ph) | H |
| 87 | S(O)$_2$Me | — | — | H | H | C(O)(2-Pyr) | H |
| 88 | S(O)$_2$Me | — | — | H | H | C(O)(3-Pyr) | H |
| 89 | S(O)$_2$Me | — | — | H | H | C(O)(4-Pyr) | H |
| 90 | S(O)$_2$Me | — | — | H | H | C(O)Bn | H |
| 91 | S(O)$_2$Me | — | — | H | H | C(O)CH$_2$(4-F-Ph) | H |
| 92 | S(O)$_2$Me | — | — | H | H | C(O)CH$_2$(4-OMe-Ph) | H |
| 93 | S(O)$_2$Me | — | — | H | H | C(O)(CH$_2$)$_2$Ph | H |
| 94 | S(O)$_2$Me | — | — | H | H | C(O)(CH$_2$)$_2$(4-F-Ph) | H |
| 95 | S(O)$_2$Me | — | — | H | H | C(O)(CH$_2$)$_2$(4-OMe-Ph) | H |
| 96 | S(O)$_2$Me | — | — | H | H | C(O)(CH$_2$)$_3$Ph | H |
| 97 | S(O)$_2$Me | — | — | H | H | C(O)CH$_2$CHMe(OH) | H |
| 98 | S(O)$_2$Me | — | — | H | H | C(O)CH$_2$OMe | H |
| 99 | S(O)$_2$Me | — | — | H | H | C(O)CH$_2$OEt | H |
| 100 | S(O)$_2$Me | — | — | H | H | C(O)CH$_2$NH$_2$ | H |
| 101 | S(O)$_2$Me | — | — | H | H | C(O)CH$_2$NHMe | H |
| 102 | S(O)$_2$Me | — | — | H | H | C(O)CH$_2$NMe$_2$ | H |

TABLE 1-continued (I)

| No. | S(O)$_p$R$^1$ | R$^2$ | R$^3$ | R$^4$ | R$^5$ | R$^6$ | R$^7$ |
|---|---|---|---|---|---|---|---|
| 103 | S(O)$_2$Me | — | — | H | H | C(O)NHMe | H |
| 104 | S(O)$_2$Me | — | — | H | H | C(O)NHEt | H |
| 105 | S(O)$_2$Me | — | — | H | H | C(O)NHPr | H |
| 106 | S(O)$_2$Me | — | — | H | H | C(O)NH(iPr) | H |
| 107 | S(O)$_2$Me | — | — | H | H | C(O)NH(cPr) | H |
| 108 | S(O)$_2$Me | — | — | H | H | C(O)NHBu | H |
| 109 | S(O)$_2$Me | — | — | H | H | C(O)NH(iBu) | H |
| 110 | S(O)$_2$Me | — | — | H | H | C(O)NH(cBu) | H |
| 111 | S(O)$_2$Me | — | — | H | H | C(O)NH(tBu) | H |
| 112 | S(O)$_2$Me | — | — | H | H | C(O)NHPn | H |
| 113 | S(O)$_2$Me | — | — | H | H | C(O)NH(cPn) | H |
| 114 | S(O)$_2$Me | — | — | H | H | C(O)NMe$_2$ | H |
| 115 | S(O)$_2$Me | — | — | H | H | C(O)NEt$_2$ | H |
| 116 | S(O)$_2$Me | — | — | H | H | C(O)NPr$_2$ | H |
| 117 | S(O)$_2$Me | — | — | H | H | C(O)NBu$_2$ | H |
| 118 | S(O)$_2$Me | — | — | H | H | C(O)NPn$_2$ | H |
| 119 | S(O)$_2$Me | — | — | H | H | C(O)NMeEt | H |
| 120 | S(O)$_2$Me | — | — | H | H | C(O)NMePr | H |
| 121 | S(O)$_2$Me | — | — | H | H | C(O)NEtPr | H |
| 122 | S(O)$_2$Me | — | — | H | H | S(O)$_2$Et | H |
| 123 | S(O)$_2$Me | — | — | H | H | S(O)$_2$Pr | H |
| 124 | S(O)$_2$Me | — | — | H | H | S(O)$_2$(iPr) | H |
| 125 | S(O)$_2$Me | — | — | H | H | S(O)$_2$(cPr) | H |
| 126 | S(O)$_2$Me | — | — | H | H | S(O)$_2$Bu | H |
| 127 | S(O)$_2$Me | — | — | H | H | S(O)$_2$(iBu) | H |
| 128 | S(O)$_2$Me | — | — | H | H | S(O)$_2$(cBu) | H |
| 129 | S(O)$_2$Me | — | — | H | H | S(O)$_2$Pn | H |
| 130 | S(O)$_2$Me | — | — | H | H | S(O)$_2$Hx | H |
| 131 | S(O)$_2$Me | 6-F | — | H | H | C(O)O(iPr) | H |
| 132 | S(O)$_2$Me | 6-F | — | H | H | C(O)O(iBu) | H |
| 133 | S(O)$_2$Me | 6-F | — | H | H | C(O)O(tBu) | H |
| 134 | S(O)$_2$Me | 6-F | — | H | H | C(O)OCH$_2$(cPr) | H |
| 135 | S(O)$_2$Me | 6-F | — | H | H | C(O)O(CH)$_2$F | H |
| 136 | S(O)$_2$Me | 6-F | — | H | H | C(O)OBn | H |
| 137 | S(O)$_2$Me | 6-F | — | H | H | C(O)OCH$_2$CHF | H |
| 138 | S(O)$_2$Me | 6-F | — | H | H | C(O)OCH$_2$CF$_3$ | H |
| 139 | S(O)$_2$Me | 6-F | — | H | H | C(O)(iBu) | H |
| 140 | S(O)$_2$Me | 7-F | — | H | H | C(O)O(iPr) | H |
| 141 | S(O)$_2$Me | 7-F | — | H | H | C(O)O(tBu) | H |
| 142 | S(O)$_2$Me | — | — | H | H | C(O)O(iPr) | H |
| 143 | S(O)$_2$Me | — | — | H | H | C(O)O(tBu) | H |
| 144 | S(O)$_2$Me | 4-F | — | H | H | C(O)O(iPr) | H |
| 145 | S(O)$_2$Me | 4-F | — | H | H | C(O)O(tBu) | H |
| 146 | S(O)$_2$Me | — | — | H | F | C(O)O(iPr) | H |
| 147 | S(O)$_2$Me | — | — | H | F | C(O)O(iBu) | H |
| 148 | S(O)$_2$Me | — | — | F | F | C(O)O(tBu) | H |
| 149 | S(O)$_2$Me | — | — | H | F | C(O)OCH$_2$(cPr) | H |
| 150 | S(O)$_2$Me | — | — | H | F | C(O)O(CH)$_2$F | H |
| 151 | S(O)$_2$Me | — | — | H | F | C(O)OBn | H |
| 152 | S(O)$_2$Me | — | — | H | F | C(O)OCH$_2$CHF$_2$ | H |
| 153 | S(O)$_2$Me | — | — | H | F | C(O)OCH$_2$CF$_3$ | H |
| 154 | S(O)$_2$Me | — | — | H | F | C(O)(iBu) | H |
| 155 | S(O)$_2$Me | 6-Cl | — | H | H | C(O)O(iPr) | H |
| 156 | S(O)$_2$Me | 6-Cl | — | H | H | C(O)O(iBu) | H |
| 157 | S(O)$_2$Me | 6-Cl | — | H | H | C(O)O(tBu) | H |
| 158 | S(O)$_2$Me | 6-Cl | — | H | H | C(O)OCH$_2$(cPr) | H |
| 159 | S(O)$_2$Me | 6-Cl | — | H | H | C(O)O(CH)$_2$F | H |
| 160 | S(O)$_2$Me | 6-Cl | — | H | H | C(O)OBn | H |
| 161 | S(O)$_2$Me | 6-Cl | — | H | H | C(O)OCH$_2$CHF$_2$ | H |
| 162 | S(O)$_2$Me | 6-Cl | — | H | H | C(O)OCH$_2$CF$_3$ | H |
| 163 | S(O)$_2$Me | 6-Cl | — | H | H | C(O)(iBu) | H |
| 164 | S(O)$_2$Me | — | — | H | Cl | C(O)O(iPr) | H |
| 165 | S(O)$_2$Me | — | — | H | Cl | C(O)O(tBu) | H |
| 166 | S(O)$_2$Me | — | — | H | Cl | C(O)OCH$_2$(cPR) | H |
| 167 | S(O)$_2$Me | — | — | H | Cl | C(O)O(CH$_2$)$_2$F | H |

TABLE 1-continued

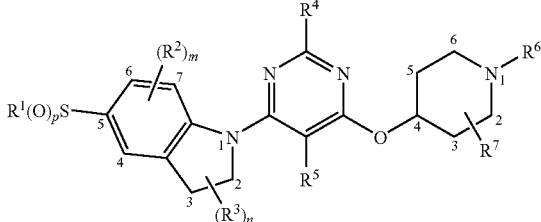

| No. | S(O)$_p$R$^1$ | R$^2$ | R$^3$ | R$^4$ | R$^5$ | R$^6$ | R$^7$ |
|---|---|---|---|---|---|---|---|
| 168 | S(O)$_2$Me | — | — | H | Cl | C(O)OBn | H |
| 169 | S(O)$_2$Me | — | — | H | Cl | C(O)OCH$_2$CHF$_2$ | H |
| 170 | S(O)$_2$Me | — | — | H | Cl | C(O)(iBu) | H |
| 171 | S(O)$_2$Me | — | — | H | Br | C(O)O(iPr) | H |
| 172 | S(O)$_2$Me | — | — | H | Br | C(O)O(tBu) | H |
| 173 | S(O)$_2$Me | 6-Me | — | H | H | C(O)O(iPr) | H |
| 174 | S(O)$_2$Me | 6-Me | — | H | H | C(O)O(tBu) | H |
| 175 | S(O)$_2$Me | 7-Me | — | H | H | C(O)O(iPr) | H |
| 176 | S(O)$_2$Me | 7-Me | — | H | H | C(O)O(tBu) | H |
| 177 | S(O)$_2$Me | — | 2-(R)-Me | H | H | C(O)O(iPr) | H |
| 178 | S(O)$_2$Me | — | 2-(R)-Me | H | H | C(O)O(tBu) | H |
| 179 | S(O)$_2$Me | — | 2-(S)-Me | H | H | C(O)O(iPr) | H |
| 180 | S(O)$_2$Me | — | 2-(S)-Me | H | H | C(O)O(tBu) | H |
| 181 | S(O)$_2$Me | — | 2,2-di-Me | H | H | C(O)O(iPr) | H |
| 182 | S(O)$_2$Me | — | 2,2-di-Me | H | H | C(O)O(tBu) | H |
| 183 | S(O)$_2$Me | — | 3-(R)-Me | H | H | C(O)O(iPr) | H |
| 184 | S(O)$_2$Me | — | 3-(R)-Me | H | H | C(O)O(tBu) | H |
| 185 | S(O)$_2$Me | — | 3-(S)-Me | H | H | C(O)O(iPr) | H |
| 186 | S(O)$_2$Me | — | 3-(S)-Me | H | H | C(O)O(tBu) | H |
| 187 | S(O)$_2$Me | — | 3,3-di-Me | H | H | C(O)O(iPr) | H |
| 188 | S(O)$_2$Me | — | 3,3-di-Me | H | H | C(O)O(tBu) | H |
| 189 | S(O)$_2$Me | 4-Me | — | H | H | C(O)O(iPr) | H |
| 190 | S(O)$_2$Me | 4-Me | — | H | H | C(O)O(tBu) | H |
| 191 | S(O)$_2$Me | — | — | Me | H | C(O)O(iPr) | H |
| 192 | S(O)$_2$Me | — | — | Me | H | C(O)O(iBu) | H |
| 193 | S(O)$_2$Me | — | — | Me | H | C(O)O(tBu) | H |
| 194 | S(O)$_2$Me | — | — | Me | H | C(O)OCH$_2$(cPr) | H |
| 195 | S(O)$_2$Me | — | — | Me | H | C(O)O(CH$_2$)$_2$F | H |
| 196 | S(O)$_2$Me | — | — | Me | H | C(O)OBn | H |
| 197 | S(O)$_2$Me | — | — | Me | H | C(O)OCH$_2$CHF$_2$ | H |
| 198 | S(O)$_2$Me | — | — | Me | H | C(O)OCH$_2$CF$_3$ | H |
| 199 | S(O)$_2$Me | — | — | Me | H | C(O)(iBu) | H |
| 200 | S(O)$_2$Me | — | — | H | Me | C(O)O(iPr) | H |
| 201 | S(O)$_2$Me | — | — | H | Me | C(O)O(iBu) | H |
| 202 | S(O)$_2$Me | — | — | H | Me | C(O)O(tBu) | H |
| 203 | S(O)$_2$Me | — | — | H | Me | C(O)O(1-Me-Pr) | H |
| 204 | S(O)$_2$Me | — | — | H | Me | C(O)OCH$_2$(2-Fur) | H |
| 205 | S(O)$_2$Me | — | — | H | Me | C(O)OCH$_2$(cPr) | H |
| 206 | S(O)$_2$Me | — | — | H | Me | C(O)OCH$_2$(cBu) | H |
| 207 | S(O)$_2$Me | — | — | H | Me | C(O)OCHMe(cPr) | H |
| 208 | S(O)$_2$Me | — | — | H | Me | C(O)O(CH$_2$)$_2$F | H |
| 209 | S(O)$_2$Me | — | — | H | Me | C(O)OBn | H |
| 210 | S(O)$_2$Me | — | — | H | Me | C(O)OCH$_2$CHF$_2$ | H |
| 211 | S(O)$_2$Me | — | — | H | Me | C(O)OCH$_2$CF$_3$ | H |
| 212 | S(O)$_2$Me | — | — | H | Me | C(O)(iBu) | H |
| 213 | S(O)$_2$Me | — | — | H | CH$_2$OH | C(O)O(iPr) | H |
| 214 | S(O)$_2$Me | — | — | H | CH$_2$OH | C(O)O(tBu) | H |
| 215 | S(O)$_2$Me | — | — | H | CH$_2$OMe | C(O)O(iPr) | H |
| 216 | S(O)$_2$Me | — | — | H | CH$_2$OMe | C(O)O(tBu) | H |
| 217 | S(O)$_2$Me | — | — | H | CH$_2$OMe | C(O)OCH$_2$(cPr) | H |
| 218 | S(O)$_2$Me | — | — | H | CH$_2$OMe | C(O)O(CH$_2$)$_2$F | H |
| 219 | S(O)$_2$Me | — | — | H | CH$_2$OMe | C(O)OBn | H |
| 220 | S(O)$_2$Me | — | — | H | CH$_2$OMe | C(O)OCH$_2$CF$_3$ | H |
| 221 | S(O)$_2$Me | — | — | H | CH$_2$OMe | C(O)(iBu) | H |
| 222 | S(O)$_2$Me | — | — | H | CH$_2$OEt | C(O)O(iPr) | H |
| 223 | S(O)$_2$Me | — | — | H | CH$_2$OEt | C(O)O(tBu) | H |
| 224 | S(O)$_2$Me | — | — | H | CH$_2$OEt | C(O)OCH$_2$(cPr) | H |
| 225 | S(O)$_2$Me | — | — | H | CH$_2$OEt | C(O)O(CH$_2$)$_2$F | H |
| 226 | S(O)$_2$Me | — | — | H | CH$_2$OEt | C(O)O(CH$_2$)$_2$F | H |
| 227 | S(O)$_2$Me | — | — | H | CH$_2$OEt | C(O)OCH$_2$CF$_3$ | H |
| 228 | S(O)$_2$Me | — | — | H | CH$_2$OEt | C(O)(iBu) | H |
| 229 | S(O)$_2$Me | — | — | H | Et | C(O)O(iPr) | H |
| 230 | S(O)$_2$Me | — | — | H | Et | C(O)O(iBu) | H |
| 231 | S(O)$_2$Me | — | — | H | Et | C(O)O(tBu) | H |
| 232 | S(O)$_2$Me | — | — | H | Et | C(O)OCH$_2$(cPr) | H |

TABLE 1-continued

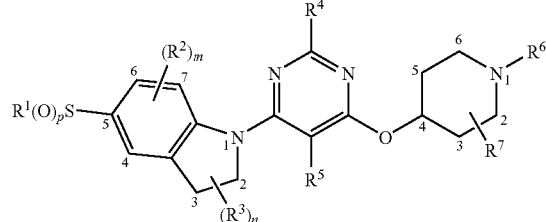

| No. | S(O)$_p$R$^1$ | R$^2$ | R$^3$ | R$^4$ | R$^5$ | R$^6$ | R$^7$ |
|---|---|---|---|---|---|---|---|
| 233 | S(O)$_2$Me | — | — | H | Et | C(O)O(CH$_2$)$_2$F | H |
| 234 | S(O)$_2$Me | — | — | H | Et | C(O)OBn | H |
| 235 | S(O)$_2$Me | — | — | H | Et | C(O)OCH$_2$CHF$_2$ | H |
| 236 | S(O)$_2$Me | — | — | H | Et | C(O)OCH$_2$CF$_3$ | H |
| 237 | S(O)$_2$Me | — | — | H | Et | C(O)(iBu) | H |
| 238 | S(O)$_2$Me | — | — | H | iPr | C(O)O(iPr) | H |
| 239 | S(O)$_2$Me | — | — | H | iPr | C(O)O(iBu) | H |
| 240 | S(O)$_2$Me | — | — | H | iPr | C(O)O(tBu) | H |
| 241 | S(O)$_2$Me | — | — | H | iPr | C(O)OCH$_2$(cPr) | H |
| 242 | S(O)$_2$Me | — | — | H | iPr | C(O)O(CH$_2$)$_2$F | H |
| 243 | S(O)$_2$Me | — | — | H | iPr | C(O)OBn | H |
| 244 | S(O)$_2$Me | — | — | H | iPr | C(O)OCH$_2$CHF$_2$ | H |
| 245 | S(O)$_2$Me | — | — | H | iPr | C(O)OCH$_2$CF$_3$ | H |
| 246 | S(O)$_2$Me | — | — | H | iPr | C(O)(iBu) | H |
| 247 | S(O)$_2$Me | — | — | H | cPr | C(O)O(iPr) | H |
| 248 | S(O)$_2$Me | — | — | H | cPr | C(O)O(tBu) | H |
| 249 | S(O)$_2$Me | 6-OMe | — | H | H | C(O)O(iPr) | H |
| 250 | S(O)$_2$Me | 6-OMe | — | H | H | C(O)O(iBu) | H |
| 251 | S(O)$_2$Me | 6-OMe | — | H | H | C(O)O(tBu) | H |
| 252 | S(O)$_2$Me | 6-OMe | — | H | H | C(O)OCH$_2$(cPr) | H |
| 253 | S(O)$_2$Me | 6-OMe | — | H | H | C(O)O(CH$_2$)$_2$F | H |
| 254 | S(O)$_2$Me | 6-OMe | — | H | H | C(O)OBn | H |
| 255 | S(O)$_2$Me | 6-OMe | — | H | H | C(O)OCH$_2$CHF$_2$ | H |
| 256 | S(O)$_2$Me | 6-OMe | — | H | H | C(O)OCH$_2$CF$_3$ | H |
| 257 | S(O)$_2$Me | 6-OMe | — | H | H | C(O)(iBu) | H |
| 258 | S(O)$_2$Me | 7-OMe | — | H | H | C(O)O(iPr) | H |
| 259 | S(O)$_2$Me | 7-OMe | — | H | H | C(O)O(tBu) | H |
| 260 | S(O)$_2$Me | 4-OMe | — | H | H | C(O)O(iPr) | H |
| 261 | S(O)$_2$Me | 4-OMe | — | H | H | C(O)O(tBu) | H |
| 262 | S(O)$_2$Me | — | — | H | OMe | C(O)O(iPr) | H |
| 263 | S(O)$_2$Me | — | — | H | OMe | C(O)O(iBu) | H |
| 264 | S(O)$_2$Me | — | — | H | OMe | C(O)O(tBu) | H |
| 265 | S(O)$_2$Me | — | — | H | OMe | C(O)O(1-Me-Pr) | H |
| 266 | S(O)$_2$Me | — | — | H | OMe | C(O)OCH$_2$(2-Fur) | H |
| 267 | S(O)$_2$Me | — | — | H | OMe | C(O)OCH$_2$(cPr) | H |
| 268 | S(O)$_2$Me | — | — | H | OMe | C(O)OCH$_2$(cBu) | H |
| 269 | S(O)$_2$Me | — | — | H | OMe | C(O)OCH(Me)(cPr) | H |
| 270 | S(O)$_2$Me | — | — | H | OMe | C(O)O(CH$_2$)$_2$F | H |
| 271 | S(O)$_2$Me | — | — | H | OMe | C(O)OBn | H |
| 272 | S(O)$_2$Me | — | — | H | OMe | C(O)OCH$_2$CHF$_2$ | H |
| 273 | S(O)$_2$Me | — | — | H | OMe | C(O)OCH$_2$CF$_3$ | H |
| 274 | S(O)$_2$Me | — | — | H | OMe | C(O)(iBu) | H |
| 275 | S(O)$_2$Me | — | — | H | OEt | C(O)O(iPr) | H |
| 276 | S(O)$_2$Me | — | — | H | OEt | C(O)O(iBu) | H |
| 277 | S(O)$_2$Me | — | — | H | OEt | C(O)O(tBu) | H |
| 278 | S(O)$_2$Me | — | — | H | OEt | C(O)OCH$_2$(cPr) | H |
| 279 | S(O)$_2$Me | — | — | H | OEt | C(O)O(CH$_2$)$_2$F | H |
| 280 | S(O)$_2$Me | — | — | H | OEt | C(O)OBn | H |
| 281 | S(O)$_2$Me | — | — | H | OEt | C(O)OCH$_2$CHF$_2$ | H |
| 282 | S(O)$_2$Me | — | — | H | OEt | C(O)OCH$_2$CF$_3$ | H |
| 283 | S(O)$_2$Me | — | — | H | OEt | C(O)(iBu) | H |
| 284 | S(O)$_2$Me | — | — | H | O(iPr) | C(O)O(iPr) | H |
| 285 | S(O)$_2$Me | — | — | H | O(iPr) | C(O)O(iBu) | H |
| 286 | S(O)$_2$Me | — | — | H | O(iPr) | C(O)O(tBu) | H |
| 287 | S(O)$_2$Me | — | — | H | O(iPr) | C(O)OCH$_2$(cPr) | H |
| 288 | S(O)$_2$Me | — | — | H | O(iPr) | C(O)O(CH$_2$)$_2$F | H |
| 289 | S(O)$_2$Me | — | — | H | O(iPr) | C(O)OBn | H |
| 290 | S(O)$_2$Me | — | — | H | O(iPr) | C(O)OCH$_2$CHF$_2$ | H |
| 291 | S(O)$_2$Me | — | — | H | O(iPr) | C(O)OCH$_2$CF$_3$ | H |
| 292 | S(O)$_2$Me | — | — | H | O(iPr) | C(O)(iBu) | H |
| 293 | S(O)$_2$Me | — | — | H | O(cPr) | C(O)O(iPr) | H |
| 294 | S(O)$_2$Me | — | — | H | O(cPr) | C(O)O(tBu) | H |
| 295 | S(O)$_2$Me | — | — | H | H | C(O)O(iPr) | 2-Me |
| 296 | S(O)$_2$Me | — | — | H | H | C(O)O(tBu) | 2-Me |
| 297 | S(O)$_2$Me | — | — | H | H | C(O)OCH$_2$(cPr) | 2-Me |

TABLE 1-continued

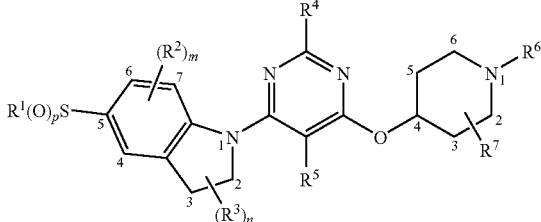

| No. | S(O)$_p$R$^1$ | R$^2$ | R$^3$ | R$^4$ | R$^5$ | R$^6$ | R$^7$ |
|---|---|---|---|---|---|---|---|
| 298 | S(O)$_2$Me | — | — | H | H | C(O)O(CH$_2$)$_2$F | 2-Me |
| 299 | S(O)$_2$Me | — | — | H | H | C(O)OBn | 2-Me |
| 300 | S(O)$_2$Me | — | — | H | H | C(O)OCH$_2$CF$_3$ | 2-Me |
| 301 | S(O)$_2$Me | — | — | H | H | C(O)(iBu) | 2-Me |
| 302 | S(O)$_2$Et | — | — | H | H | C(O)OMe | H |
| 303 | S(O)$_2$Et | — | — | H | H | C(O)OEt | H |
| 304 | S(O)$_2$Et | — | — | H | H | C(O)OPr | H |
| 305 | S(O)$_2$Et | — | — | H | H | C(O)O(iPr) | H |
| 306 | S(O)$_2$Et | — | — | H | H | C(O)OBu | H |
| 307 | S(O)$_2$Et | — | — | H | H | C(O)O(iBu) | H |
| 308 | S(O)$_2$Et | — | — | H | H | C(O)O(sBu) | H |
| 309 | S(O)$_2$Et | — | — | H | H | C(O)O(tBu) | H |
| 310 | S(O)$_2$Et | — | — | H | H | C(O)O(cBu) | H |
| 311 | S(O)$_2$Et | — | — | H | H | C(O)OPn | H |
| 312 | S(O)$_2$Et | — | — | H | H | C(O)O(cPn) | H |
| 313 | S(O)$_2$Et | — | — | H | H | C(O)OCH$_2$(cPr) | H |
| 314 | S(O)$_2$Et | — | — | H | H | C(O)OCH$_2$(cBu) | H |
| 315 | S(O)$_2$Et | — | — | H | H | C(O)OCH$_2$(3-Fur) | H |
| 316 | S(O)$_2$Et | — | — | H | H | C(O)OCH$_2$(cPn) | H |
| 317 | S(O)$_2$Et | — | — | H | H | C(O)O(CH$_2$)$_2$F | H |
| 318 | S(O)$_2$Et | — | — | H | H | C(O)OPh | H |
| 319 | S(O)$_2$Et | — | — | H | H | C(O)O(4-F-Ph) | H |
| 320 | S(O)$_2$Et | — | — | H | H | C(O)O(4-OMe-Ph) | H |
| 321 | S(O)$_2$Et | — | — | H | H | C(O)OBn | H |
| 322 | S(O)$_2$Et | — | — | H | H | C(O)O(4-F-Bn) | H |
| 323 | S(O)$_2$Et | — | — | H | H | C(O)O(4-OMe-Bn) | H |
| 324 | S(O)$_2$Et | — | — | H | H | C(O)O(1-Me-Bn) | H |
| 325 | S(O)$_2$Et | — | — | H | H | C(O)OCH$_2$CHF$_2$ | H |
| 326 | S(O)$_2$Et | — | — | H | H | C(O)OCH$_2$CF$_3$ | H |
| 327 | S(O)$_2$Et | — | — | H | H | C(O)OCH(CH$_2$F)$_2$ | H |
| 328 | S(O)$_2$Et | — | — | H | H | C(O)(iBu) | H |
| 329 | S(O)$_2$Et | — | — | H | H | C(O)(CH$_2$)$_2$CF$_3$ | H |
| 330 | S(O)$_2$Et | — | — | H | H | C(O)(CH$_2$)$_2$(cPr) | H |
| 331 | S(O)$_2$Et | — | — | H | H | C(O)Ph | H |
| 332 | S(O)$_2$Et | — | — | H | H | C(O)(4-F-Ph) | H |
| 333 | S(O)$_2$Et | — | — | H | H | C(O)(4-OMe-Ph) | H |
| 334 | S(O)$_2$Et | — | — | H | H | C(O)Bn | H |
| 335 | S(O)$_2$Et | — | — | H | H | C(O)CH$_2$(4-F-Ph) | H |
| 336 | S(O)$_2$Et | — | — | H | H | C(O)CH$_2$(4-OMe-Ph) | H |
| 337 | S(O)$_2$Et | — | — | H | H | C(O)(CH$_2$)$_2$Ph | H |
| 338 | S(O)$_2$Et | — | — | H | H | C(O)(CH$_2$)$_2$(4-F-Ph) | H |
| 339 | S(O)$_2$Et | — | — | H | H | C(O)(CH$_2$)$_2$(4-OMe-Ph) | H |
| 340 | S(O)$_2$Et | — | — | H | Me | C(O)O(iPr) | H |
| 341 | S(O)$_2$Et | — | — | H | Me | C(O)O(tBu) | H |
| 342 | S(O)$_2$Et | — | — | H | Me | C(O)OCH$_2$(cPr) | H |
| 343 | S(O)$_2$Et | — | — | H | Me | C(O)O(CH$_2$)$_2$F | H |
| 344 | S(O)$_2$Et | — | — | H | Me | C(O)OBn | H |
| 345 | S(O)$_2$Et | — | — | H | Me | C(O)OCH$_2$CF$_3$ | H |
| 346 | S(O)$_2$Et | — | — | H | Me | C(O)(iBu) | H |
| 347 | S(O)$_2$Et | — | — | H | OMe | C(O)O(iPr) | H |
| 348 | S(O)$_2$Et | — | — | H | OMe | C(O)O(tBu) | H |
| 349 | S(O)$_2$Et | — | — | H | OMe | C(O)OCH$_2$(cPr) | H |
| 350 | S(O)$_2$Et | — | — | H | OMe | C(O)O(CH$_2$)$_2$F | H |
| 351 | S(O)$_2$Et | — | — | H | OMe | C(O)OBn | H |
| 352 | S(O)$_2$Et | — | — | H | OMe | C(O)OCH$_2$CF$_3$ | H |
| 352 | S(O)$_2$Et | — | — | H | OMe | C(O)(iBu) | H |
| 353 | S(O)$_2$(CH$_2$)$_2$F | — | — | H | H | C(O)O(iPr) | H |
| 354 | S(O)$_2$(CH$_2$)$_2$F | — | — | H | H | C(O)O(iBu) | H |
| 355 | S(O)$_2$(CH$_2$)$_2$F | — | — | H | H | C(O)O(tBu) | H |
| 356 | S(O)$_2$(CH$_2$)$_2$F | — | — | H | H | C(O)OCH$_2$(cPr) | H |
| 357 | S(O)$_2$(CH$_2$)$_2$F | — | — | H | H | C(O)O(CH$_2$)$_2$F | H |
| 358 | S(O)$_2$(CH$_2$)$_2$F | — | — | H | H | C(O)OBn | H |
| 359 | S(O)$_2$(CH$_2$)$_2$F | — | — | H | H | C(O)OCH$_2$CHF$_2$ | H |
| 360 | S(O)$_2$(CH$_2$)$_2$F | — | — | H | H | C(O)OCH$_2$CF$_3$ | H |
| 361 | S(O)$_2$(CH$_2$)$_2$F | — | — | H | H | C(O)(iBu) | H |

TABLE 1-continued

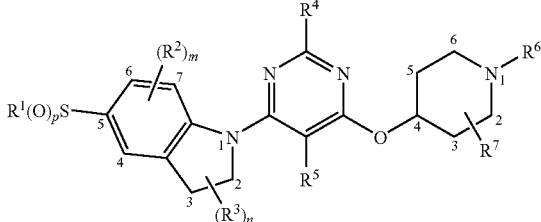

| No. | $S(O)_pR^1$ | $R^2$ | $R^3$ | $R^4$ | $R^5$ | $R^6$ | $R^7$ |
|---|---|---|---|---|---|---|---|
| 362 | $S(O)_2(CH_2)_2Cl$ | — | — | H | H | $C(O)O(iPr)$ | H |
| 363 | $S(O)_2(CH_2)_2Cl$ | — | — | H | H | $C(O)O(iBu)$ | H |
| 364 | $S(O)_2(CH_2)_2Cl$ | — | — | H | H | $C(O)O(tBu)$ | H |
| 365 | $S(O)_2(CH_2)_2Cl$ | — | — | H | H | $C(O)OCH_2(cPr)$ | H |
| 366 | $S(O)_2(CH_2)_2Cl$ | — | — | H | H | $C(O)O(CH_2)_2F$ | H |
| 367 | $S(O)_2(CH_2)_2Cl$ | — | — | H | H | $C(O)OBn$ | H |
| 368 | $S(O)_2(CH_2)_2Cl$ | — | — | H | H | $C(O)OCH_2CHF_2$ | H |
| 369 | $S(O)_2(CH_2)_2Cl$ | — | — | H | H | $C(O)OCH_2CF_3$ | H |
| 370 | $S(O)_2(CH_2)_2Cl$ | — | — | H | H | $C(O)(iBu)$ | H |
| 371 | $S(O)_2(CH_2)_2OH$ | — | — | H | H | $C(O)O(iPr)$ | H |
| 372 | $S(O)_2(CH_2)_2OH$ | — | — | H | H | $C(O)O(iBu)$ | H |
| 373 | $S(O)_2(CH_2)_2OH$ | — | — | H | H | $C(O)O(tBu)$ | H |
| 374 | $S(O)_2(CH_2)_2OH$ | — | — | H | H | $C(O)OCH_2(cPr)$ | H |
| 375 | $S(O)_2(CH_2)_2OH$ | — | — | H | H | $C(O)O(CH_2)_2F$ | H |
| 376 | $S(O)_2(CH_2)_2OH$ | — | — | H | H | $C(O)OBn$ | H |
| 377 | $S(O)_2(CH_2)_2OH$ | — | — | H | H | $C(O)OCH_2CHF_2$ | H |
| 378 | $S(O)_2(CH_2)_2OH$ | — | — | H | H | $C(O)OCH_2CF_3$ | H |
| 379 | $S(O)_2(CH_2)_2OH$ | — | — | H | H | $C(O)(iBu)$ | H |
| 380 | $S(O)_2(CH_2)_2OMe$ | — | — | H | H | $C(O)O(iPr)$ | H |
| 381 | $S(O)_2(CH_2)_2OMe$ | — | — | H | H | $C(O)O(iBu)$ | H |
| 382 | $S(O)_2(CH_2)_2OMe$ | — | — | H | H | $C(O)O(tBu)$ | H |
| 383 | $S(O)_2(CH_2)_2OMe$ | — | — | H | H | $C(O)OCH_2(cPr)$ | H |
| 384 | $S(O)_2(CH_2)_2OMe$ | — | — | H | H | $C(O)O(CH_2)_2F$ | H |
| 385 | $S(O)_2(CH_2)_2OMe$ | — | — | H | H | $C(O)OBn$ | H |
| 386 | $S(O)_2(CH_2)_2OMe$ | — | — | H | H | $C(O)OCH_2CHF_2$ | H |
| 387 | $S(O)_2(CH_2)_2OMe$ | — | — | H | H | $C(O)OCH_2CF_3$ | H |
| 388 | $S(O)_2(CH_2)_2OMe$ | — | — | H | H | $C(O)(iBu)$ | H |
| 389 | $S(O)_2Pr$ | — | — | H | H | $C(O)O(iPr)$ | H |
| 390 | $S(O)_2Pr$ | — | — | H | H | $C(O)O(iBu)$ | H |
| 391 | $S(O)_2Pr$ | — | — | H | H | $C(O)O(tBu)$ | H |
| 392 | $S(O)_2Pr$ | — | — | H | H | $C(O)OCH_2(cPr)$ | H |
| 393 | $S(O)_2Pr$ | — | — | H | H | $C(O)O(CH_2)_2F$ | H |
| 394 | $S(O)_2Pr$ | — | — | H | H | $C(O)OBn$ | H |
| 395 | $S(O)_2Pr$ | — | — | H | H | $C(O)OCH_2CHF_2$ | H |
| 396 | $S(O)_2Pr$ | — | — | H | H | $C(O)OCH_2CF_3$ | H |
| 397 | $S(O)_2Pr$ | — | — | H | H | $C(O)O(iBu)$ | H |
| 398 | $S(O)_2Pr$ | — | — | H | Me | $C(O)O(iPr)$ | H |
| 399 | $S(O)_2Pr$ | — | — | H | Me | $C(O)O(tBu)$ | H |
| 400 | $S(O)_2Pr$ | — | — | H | Me | $C(O)OCH_2(cPr)$ | H |
| 401 | $S(O)_2Pr$ | — | — | H | Me | $C(O)O(CH_2)_2F$ | H |
| 402 | $S(O)_2Pr$ | — | — | H | Me | $C(O)OBn$ | H |
| 403 | $S(O)_2Pr$ | — | — | H | Me | $C(O)OCH_2CF_3$ | H |
| 404 | $S(O)_2Pr$ | — | — | H | Me | $C(O)(iBu)$ | H |
| 405 | $S(O)_2Pr$ | — | — | H | OMe | $C(O)O(iPr)$ | H |
| 406 | $S(O)_2Pr$ | — | — | H | OMe | $C(O)O(tBu)$ | H |
| 407 | $S(O)_2Pr$ | — | — | H | OMe | $C(O)OCH_2(cPr)$ | H |
| 408 | $S(O)_2Pr$ | — | — | H | OMe | $C(O)O(CH_2)_2F$ | H |
| 409 | $S(O)_2Pr$ | — | — | H | OMe | $C(O)OBn$ | H |
| 410 | $S(O)_2Pr$ | — | — | H | OMe | $C(O)OCH_2CF_3$ | H |
| 411 | $S(O)_2Pr$ | — | — | H | OMe | $C(O)(iBu)$ | H |
| 412 | $S(O)_2(iPr)$ | — | — | H | H | $C(O)O(iPr)$ | H |
| 413 | $S(O)_2(iPr)$ | — | — | H | H | $C(O)O(iBu)$ | H |
| 414 | $S(O)_2(iPr)$ | — | — | H | H | $C(O)O(tBu)$ | H |
| 415 | $S(O)_2(iPr)$ | — | — | H | H | $C(O)OCH_2(cPr)$ | H |
| 416 | $S(O)_2(iPr)$ | — | — | H | H | $C(O)O(CH_2)_2F$ | H |
| 417 | $S(O)_2(iPr)$ | — | — | H | H | $C(O)OBn$ | H |
| 418 | $S(O)_2(iPr)$ | — | — | H | H | $C(O)OCH_2CHF_3$ | H |
| 419 | $S(O)_2(iPr)$ | — | — | H | H | $C(O)OCH_2CF_3$ | H |
| 420 | $S(O)_2(iPr)$ | — | — | H | H | $C(O)(iBu)$ | H |
| 421 | $S(O)_2(iPr)$ | — | — | H | Me | $C(O)O(iPr)$ | H |
| 422 | $S(O)_2(iPr)$ | — | — | H | Me | $C(O)O(tBu)$ | H |
| 423 | $S(O)_2(iPr)$ | — | — | H | Me | $C(O)OCH_2(cPr)$ | H |
| 424 | $S(O)_2(iPr)$ | — | — | H | Me | $C(O)O(CH_2)_2F$ | H |
| 425 | $S(O)_2(iPr)$ | — | — | H | Me | $C(O)OBn$ | H |
| 426 | $S(O)_2(iPr)$ | — | — | H | Me | $C(O)OCH_2CF_3$ | H |

TABLE 1-continued

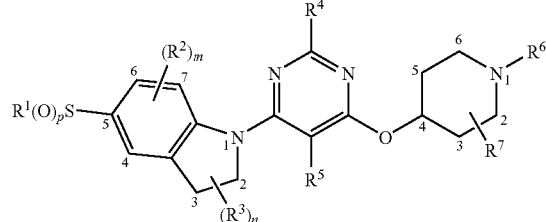

| No. | $S(O)_pR^1$ | $R^2$ | $R^3$ | $R^4$ | $R^5$ | $R^6$ | $R^7$ |
|---|---|---|---|---|---|---|---|
| 427 | $S(O)_2(iPr)$ | — | — | H | Me | C(O)(iBu) | H |
| 428 | $S(O)_2(iPr)$ | — | — | H | OMe | C(O)O(iPr) | H |
| 429 | $S(O)_2(iPr)$ | — | — | H | OMe | C(O)O(tBu) | H |
| 430 | $S(O)_2(iPr)$ | — | — | H | OMe | $C(O)OCH_2(cPr)$ | H |
| 431 | $S(O)_2(iPr)$ | — | — | H | OMe | $C(O)O(CH_2)_2F$ | H |
| 432 | $S(O)_2(iPr)$ | — | — | H | OMe | C(O)OBn | H |
| 433 | $S(O)_2(iPr)$ | — | — | H | OMe | $C(O)OCH_2CF_3$ | H |
| 434 | $S(O)_2(iPr)$ | — | — | H | OMe | C(O)(iBu) | H |
| 435 | $S(O)_2(cPr)$ | — | — | H | H | C(O)O(iPr) | H |
| 436 | $S(O)_2(cPr)$ | — | — | H | H | C(O)(iBu) | H |
| 437 | $S(O)_2(cPr)$ | — | — | H | H | C(O)O(tBu) | H |
| 438 | $S(O)_2(cPr)$ | — | — | H | H | $C(O)OCH_2(cPr)$ | H |
| 439 | $S(O)_2(cPr)$ | — | — | H | H | $C(O)O(CH_2)_2F$ | H |
| 440 | $S(O)_2(cPr)$ | — | — | H | H | C(O)OBn | H |
| 441 | $S(O)_2(cPr)$ | — | — | H | H | $C(O)OCH_2CHF_2$ | H |
| 442 | $S(O)_2(cPr)$ | — | — | H | H | $C(O)OCH_2CF_3$ | H |
| 443 | $S(O)_2(cPr)$ | — | — | H | H | C(O)(iBu) | H |
| 444 | $S(O)_2(cPr)$ | — | — | H | Me | C(O)O(iPr) | H |
| 445 | $S(O)_2(cPr)$ | — | — | H | Me | C(O)O(tBu) | H |
| 446 | $S(O)_2(cPr)$ | — | — | H | Me | $C(O)OCH_2(cPr)$ | H |
| 447 | $S(O)_2(cPr)$ | — | — | H | Me | $C(O)O(CH_2)_2F$ | H |
| 448 | $S(O)_2(cPr)$ | — | — | H | Me | C(O)OBn | H |
| 449 | $S(O)_2(cPr)$ | — | — | H | Me | $C(O)OCH_2CF_3$ | H |
| 450 | $S(O)_2(cPr)$ | — | — | H | Me | C(O)(iBu) | H |
| 451 | $S(O)_2(cPr)$ | — | — | H | OMe | C(O)O(iPr) | H |
| 452 | $S(O)_2(cPr)$ | — | — | H | OMe | C(O)O(tBu) | H |
| 453 | $S(O)_2(cPr)$ | — | — | H | OMe | $C(O)OCH_2(cPr)$ | H |
| 454 | $S(O)_2(cPr)$ | — | — | H | OMe | $C(O)O(CH_2)_2F$ | H |
| 455 | $S(O)_2(cPr)$ | — | — | H | OMe | C(O)OBn | H |
| 456 | $S(O)_2(cPr)$ | — | — | H | OMe | $C(O)OCH_2CF_3$ | H |
| 457 | $S(O)_2(cPr)$ | — | — | H | OMe | C(O)(iBu) | H |
| 458 | $S(O)_2Bu$ | — | — | H | H | C(O)O(iPr) | H |
| 459 | $S(O)_2Bu$ | — | — | H | H | C(O)O(tBu) | H |
| 460 | $S(O)_2Bu$ | — | — | H | H | $C(O)OCH_2(cPr)$ | H |
| 461 | $S(O)_2Bu$ | — | — | H | H | $C(O)O(CH_2)_2F$ | H |
| 462 | $S(O)_2Bu$ | — | — | H | H | C(O)OBn | H |
| 463 | $S(O)_2Bu$ | — | — | H | H | $C(O)OCH_2CF_3$ | H |
| 464 | $S(O)_2Bu$ | — | — | H | H | C(O)(iBu) | H |
| 465 | $S(O)_2Bu$ | — | — | H | Me | C(O)O(iPr) | H |
| 466 | $S(O)_2Bu$ | — | — | H | Me | C(O)O(tBu) | H |
| 467 | $S(O)_2Bu$ | — | — | H | Me | $C(O)OCH_2(cPr)$ | H |
| 468 | $S(O)_2Bu$ | — | — | H | Me | $C(O)O(CH_2)_2F$ | H |
| 469 | $S(O)_2Bu$ | — | — | H | Me | C(O)OBn | H |
| 470 | $S(O)_2Bu$ | — | — | H | Me | $C(O)OCH_2CF_3$ | H |
| 471 | $S(O)_2Bu$ | — | — | H | Me | C(O)(iBu) | H |
| 472 | $S(O)_2Bu$ | — | — | H | OMe | C(O)O(iPr) | H |
| 473 | $S(O)_2Bu$ | — | — | H | OMe | C(O)O(tBu) | H |
| 474 | $S(O)_2Bu$ | — | — | H | OMe | $C(O)OCH_2(cPr)$ | H |
| 475 | $S(O)_2Bu$ | — | — | H | OMe | $C(O)O(CH_2)_2F$ | H |
| 476 | $S(O)_2Bu$ | — | — | H | OMe | C(O)OBn | H |
| 477 | $S(O)_2Bu$ | — | — | H | OMe | $C(O)OCH_2CF_3$ | H |
| 478 | $S(O)_2Bu$ | — | — | H | OMe | C(O)(iBu) | H |
| 479 | $S(O)_2(iBu)$ | — | — | H | H | C(O)O(iPr) | H |
| 480 | $S(O)_2(iBu)$ | — | — | H | H | C(O)(iBu) | H |
| 481 | $S(O)_2(iBu)$ | — | — | H | H | C(O)O(tBu) | H |
| 482 | $S(O)_2(iBu)$ | — | — | H | H | $C(O)OCH_2(cPr)$ | H |
| 483 | $S(O)_2(iBu)$ | — | — | H | H | $C(O)O(CH_2)_2F$ | H |
| 484 | $S(O)_2(iBu)$ | — | — | H | H | C(O)OBn | H |
| 485 | $S(O)_2(iBu)$ | — | — | H | H | $C(O)OCH_2CHF_2$ | H |
| 486 | $S(O)_2(iBu)$ | — | — | H | H | $C(O)OCH_2CF_3$ | H |
| 487 | $S(O)_2(iBu)$ | — | — | H | H | C(O)(iBu) | H |
| 488 | $S(O)_2(iBu)$ | — | — | H | Me | C(O)O(iPr) | H |
| 489 | $S(O)_2(iBu)$ | — | — | H | Me | C(O)O(tBu) | H |
| 490 | $S(O)_2(iBu)$ | — | — | H | Me | $C(O)OCH_2(cPr)$ | H |
| 491 | $S(O)_2(iBu)$ | — | — | H | Me | $C(O)O(CH_2)_2F$ | H |

TABLE 1-continued (I)

| No. | S(O)$_p$R$^1$ | R$^2$ | R$^3$ | R$^4$ | R$^5$ | R$^6$ | R$^7$ |
|---|---|---|---|---|---|---|---|
| 492 | S(O)$_2$(iBu) | — | — | H | Me | C(O)OBn | H |
| 493 | S(O)$_2$(iBu) | — | — | H | Me | C(O)OCH$_2$CF$_3$ | H |
| 494 | S(O)$_2$(iBu) | — | — | H | Me | C(O)(iBu) | H |
| 495 | S(O)$_2$(iBu) | — | — | H | OMe | C(O)O(iPr) | H |
| 496 | S(O)$_2$(iBu) | — | — | H | OMe | C(O)O(tBu) | H |
| 497 | S(O)$_2$(iBu) | — | — | H | OMe | C(O)OCH$_2$(cPr) | H |
| 498 | S(O)$_2$(iBu) | — | — | H | OMe | C(O)O(CH$_2$)$_2$F | H |
| 499 | S(O)$_2$(iBu) | — | — | H | OMe | C(O)OBn | H |
| 500 | S(O)$_2$(iBu) | — | — | H | OMe | C(O)OCH$_2$CF$_3$ | H |
| 501 | S(O)$_2$(iBu) | — | — | H | OMe | C(O)(iBu) | H |
| 502 | S(O)$_2$(cBu) | — | — | H | H | C(O)O(iPr) | H |
| 503 | S(O)$_2$(cBu) | — | — | H | H | C(O)O(tBu) | H |
| 504 | S(O)$_2$(cBu) | — | — | H | H | C(O)OCH$_2$(cPr) | H |
| 505 | S(O)$_2$(cBu) | — | — | H | H | C(O)O(CH$_2$)$_2$F | H |
| 506 | S(O)$_2$(cBu) | — | — | H | H | C(O)OBn | H |
| 507 | S(O)$_2$(cBu) | — | — | H | H | C(O)OCH$_2$CF$_3$ | H |
| 508 | S(O)$_2$(cBu) | — | — | H | H | C(O)(iBu) | H |
| 509 | S(O)$_2$(cBu) | — | — | H | Me | C(O)O(i-Pr) | H |
| 510 | S(O)$_2$(cBu) | — | — | H | Me | C(O)O(t-Bu) | H |
| 511 | S(O)$_2$(cBu) | — | — | H | Me | C(O)OCH$_2$(c-Pr) | H |
| 512 | S(O)$_2$(cBu) | — | — | H | Me | C(O)O(CH$_2$)$_2$F | H |
| 513 | S(O)$_2$(cBu) | — | — | H | Me | C(O)OBn | H |
| 514 | S(O)$_2$(cBu) | — | — | H | Me | C(O)OCH$_2$CF$_3$ | H |
| 515 | S(O)$_2$(cBu) | — | — | H | Me | C(O)(i-Bu) | H |
| 516 | S(O)$_2$(cBu) | — | — | H | OMe | C(O)O(iPr) | H |
| 517 | S(O)$_2$(cBu) | — | — | H | OMe | C(O)O(tBu) | H |
| 518 | S(O)$_2$(cBu) | — | — | H | OMe | C(O)OCH$_2$(cPr) | H |
| 519 | S(O)$_2$(cBu) | — | — | H | OMe | C(O)O(CH$_2$)$_2$F | H |
| 520 | S(O)$_2$(cBu) | — | — | H | OMe | C(O)OBn | H |
| 521 | S(O)$_2$(cBu) | — | — | H | OMe | C(O)OCH$_2$CF$_3$ | H |
| 522 | S(O)$_2$(cBu) | — | — | H | OMe | C(O)(iBu) | H |
| 523 | S(O)$_2$Pn | — | — | H | H | C(O)O(iPr) | H |
| 524 | S(O)$_2$Pn | — | — | H | H | C(O)O(tBu) | H |
| 525 | S(O)$_2$(cPn) | — | — | H | H | C(O)O(iPr) | H |
| 526 | S(O)$_2$(cPn) | — | — | H | H | C(O)O(tBu) | H |
| 527 | S(O)$_2$Hx | — | — | H | H | C(O)O(iPr) | H |
| 528 | S(O)$_2$Hx | — | — | H | H | C(O)O(tBu) | H |
| 529 | S(O)$_2$(cHx) | — | — | H | H | C(O)O(iPr) | H |
| 530 | S(O)$_2$(cHx) | — | — | H | H | C(O)O(tBu) | H |
| 531 | S(O)$_2$(Aly) | — | — | H | H | C(O)O(iPr) | H |
| 532 | S(O)$_2$(Aly) | — | — | H | H | C(O)O(tBu) | H |
| 533 | S(O)$_2$CH$_2$(Ety) | — | — | H | H | C(O)O(iPr) | H |
| 534 | S(O)$_2$CH$_2$(Ety) | — | — | H | H | C(O)O(tBu) | H |
| 535 | S(O)$_2$CH$_2$(cPr) | — | — | H | H | C(O)O(iBu) | H |
| 536 | S(O)$_2$CH$_2$(cPr) | — | — | H | H | C(O)O(iPr) | H |
| 537 | S(O)$_2$CH$_2$(cPr) | — | — | H | H | C(O)O(tBu) | H |
| 538 | S(O)$_2$CH$_2$(cPr) | — | — | H | H | C(O)OCH$_2$(cPr) | H |
| 539 | S(O)$_2$CH$_2$(cPr) | — | — | H | H | C(O)O(CH$_2$)$_2$F | H |
| 540 | S(O)$_2$CH$_2$(cPr) | — | — | H | H | C(O)OBn | H |
| 541 | S(O)$_2$CH$_2$(cPr) | — | — | H | H | C(O)OCH$_2$CHF$_2$ | H |
| 542 | S(0)2CH2(cPr) | — | — | H | H | C(O)OCH$_2$CF$_3$ | H |
| 543 | S(O)$_2$CH$_2$(cPr) | — | — | H | H | C(O)(iBu) | H |
| 544 | S(O)$_2$CH$_2$(cPr) | — | — | H | Me | C(O)O(iPr) | H |
| 545 | S(O)$_2$CH$_2$(cPr) | — | — | H | Me | C(O)O(tBu) | H |
| 546 | S(O)$_2$CH$_2$(cPr) | — | — | H | Me | C(O)OCH$_2$(cPr) | H |
| 547 | S(O)$_2$CH$_2$(cPr) | — | — | H | Me | C(O)O(CH$_2$)$_2$F | H |
| 548 | S(O)$_2$CH$_2$(cPr) | — | — | H | Me | C(O)OBn | H |
| 549 | S(O)$_2$CH$_2$(cPr) | — | — | H | Me | C(O)OCH$_2$CF$_3$ | H |
| 550 | S(O)$_2$CH$_2$(cPr) | — | — | H | Me | C(O)(iBu) | H |
| 551 | S(O)$_2$CH$_2$(cPr) | — | — | H | OMe | C(O)O(iPr) | H |
| 552 | S(O)$_2$CH$_2$(cPr) | — | — | H | OMe | C(O)O(tBu) | H |
| 553 | S(O)$_2$CH$_2$(cPr) | — | — | H | OMe | C(O)OCH$_2$(cPr) | H |
| 554 | S(O)$_2$CH$_2$(cPr) | — | — | H | OMe | C(O)O(CH$_2$)$_2$F | H |
| 555 | S(O)$_2$CH$_2$(cPr) | — | — | H | OMe | C(O)OBn | H |
| 556 | S(O)$_2$CH$_2$(cPr) | — | — | H | OMe | C(O)OCH$_2$CF$_3$ | H |

TABLE 1-continued (I)

| No. | S(O)$_p$R$^1$ | R$^2$ | R$^3$ | R$^4$ | R$^5$ | R$^6$ | R$^7$ |
|---|---|---|---|---|---|---|---|
| 557 | S(O)$_2$CH$_2$(cPr) | — | — | H | OMe | C(O)(iBu) | H |
| 558 | S(O)$_2$CH$_2$(cBu) | — | — | H | H | C(O)O(tBu) | H |
| 559 | S(O)$_2$CH$_2$(cPn) | — | — | H | H | C(O)O(tBu) | H |
| 560 | S(O)$_2$NH$_2$ | — | — | H | H | C(O)O(iPr) | H |
| 561 | S(O)$_2$NH$_2$ | — | — | H | H | C(O)O(iBu) | H |
| 562 | S(O)$_2$NH$_2$ | — | — | H | H | C(O)O(tBu) | H |
| 563 | S(O)$_2$NH$_2$ | — | — | H | H | C(O)OCH$_2$(cPr) | H |
| 564 | S(O)$_2$NH$_2$ | — | — | H | H | C(O)O(CH$_2$)$_2$F | H |
| 565 | S(O)$_2$NH$_2$ | — | — | H | H | C(O)OBn | H |
| 566 | S(O)$_2$NH$_2$ | — | — | H | H | C(O)OCH$_2$CHF$_2$ | H |
| 567 | S(O)$_2$NH$_2$ | — | — | H | H | C(O)OCH$_2$CF$_3$ | H |
| 568 | S(O)$_2$NH$_2$ | — | — | H | H | C(O)(iBu) | H |
| 569 | S(O)$_2$NH$_2$ | — | — | H | Me | C(O)O(iPr) | H |
| 570 | S(O)$_2$NH$_2$ | — | — | H | Me | C(O)O(tBu) | H |
| 571 | S(O)$_2$NH$_2$ | — | — | H | Me | C(O)OCH$_2$(cPr) | H |
| 572 | S(O)$_2$NH$_2$ | — | — | H | Me | C(O)O(CH$_2$)$_2$F | H |
| 573 | S(O)$_2$NH$_2$ | — | — | H | Me | C(O)OBn | H |
| 574 | S(O)$_2$NH$_2$ | — | — | H | Me | C(O)OCH$_2$CF$_3$ | H |
| 575 | S(O)$_2$NH$_2$ | — | — | H | Me | C(O)(iBu) | H |
| 576 | S(O)$_2$NH$_2$ | — | — | H | OMe | C(O)O(iPr) | H |
| 577 | S(O)$_2$NH$_2$ | — | — | H | OMe | C(O)O(tBu) | H |
| 578 | S(O)$_2$NH$_2$ | — | — | H | OMe | C(O)OCH$_2$(cPr) | H |
| 579 | S(O)$_2$NH$_2$ | — | — | H | OMe | C(O)O(CH$_2$)$_2$F | H |
| 580 | S(O)$_2$NH$_2$ | — | — | H | OMe | C(O)OBn | H |
| 581 | S(O)$_2$NH$_2$ | — | — | H | OMe | C(O)OCH$_2$CF$_3$ | H |
| 582 | S(O)$_2$NH$_2$ | — | — | H | OMe | C(O)(iBu) | H |
| 583 | S(O)$_2$NHMe | — | — | H | H | C(O)O(iPr) | H |
| 584 | S(O)$_2$NHMe | — | — | H | H | C(O)O(tBu) | H |
| 585 | S(O)$_2$NHMe | — | — | H | H | C(O)OCH$_2$(cPr) | H |
| 586 | S(O)$_2$NHMe | — | — | H | H | C(O)O(CH$_2$)$_2$F | H |
| 587 | S(O)$_2$NHMe | — | — | H | H | C(O)OBn | H |
| 588 | S(O)$_2$NHMe | — | — | H | H | C(O)OCH$_2$CF$_3$ | H |
| 589 | S(O)$_2$NHMe | — | — | H | H | C(O)(iBu) | H |
| 590 | S(O)$_2$NHEt | — | — | H | H | C(O)O(iPr) | H |
| 591 | S(O)$_2$NHEt | — | — | H | H | C(O)O(tBu) | H |
| 592 | S(O)$_2$NHEt | — | — | H | H | C(O)OCH$_2$(cPr) | H |
| 593 | S(O)$_2$NHEt | — | — | H | H | C(O)O(CH$_2$)$_2$F | H |
| 594 | S(O)$_2$NHEt | — | — | H | H | C(O)OBn | H |
| 595 | S(O)$_2$NHEt | — | — | H | H | C(O)OCH$_2$CF$_3$ | H |
| 596 | S(O)$_2$NHEt | — | — | H | H | C(O)(iBu) | H |
| 597 | S(O)$_2$NHPr | — | — | H | H | C(O)O(tBu) | H |
| 598 | S(O)$_2$NH(iPr) | — | — | H | H | C(O)O(tBu) | H |
| 599 | S(O)$_2$NH(cPr) | — | — | H | H | C(O)O(tBu) | H |
| 600 | S(O)$_2$NHBu | — | — | H | H | C(O)O(tBu) | H |
| 601 | S(O)$_2$NH(iBu) | — | — | H | H | C(O)O(tBu) | H |
| 602 | S(O)$_2$NH(cBu) | — | — | H | H | C(O)O(tBu) | H |
| 603 | S(O)$_2$NHCH$_2$(cPr) | — | — | H | H | C(O)O(tBu) | H |
| 604 | S(O)$_2$NMe$_2$ | — | — | H | H | C(O)O(iPr) | H |
| 605 | S(O)$_2$NMe$_2$ | — | — | H | H | C(O)O(tBu) | H |
| 606 | S(O)$_2$NMe$_2$ | — | — | H | H | C(O)OCH$_2$(cPr) | H |
| 607 | S(O)$_2$NMe$_2$ | — | — | H | H | C(O)O(CH$_2$)$_2$F | H |
| 608 | S(O)$_2$NMe$_2$ | — | — | H | H | C(O)OBn | H |
| 609 | S(O)$_2$NMe$_2$ | — | — | H | H | C(O)OCH$_2$CF$_3$ | H |
| 610 | S(O)$_2$NMe$_2$ | — | — | H | H | C(O)(iBu) | H |
| 611 | S(O)$_2$NMeEt | — | — | H | H | C(O)O(iPr) | H |
| 612 | S(O)$_2$NMeEt | — | — | H | H | C(O)O(tBu) | H |
| 613 | S(O)$_2$NEt$_2$ | — | — | H | H | C(O)O(iPr) | H |
| 614 | S(O)$_2$NEt$_2$ | — | — | H | H | C(O)O(tBu) | H |
| 615 | S(O)Me | — | — | H | H | C(0)O(iPr) | H |
| 616 | S(O)Me | — | — | H | H | C(O)O(iBu) | H |
| 617 | S(O)Me | — | — | H | H | C(O)O(tBu) | H |
| 618 | S(O)Me | — | — | H | H | C(O)O(1-Me-Pr) | H |
| 619 | S(O)Me | — | — | H | H | C(O)OCH$_2$(2-Fur) | H |
| 620 | S(O)Me | — | — | H | H | C(O)OCH$_2$(cPr) | H |
| 621 | S(O)Me | — | — | H | H | C(O)OCH$_2$(cBu) | H |

TABLE 1-continued

Structure (I): indoline-pyrimidine-piperidine scaffold with substituents $R^1(O)_pS$- at position 5 of indoline, $(R^2)_m$, $(R^3)_n$, $R^4$, $R^5$, $R^6$ on piperidine N, and $R^7$ on piperidine ring.

| No. | $S(O)_pR^1$ | $R^2$ | $R^3$ | $R^4$ | $R^5$ | $R^6$ | $R^7$ |
|---|---|---|---|---|---|---|---|
| 622 | S(O)Me | — | — | H | H | C(O)OCHMe(cPr) | H |
| 623 | S(O)Me | — | — | H | H | C(O)O(CH$_2$)$_2$F | H |
| 624 | S(O)Me | — | — | H | H | C(O)OBn | H |
| 625 | S(O)Me | — | — | H | H | C(O)OCH$_2$CHF$_2$ | H |
| 626 | S(O)Me | — | — | H | H | C(O)OCH$_2$CF$_3$ | H |
| 627 | S(O)Me | — | — | H | H | C(O)(iBu) | H |
| 628 | S(O)Me | — | — | H | Me | C(O)O(iPr) | H |
| 629 | S(O)Me | — | — | H | Me | C(O)O(iBu) | H |
| 630 | S(O)Me | — | — | H | Me | C(O)O(tBu) | H |
| 631 | S(O)Me | — | — | H | Me | C(O)OCH$_2$(cPr) | H |
| 632 | S(O)Me | — | — | H | Me | C(O)O(CH$_2$)$_2$F | H |
| 633 | S(O)Me | — | — | H | Me | C(O)OBn | H |
| 634 | S(O)Me | — | — | H | Me | C(O)OCH$_2$CHF$_2$ | H |
| 635 | S(O)Me | — | — | H | Me | C(O)OCH$_2$CF$_3$ | H |
| 636 | S(O)Me | — | — | H | Me | C(O)(iBu) | H |
| 637 | S(O)Me | — | — | H | OMe | C(O)O(iPr) | H |
| 638 | S(O)Me | — | — | H | OMe | C(O)O(iBu) | H |
| 639 | S(O)Me | — | — | H | OMe | C(O)O(tBu) | H |
| 640 | S(O)Me | — | — | H | OMe | C(O)OCH$_2$(cPr) | H |
| 641 | S(O)Me | — | — | H | OMe | C(O)O(CH$_2$)$_2$F | H |
| 642 | S(O)Me | — | — | H | OMe | C(O)OBn | H |
| 643 | S(O)Me | — | — | H | OMe | C(O)OCH$_2$CHF$_2$ | H |
| 644 | S(O)Me | — | — | H | OMe | C(O)OCH$_2$CF$_3$ | H |
| 645 | S(O)Me | — | — | H | OMe | C(O)(iBu) | H |
| 646 | S(O)Et | — | — | H | H | C(O)O(iPr) | H |
| 647 | S(O)Et | — | — | H | H | C(O)O(tBu) | H |
| 648 | S(O)Et | — | — | H | H | C(O)OCH$_2$(cPr) | H |
| 649 | S(O)Et | — | — | H | H | C(O)O(CH$_2$)$_2$F | H |
| 650 | S(O)Et | — | — | H | H | C(O)OBn | H |
| 651 | S(O)Et | — | — | H | H | C(O)OCH$_2$CF$_3$ | H |
| 652 | S(O)Et | — | — | H | H | C(O)(iBu) | H |
| 653 | S(O)Pr | — | — | H | H | C(O)O(iPr) | H |
| 654 | S(O)Pr | — | — | H | H | C(O)O(tBu) | H |
| 655 | S(O)Bu | — | — | H | H | C(O)O(iPr) | H |
| 656 | S(O)Bu | — | — | H | H | C(O)O(tBu) | H |
| 657 | S(O)(iBu) | — | — | H | H | C(O)O(iPr) | H |
| 658 | S(O)(iBu) | — | — | H | H | C(O)O(tBu) | H |
| 659 | S(O)(Aly) | — | — | H | H | C(O)O(iPr) | H |
| 660 | S(O)(Aly) | — | — | H | H | C(O)O(tBu) | H |
| 661 | S(O)CH$_2$(Ety) | — | — | H | H | C(O)O(iPr) | H |
| 662 | S(O)CH$_2$(Ety) | — | — | H | H | C(O)O(tBu) | H |
| 663 | S(O)CH$_2$(cPr) | — | — | H | H | C(O)O(iPr) | H |
| 664 | S(O)CH$_2$(cPr) | — | — | H | H | C(O)O(tBu) | H |
| 665 | S(O)$_2$Me | — | — | H | H | C(O)O(iPr) | 3-F |

Among these exemplary compounds, the compound 4, 6, 8, 9, 11, 13, 19, 26, 28, 34, 53, 54, 69, 262, 264, 305, 307, 308, 310, 313, 325, 326, 355, 391, 396, 503, or 617 is preferable, and the compound 4, 8, 19, 34, 53, 54, 69, 262, 264, 305, 313, or 617 is more preferable.

The compound of the present invention represented by the general formula (I) can be produced by, for example, processes described later. In the production processes shown below, indoline intermediates, piperidine intermediates, and pyrimidine intermediates can be produced with reference to, for example, J. Med. Chem., 41, 1998, 1598-1612, Bioorg. Med. Chem. Lett., 2002, 12, 3105-3110, Chem. Pharm. Bull., 1993, 41, 529-538, J. Org. Chem., 53, (1988), 2047-2052, WO 2003/47586, and WO 2006/76243. Moreover, commercially available indoline derivatives, piperidine derivatives, and pyrimidine derivatives may be used respectively as these intermediates.

In the processes described later, $R^1$, $R^2$, $R^3$, $R^4$, $R^5$, $R^6$, $R^{6a}$, $R^{6b}$, $R^{6c}$, $R^7$, m, n, and p are as defined in the general formula (I); $R^{6'}$ is as defined in $R^6$ except for a —C(O)O-tert-butyl group; $R^a$ is a C1-C6 alkyl group which may have 1 to 3 substituents selected from substituent group β; Boc represents a tert-butoxycarbonyl group; and tBu represents a tert-butyl group.

In reaction in each step of the processes described later, a compound serving as a reactive substrate may have a group that inhibits the reaction of interest (e.g., an amino, hydroxyl, or carboxyl group). In such a case, introduction of protective groups to these groups and removal of the introduced protective groups may be performed as appropriate. These protective groups are not particularly limited as long as they are protective groups usually used. Examples thereof include protective groups described in, for example, T. H. Greene, P. G. Wuts, Protective Groups in Organic Synthesis. Third Edition, 1999, John Wiley & Sons, Inc. Reactions for the introduction of these protective groups and the removal of the protective groups can be performed according to standard methods such as methods described therein.

Solvents used in the reaction in each step of the processes described later are not particularly limited as long as they do not inhibit the reaction and dissolve the starting material to some extent. Examples thereof include: aliphatic hydrocarbons such as hexane, pentane, petroleum ether, and cyclohexane; aromatic hydrocarbons such as benzene, toluene, and xylene; halogenated hydrocarbons such as dichloromethane, chloroform, carbon tetrachloride, dichloroethane, chlorobenzene, and dichlorobenzene; ethers such as diethyl ether, diisopropyl ether, tetrahydrofuran, dioxane, dimethoxyethane, and diethylene glycol dimethyl ether; ketones such as acetone, methyl ethyl ketone, methyl isobutyl ketone, and cyclohexanone; esters such as ethyl acetate, propyl acetate, and butyl acetate; nitriles such as acetonitrile, propionitrile, butyronitrile, and isobutyronitrile; carboxylic acids such as acetic acid and propionic acid; alcohols such as methanol, ethanol, 1-propanol, 2-propanol, 1-butanol, 2-butanol, 2-methyl-1-propanol, and 2-methyl-2-propanol; amides such as formamide, dimethylformamide, dimethylacetamide, N-methyl-2-pyrrolidone, and hexamethylphosphorotriamide; sulfoxides such as dimethyl sulfoxide and sulfolane; water; and mixtures thereof.

In the reaction in each step of the processes described later, the reaction temperature differs depending on solvents, starting materials, reagents, etc., and the reaction time differs depending on solvents, starting materials, reagents, the reaction temperature, etc.

In the reaction in each step of the processes described later, the compound of interest of the step is isolated from the reaction mixture according to standard methods after completion of the reaction. The compound of interest is obtained, for example, by: (i) removing insoluble matter such as catalysts by filtration as appropriate; (ii) adding water and a water-immiscible solvent (e.g., dichloromethane, diethyl ether, or ethyl acetate) to the reaction mixture to extract the compound of interest; (iii) washing the organic layer with water and drying it using a drying agent such as anhydrous magnesium sulfate; and (iv) distilling off the solvent. The obtained compound of interest can be further purified according to need by standard methods, for example, recrystallization, reprecipitation, and silica gel column chromatography. Alternatively, the compound of interest of each step can also be used directly in the next reaction without being purified.

A process A will be described.

[Process A]

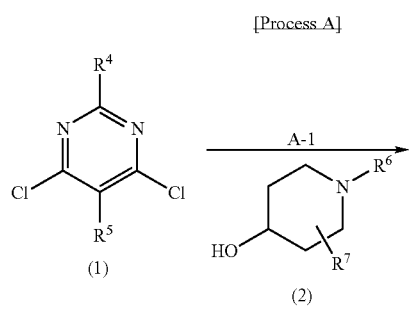

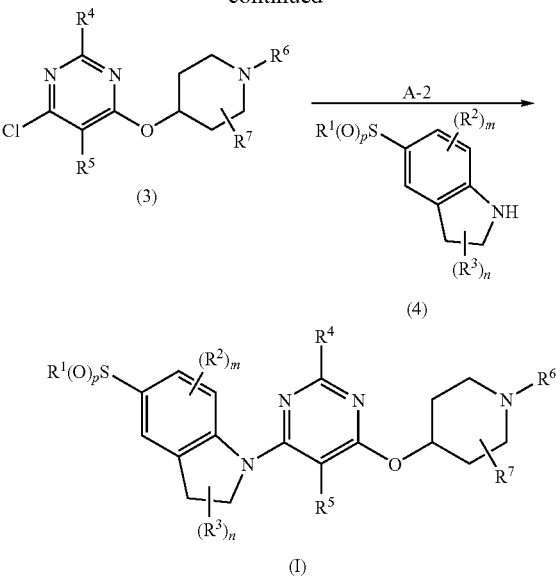

(Step A-1)

The step A-1 is a step of reacting a compound (1) with a compound (2) in the presence of a base to produce a compound (3).

Examples of the base used include sodium tert-butoxide, potassium tert-butoxide, sodium hydride, and potassium hydride. The base is preferably potassium tert-butoxide or sodium hydride, more preferably potassium tert-butoxide.

Examples of a solvent used include tetrahydrofuran, dioxane, cyclopentylmethyl ether, dimethylformamide, and dimethylacetamide. The solvent is preferably tetrahydrofuran or dimethylformamide, more preferably tetrahydrofuran.

The reaction temperature is 0 to 120° C., preferably 0 to 60° C. The reaction time is 10 minutes to 12 hours, preferably 30 minutes to 6 hours.

(Step A-2)

The step A-2 is a step of reacting the compound (3) obtained in the step A-1 with a compound (4) through Buchwald-Hartwig reaction using a palladium catalyst to produce the compound represented by the general formula (I).

The palladium catalyst, a ligand, a base, and reaction conditions used are not particularly limited as long as they are reagents or conditions usually used in Buchwald-Hartwig reaction. These reagents or conditions are described in, for example, A. R. Muci, S. L. Buchwald, Top. Curr. Chem. 2002, vol. 219, p. 131.

The palladium catalyst is preferably palladium (II) acetate or palladium (0) dibenzylideneacetone, more preferably palladium (II) acetate.

The ligand is preferably tricyclohexylphosphine, 1,3-bis(phenylphosphono)propane, 2,2'-bis(diphenylphosphanyl)-1,1'-binaphthyl, 2-(dicyclohexylphosphono)biphenyl, or 2-dicyclohexylphosphino-2'-(N,N-dimethylamino)biphenyl, more preferably 2-dicyclohexylphosphino-2'-(N,N-dimethylamino)biphenyl.

The base is preferably sodium carbonate, potassium carbonate, cesium carbonate, sodium tert-butoxide, or potassium tert-butoxide, more preferably potassium carbonate.

The solvent is preferably toluene or dioxane, more preferably 1,4-dioxane.

The reaction temperature is preferably 20 to 150° C. The reaction time is preferably 30 minutes to 12 hours.

The compound of the present invention represented by the general formula (I) wherein p is 2 can also be produced by the following process B:

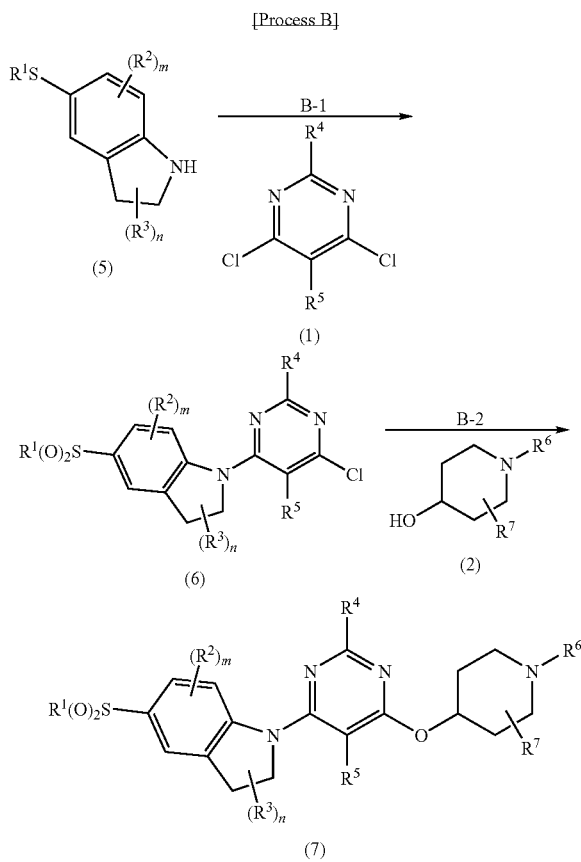

(Step B-1)

The step B-1 is a step of reacting a compound (5) with the compound (1) in the presence of an acid and then oxidizing the reaction product in the presence of an oxidizing agent to produce a compound (6).

Examples of the acid used include hydrochloric acid, hydrobromic acid, sulfuric acid, methanesulfonic acid, and trifluoromethanesulfonic acid. The acid is preferably concentrated hydrochloric acid.

Examples of the oxidizing agent used in the oxidation include aqueous hydrogen peroxide, peracetic acid, trifluoroperacetic acid, dimethyldioxirane, Oxone (trade name), m-chloroperbenzoic acid, magnesium bis(peroxyphthalate) tetrahydrate, potassium permanganate, and chromium (VI) oxide. The oxidizing agent is preferably m-chloroperbenzoic acid.

Examples of a solvent used in the reaction with the compound (1) include mixtures of acetone, methyl ethyl ketone, tetrahydrofuran, dioxane, or cyclopentylmethyl ether with water. The solvent is preferably a mixture of acetone with water.

Examples of a solvent used in the oxidation include dichloromethane, dichloroethane, and chloroform. The solvent is preferably dichloromethane.

In the reaction with the compound (1), the reaction temperature is 0 to 150° C., preferably 0 to 100° C. In the reaction with the compound (1), the reaction time is 15 minutes to 24 hours, preferably 30 minutes to 12 hours.

In the oxidation, the reaction temperature is −30 to 50° C., preferably −10 to 30° C. In the oxidation, the reaction time is 5 minutes to 10 hours, preferably 10 minutes to 5 hours.

(Step B-2)

The step B-2 is a step of reacting the compound (6) obtained in the step B-1 with the compound (2) in the presence of a base to produce a compound (7).

Examples of the base used include sodium hydride and potassium hydride. The base is preferably sodium hydride.

Examples of a solvent used include tetrahydrofuran, dioxane, dimethylformamide, and dimethylacetamide. The solvent is preferably tetrahydrofuran.

The reaction temperature is 0 to 120° C., preferably 0 to 80° C.

The reaction time is 10 minutes to 24 hours, preferably 30 minutes to 6 hours.

The compound of the present invention represented by the general formula (I) wherein $R^6$ is a group other than Boc can also be produced by the following process C using, as an intermediate, the compound of the present invention represented by the general formula (I) wherein $R^6$ is Boc:

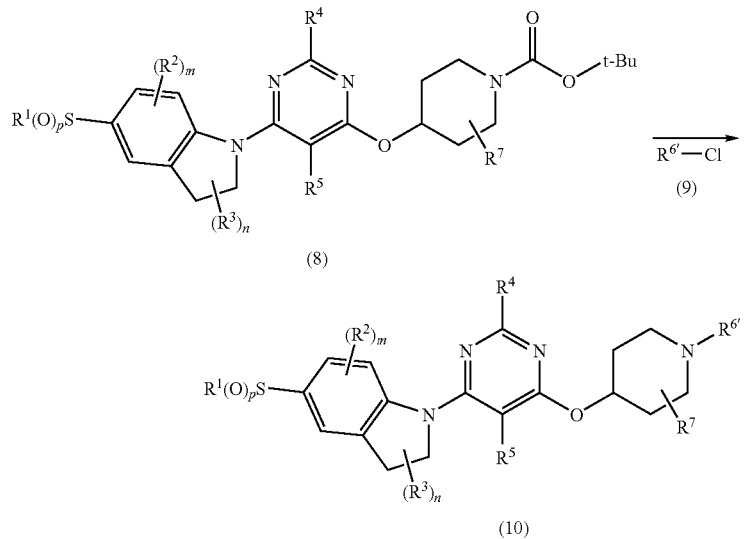

The process C is a process of removing the Boc group in a compound (8) and then reacting the resulting compound (8) with a compound (9) in the presence of a base to produce a compound (10).

Examples of a reagent used in the removal of the Boc group in the compound (8) include reagents capable of removing Boc groups, described in, for example, T. H. Greene, P. G. Wuts, Protective Groups in Organic Synthesis. Third Edition, 1999, John Wiley & Sons, Inc. The reagent is preferably trifluoroacetic acid or hydrochloric acid-ethyl acetate.

Examples of a solvent used in the removal of the Boc group include dichloromethane, chloroform, ethyl acetate, and dioxane. The solvent is preferably dichloromethane or ethyl acetate.

In the removal of the Boc group, the reaction temperature is 0 to 100° C., preferably 0 to 50° C.

In the removal of the Boc group, the reaction time is 5 minutes to 24 hours, preferably 10 minutes to 6 hours.

Examples of the base used include triethylamine, diisopropylethylamine, pyridine, 4-dimethylaminopyridine (DMAP), 2,6-lutidine, and 1,4-diazabicyclo[2.2.2]octane (DABCO). The base is preferably triethylamine or diisopropylethylamine, more preferably diisopropylethylamine.

Examples of a solvent used in the reaction with the compound (9) include dichloromethane, dichloroethane, chloroform, tetrahydrofuran, and toluene. The solvent is preferably dichloromethane or tetrahydrofuran, more preferably dichloromethane.

In the reaction with the compound (9), the reaction temperature is −30 to 100° C., preferably −20 to 50° C.

In the reaction with the compound (9), the reaction time is 5 minutes to 24 hours, preferably 10 minutes to 12 hours.

The removal of the Boc group can be performed in the same way as that in the process C.

The condensing agent used is not particularly limited as long as it can be used in amidation reaction. The condensing agent can be any of those described in, for example, R. C. Larock, Comprehensive Organic Transformations. Second Edition, 1999, John Wiley & Sons, Inc. Specific examples thereof include:

(i) combinations of phosphates (e.g., diethyl phosphoryl cyanide) with bases shown below;
(ii) carbodiimides such as 1,3-dicyclohexylcarbodiimide, 1,3-diisopropylcarbodiimide, and 1-ethyl-3-(3-dimethylaminopropyl)carbodiimide (WSC); combinations of these carbodiimides with bases shown below; and combinations of these carbodiimides with N-hydroxy compounds (e.g., N-hydroxysuccinimide);
(iii) imidazoles such as 1,1'-carbonyldiimidazole (CDI);
(iv) 4-(4,6-dimethoxy-1,3,5-triazin-2-yl)-4-methylmorpholinium chloride (DMT-MM); and
(v) phosphates such as O-(7-azabenzotriazol-1-yl)-N,N,N',N'-tetramethyluronium hexafluorophosphate (HATU), and O-benzotriazol-1-yl-N,N,N',N'-tetramethyluronium hexafluorophosphate (HBTU).

The condensing agent is preferably DMT-MM.

Examples of the base used include triethylamine, diisopropylethylamine, pyridine, 4-dimethylaminopyridine (DMAP), 2,6-lutidine, and 1,4-diazabicyclo[2.2.2]octane (DABCO). The base is preferably diisopropylethylamine.

Examples of a solvent used in the reaction with the compound (11) include alcohols, tetrahydrofuran, dioxane, dimethylformamide, and dimethylacetamide. The solvent is preferably alcohols or dimethylformamide, more preferably dimethylformamide.

[Process D]

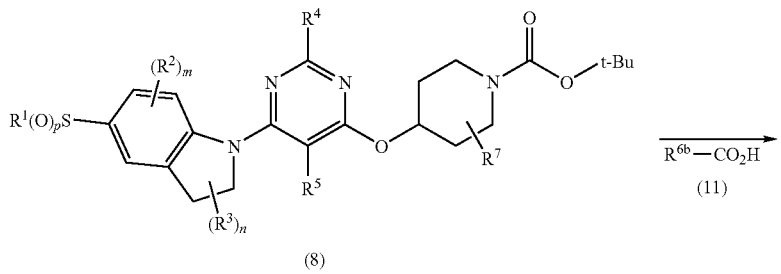

(8)

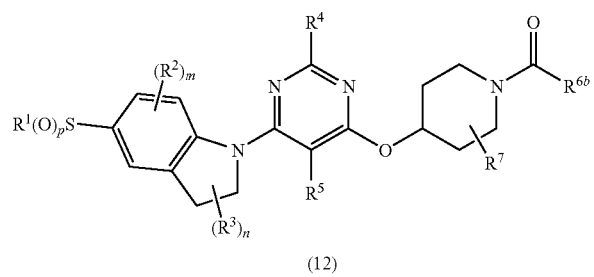

(12)

The process D is a process of removing the Boc group in the compound (8) and then reacting the resulting compound (8) with a compound (11) in the presence of a condensing agent and a base to produce a compound (12).

In the reaction with the compound (11), the reaction temperature is 0 to 100° C., preferably 0 to 50° C.

In the reaction with the compound (11), the reaction time is 30 minutes to 96 hours, preferably 1 to 12 hours.

[Process E]

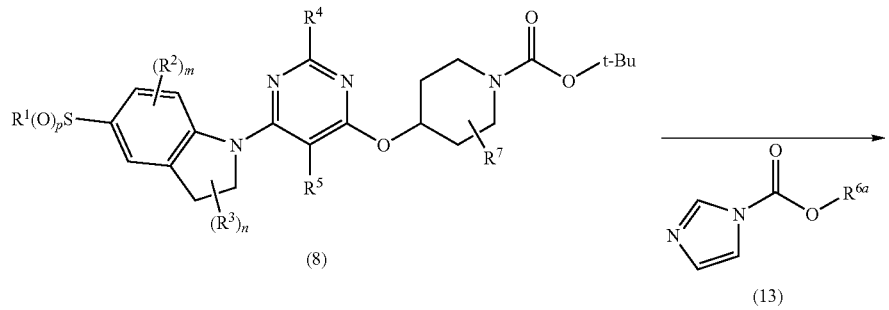

(8) → (13)

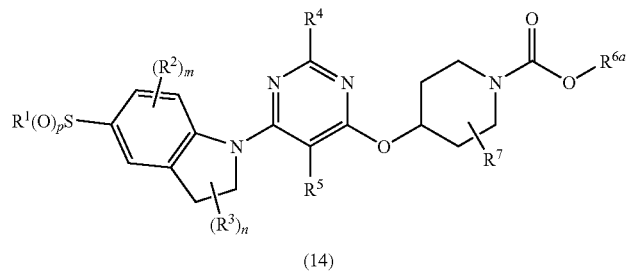

(14)

The process E is a process of removing the Boc group in the compound (8) and then reacting the resulting compound (8) with a compound (13) that can be produced with reference to, for example, WO 2006/4142, to produce a compound (14).

The removal of the Boc group can be performed in the same way as that in the process C.

Examples of a base used include triethylamine, diisopropylethylamine, pyridine, 4-dimethylaminopyridine (DMAP), 2,6-lutidine, 1,4-diazabicyclo[2.2.2]octane (DABCO), sodium carbonate, potassium carbonate, and cesium carbonate. The base is preferably potassium carbonate.

Examples of a solvent used in the reaction with the compound (13) include tetrahydrofuran, dioxane, cyclopentylmethyl ether, dimethylformamide, dimethylacetamide, and toluene. The solvent is preferably 1,4-dioxane.

In the reaction with the compound (13), the reaction temperature is 0 to 150° C., preferably 10 to 100° C.

In the reaction with the compound (13), the reaction time is 30 minutes to 24 hours, preferably 1 to 12 hours.

[Process F]

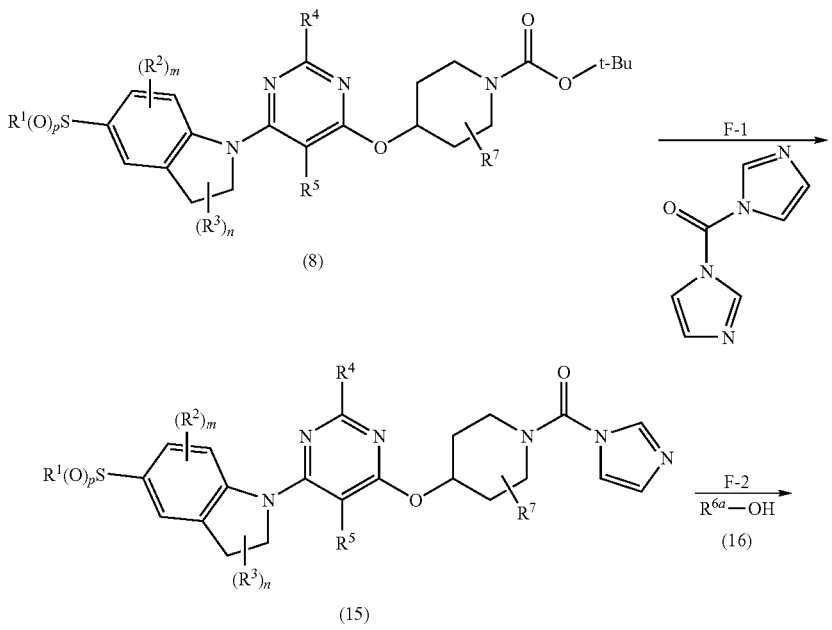

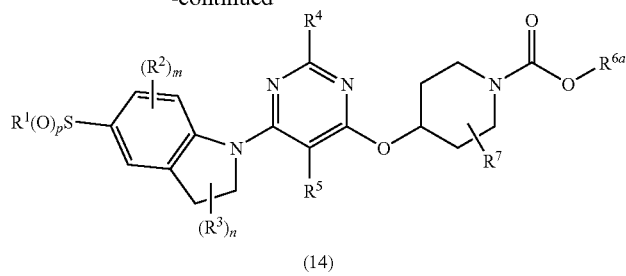

(14)

Another process for producing the compound (14) includes the process F. The process F is a process comprising: a step F-1 of removing the Boc group in the compound (8) and then reacting the resulting compound (8) with 1,1'-carbonyldiimidazole to produce a compound (15); and a step F-2 of reacting the compound (15) obtained in the step F-1 with a compound (16) to produce the compound (14).

(Step F-1)

The removal of the Boc group can be performed in the same way as that in the process C.

Examples of a solvent used in the reaction with 1,1'-carbonyldiimidazole include dichloromethane, dichloroethane, chloroform, tetrahydrofuran, dioxane, cyclopentylmethyl ether, and toluene. The solvent is preferably tetrahydrofuran.

In the reaction with 1,1'-carbonyldiimidazole, the reaction temperature is 0 to 100° C., preferably 10 to 50° C.

In the reaction with 1,1'-carbonyldiimidazole, the reaction time is 10 minutes to 12 hours, preferably 30 minutes to 6 hours.

(Step F-2)

Examples of a solvent used include dichloromethane, dichloroethane, chloroform, tetrahydrofuran, dioxane, cyclopentylmethyl ether, and toluene. The solvent is preferably tetrahydrofuran.

The reaction temperature is −20 to 100° C., preferably 0 to 50° C.

The reaction time is 10 minutes to 12 hours, preferably 30 minutes to 6 hours.

The process G is a process of removing the Boc group in the compound (8) and then reacting the resulting compound (8) with a compound (17) to produce a compound (18).

The removal of the Boc group can be performed in the same way as that in the process C.

Examples of a solvent used in the reaction with the compound (17) include dichloromethane, dichloroethane, chloroform, and toluene. The solvent is preferably dichloromethane.

In the reaction with the compound (17), the reaction temperature is −10 to 60° C., preferably 0 to 40° C.

In the reaction with the compound (17), the reaction time is 10 minutes to 12 hours, preferably 20 minutes to 6 hours.

The compound of the present invention represented by the general formula (I) or (II), which can be obtained by these processes, or the pharmaceutically acceptable salt thereof is useful as an active ingredient in a pharmaceutical composition that can be used in the treatment and/or prevention of type 1 diabetes mellitus, type 2 diabetes mellitus, pregnancy diabetes, hyperglycemia caused by other factors, impaired glucose tolerance (IGT), diabetes-related disease (e.g., adiposity, hyperlipemia, hypercholesterolemia, lipid metabolism abnormality, hypertension, fatty liver, metabolic syndrome, edema, cardiac failure, angina pectoris, myocardial infarction, arteriosclerosis, hyperuricemia, and gout), or complications from diabetes (e.g., retinopathy, nephropathy, neuropathy, cataract, foot gangrene, infectious disease, and ketosis).

[Process G]

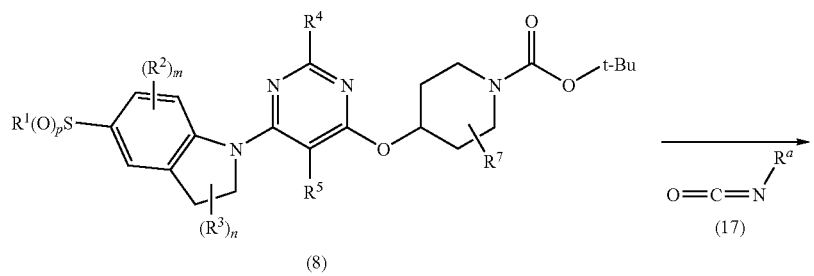

(8)

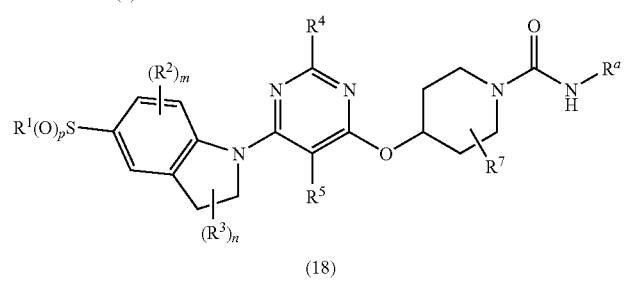

(18)

The pharmaceutical composition comprising the compound of the present invention represented by the general formula (I) or (II) or the pharmaceutically acceptable salt thereof can be administered systemically or locally through oral or parenteral route, when administered to mammals (e.g., humans, horses, cow, or pigs, preferably humans).

The pharmaceutical composition of the present invention can be prepared in an appropriate form selected according to the administration method, by preparation methods for various preparations usually used.

The form of the pharmaceutical composition for oral administration includes tablets, pills, powders, granules, capsules, solutions, suspensions, emulsions, syrups, and elixirs. The pharmaceutical composition in such a form can be prepared according to a standard method by appropriately selecting excipients, binders, disintegrants, lubricants, swelling agents, swelling aids, coating agents, plasticizers, stabilizers, antiseptics, antioxidants, coloring agents, solubilizers, suspending agents, emulsifiers, sweeteners, preservatives, buffers, diluents, wetting agents, etc. usually used as additives.

The form of the pharmaceutical composition for parenteral administration includes injections, ointments, gels, creams, poultices, patches, aerosols, inhalants, sprays, eye drops, nasal drops, suppositories, and inhalants. The pharmaceutical composition in such a form can be prepared according to a standard method by appropriately selecting additives according to need from among stabilizers, antiseptics, humectants, preservatives, antioxidants, flavors, gelling agents, neutralizing agents, solubilizers, buffers, tonicity agents, surfactants, coloring agents, buffering agents, thickeners, wetting agents, fillers, absorption promoters, suspending agents, binders, etc. usually used.

The dose of the compound of the present invention represented by the general formula (I) or (II) or the pharmaceutically acceptable salt thereof differs depending on symptoms, age, body weight, etc., and is, for oral administration, 1 to 2000 mg, preferably 1 to 400 mg (in terms of the amount of the compound) per dose which is administered once to several times a day to an adult and, for parenteral administration, 0.01 to 500 mg, preferably 0.1 to 300 mg (in terms of the amount of the compound) per dose which is administered once to several times a day to an adult.

Hereinafter, the present invention will be described more specifically with reference to Reference Examples, Examples, Preparation Examples, and Test Examples. However, the scope of the present invention is not intended to be limited to these.

EXAMPLES

In the description below, hexane represents n-hexane; THF represents tetrahydrofuran; and DMF represents dimethylformamide.

Reference Example 1

5-(isobutylthio)indoline

An ethanol (14 mL) solution of indolin-5-yl thiocyanate (compound described in the document J. Med. Chem., 1998, vol. 41, p. 1598; 1.33 g, 7.55 mmol) was added to a solution of sodium sulfide nonahydrate (1.84 g, 7.66 mmol) in water (2.8 mL), and the mixture was stirred at 50° C. for 2 hours. To the reaction solution, an ethanol (2.4 mL) solution of isobutyl iodide (1.2 mL, 10.4 mmol) was added, and the mixture was stirred at 50° C. for 2 hours. To the reaction solution, water was added, followed by extraction with ether three times. The obtained organic layer was washed with saturated saline and dried over anhydrous magnesium sulfate, and the solvent was distilled off under reduced pressure. The obtained residue was purified by silica gel column chromatography (hexane:ethyl acetate=90:10-80:20-55:45, V/V) to obtain the title compound as brown oil (0.65 g, yield: 41%).

$^1$H-NMR (400 MHz, CDCl$_3$) δ ppm:7.20 (1H, s), 7.12-7.10 (1H, m), 6.55 (1H, d, J=8 Hz), 3.80 (1H, brs), 3.57 (2H, t, J=8 Hz), 3.01 (2H, t, J=8 Hz), 2.66 (2H, d, J=7 Hz), 1.82-1.72 (1H, m), 0.99 (6H, d, J=7 Hz).

Reference Example 2

5-(ethylthio)indoline

The same reaction as in the method described in Reference Example 1 was performed using iodoethane instead of isobutyl iodide to obtain the title compound as dark brown oil (125 mg, yield: 61%).

$^1$H-NMR (400 MHz, DMSO-d$_6$) δ ppm: 7.08 (1H, s), 6.97 (1H, d, J=8 Hz), 6.43 (1H, s), 5.63 (1H, s), 3.42 (2H, td, J=8 Hz, 1 Hz), 2.89 (2H, t, J=8 Hz), 2.71 (2H, q, J=7 Hz), 1.12 (3H, t, J=7 Hz).

Reference Example 3

5-(isopropylthio)indoline

The same reaction as in the method described in Reference Example 1 was performed using 2-iodopropane instead of isobutyl iodide to obtain the title compound as dark brown oil (109 mg, yield: 50%).

$^1$H-NMR (400 MHz, DMSO-d$_6$) δ ppm: 7.08 (1H, s), 6.99 (1H, d, J=8 Hz), 6.43 (1H, d, J=8 Hz), 5.69 (1H, brs), 3.42 (2H, t, J=9 Hz), 3.05 (1H, sept, J=6 Hz), 2.89 (2H, t, J=8 Hz), 1.14 (6H, d, J=6 Hz).

Reference Example 4

5-(propylthio)indoline

The same reaction as in the method described in Reference Example 1 was performed using 1-iodopropane (122 μL, 1.25 mmol) instead of isobutyl iodide to obtain the title compound as brown oil (151 mg, yield: 69%).

$^1$H-NMR (400 MHz, DMSO-d$_6$) δ ppm: 7.07 (1H, s), 6.97 (1H, d, J=8 Hz), 6.42 (1H, d, J=8 Hz), 5.62 (1H, brs), 3.42 (2H, t, J=8 Hz), 2.88 (2H, t, J=8 Hz), 2.68 (2H, t, J=7 Hz), 1.47 (2H, dt, J=14 Hz, 7 Hz), 0.92 (3H, t, J=7 Hz).

Reference Example 5

5-[(3-chloropropyl)thio]indoline

The same reaction as in the method described in Reference Example 1 was performed using 1-chloro-3-iodopropane (344 μL, 3.20 mmol) instead of isobutyl iodide to obtain the title compound as pale yellow oil (51.3 mg, yield: 28%).

$^1$H-NMR (400 MHz, CDCl$_3$) δ ppm: 7.20 (1H, m), 7.12 (1H, m), 6.56 (1H, d, J=8 Hz), 3.65 (2H, t, J=6 Hz), 3.58 (2H, t, J=8 Hz), 3.02 (2H, t, J=9 Hz), 2.89 (2H, t, J=7 Hz), 1.99 (2H, m, J=6 Hz).

Reference Example 6

5-(cyclopentylthio)indoline

The same reaction as in the method described in Reference Example 1 was performed using iodocyclopentane (457 μL, 3.95 mmol) instead of isobutyl iodide to obtain the title compound as colorless oil (311 mg, yield: 40%).

$^1$H-NMR (400 MHz, CDCl$_3$) δ ppm: 7.35-7.06 (2H, m), 6.54 (1H, m), 3.82 (1H, brs), 3.57 (2H, m), 3.01 (2H, m), 2.76 (1H, m), 2.00-1.16 (8H, m).

Reference Example 7

5-{[2-(benzyloxy)ethyl]thio}indoline

The same reaction as in the method described in Reference Example 1 was performed using benzyl(2-iodoethyl)ether (compound described in the document Tetrahedron Lett., 1987, vol. 28, p. 3091; 962 mg, 3.67 mmol) instead of isobutyl iodide to obtain the title compound as pale green oil (338 mg, yield: 48%).

$^1$H-NMR (400 MHz, CDCl$_3$) δ ppm: 7.36-7.25 (5H, m), 7.20 (1H, m), 7.12 (1H, m), 6.53 (1H, d, J=8 Hz), 4.51 (2H, s), 3.80 (1H, brs), 3.64-3.53 (4H, m), 3.03-2.93 (4H, m).

Reference Example 8

5-(cyclobutylthio)indoline and
5-[(cyclopropylmethyl)thio]indoline

The same reaction as in the method described in Reference Example 1 was performed using bromocyclobutane instead of isobutyl iodide to obtain a crude product. The obtained crude product was purified by preparative HPLC [Inertsil ODS-3 (30 mm i.d.×250 mm); GL Sciences Inc., water:acetonitrile=95:5-0:100 (gradient)] to obtain 5-[(cyclopropylmethyl)thio]indoline (less polar, 81.4 mg, yield: 13%) as a colorless oil compound and 5-(cyclobutylthio)indoline (polar, 62.9 mg, yield: 10%) as a colorless oil compound.

5-[(cyclopropylmethyl)thio]indoline $^1$H-NMR (400 MHz, CDCl$_3$) δ ppm: 7.24 (1H, s), 7.16 (1H, d, J=8 Hz), 6.57 (1H, d, J=8 Hz), 3.58 (2H, t, J=8 Hz), 3.02 (2H, t, J=8 Hz), 2.70 (2H, d, J=7 Hz), 1.04-0.95 (1H, m), 0.55-0.50 (2H, m), 0.20-0.16 (2H, m).

5-(cyclobutylthio)indoline $^1$H-NMR (400 MHz, CDCl$_3$) δ ppm: 7.16 (1H, s), 7.08 (1H, d, J=8 Hz), 6.57 (1H, d, J=8 Hz), 3.86 (1H, brs), 3.69-3.56 (3H, m), 3.02 (2H, t, J=8 Hz), 2.32-2.24 (2H, m), 2.07-1.97 (2H, m), 1.91-1.87 (2H, m).

Reference Example 9

6-fluoro-5-(methylthio)indoline

A saturated sodium bromide-methanol (3.0 mL) solution of bromine (235 μL, 9.19 mmol) was added at 0° C. to a methanol (13.2 mL) solution of 6-fluoroindoline (600 mg, 4.37 mmol) and potassium thiocyanate (1.28 g, 13.1 mmol), and the mixture was stirred for 1.5 hours. To the reaction solution, water was added at 0° C., and the mixture was neutralized with sodium carbonate, followed by extraction with ethanol three times. The organic layer was washed with water and dried over anhydrous sodium sulfate, and the solvent was then distilled off under reduced pressure. The obtained residue was purified by silica gel column chromatography (hexane:ethyl acetate=19:1-4:1, V/V) to obtain a colorless oil compound.

The same reaction as in the method described in Reference Example 1 was performed using the obtained compound and, instead of isobutyl iodide, iodomethane to obtain the title compound as dark brown oil (472 mg, yield: 59%).

$^1$H-NMR (400 MHz, DMSO-d$_6$) δ ppm: 7.07 (1H, s), 6.28 (1H, d, J=11 Hz), 5.91 (1H, brs), 3.49-3.43 (2H, m), 2.87 (2H, t, J=8 Hz), 2.29 (3H, s).

Reference Example 10

6-methoxy-5-(methylthio)indoline

The same reaction as in the method described in Reference Example 9 was performed using 6-methoxyindoline (compound described in the document J. Med. Chem., 2004, vol. 47, p. 5451; 1.29 g, 8.65 mmol) to obtain the title compound as white foam (535 mg, yield: 32%).

$^1$H-NMR (500 MHz, DMSO-d$_6$) δ ppm: 6.93 (1H, s), 6.20 (1H, s), 5.56 (1H, brs), 3.71 (3H, s), 3.41 (2H, t, J=8 Hz), 2.83 (2H, t, J=8 Hz), 2.22 (3H, s).

Reference Example 11

5-(isobutylsulfonyl)indoline hydrochloride

Di(tert-butyl) dicarbonate (790 μL, 3.44 mmol) and triethylamine (620 μL, 4.44 mmol) were added to a dichloromethane (5 mL) solution of the 5-(isobutylthio)indoline (0.65 g, 3.13 mmol) produced in Reference Example 1, and the mixture was stirred at room temperature for 18 hours. To the reaction solution, saturated aqueous sodium bicarbonate was added, followed by extraction with ethyl acetate three times. The obtained organic layer was washed with saturated saline and dried over anhydrous magnesium sulfate, and the solvent was distilled off under reduced pressure. The obtained residue was purified by silica gel column chromatography (hexane:ethyl acetate=90:10-80:20, V/V) to obtain a pale yellow oil compound.

To a dichloromethane (20 mL) solution of the obtained compound, m-chloroperbenzoic acid (ca. 65%, 1.69 g, 6.37 mmol) was added at 0° C., and the mixture was stirred for 1 hour. To the reaction solution, a 10% aqueous sodium sulfite solution was added, followed by extraction with dichloromethane three times. The obtained organic layer was washed with saturated aqueous sodium bicarbonate and saturated saline and dried over anhydrous magnesium sulfate, and the solvent was distilled off under reduced pressure. The obtained residue was purified by silica gel column chromatography (hexane:ethyl acetate=80:20-60:40, V/V) to obtain a white powdery compound.

To an ethyl acetate (10 mL) suspension of the obtained compound, a 4 N hydrochloric acid-ethyl acetate solution (10 mL) was added, and the mixture was stirred at room temperature for 1.5 hours and left for 14 hours. The reaction solution was filtered, and the obtained crude product was washed with a mixed solvent of ethyl acetate and diisopropyl ether to obtain the title compound as pale red powder (445 mg, yield: 52%).

$^1$H-NMR (400 MHz, DMSO-d$_6$) δ ppm: 7.43-7.40 (2H, m), 6.71-6.57 (1H, m), 3.59-3.55 (1H, m), 3.04-3.00 (4H, m), 2.00-1.90 (1H, m), 0.95 (6H, d, J=7 Hz).

Reference Example 12

5-(cyclopentylsulfonyl)indoline

The same reaction as in the method described in Reference Example 11 was performed using the 5-(cyclopentylthio)

indoline (311 mg, 1.42 mmol) produced in Reference Example 6 to obtain an N-Boc indoline intermediate.

To a dichloromethane (20 mL) solution of the obtained compound, trifluoroacetic acid (5 mL) was added, and the mixture was stirred at room temperature for 1 hour. From the reaction solution, the solvent was distilled off under reduced pressure. The obtained residue was purified by silica gel column chromatography (hexane:ethyl acetate=70:30-50:50, V/V) to obtain the title compound as colorless oil (208 mg, yield: 58%).

$^1$H-NMR (400 MHz, CDCl$_3$) δ ppm: 7.55-7.50 (2H, m), 6.60 (1H, d, J=9 Hz), 4.41 (1H, s), 3.70 (2H, t, J=9 Hz), 3.44 (1H, m), 3.09 (2H, t, J=9 Hz), 2.02 (2H, m), 1.88 (2H, m), 1.74 (2H, m), 1.58 (2H, m).

Reference Example 13

5-{[2-(benzyloxy)ethyl]sulfonyl}indoline

The same reaction as in the method described in Reference Example 12 was performed using the 5-{[2-(benzyloxy)ethyl]thio}indoline (338 mg, 1.18 mmol) produced in Reference Example 7 to obtain the title compound as white powder (316 mg, yield: 65%).

$^1$H-NMR (400 MHz, CDCl$_3$) δ ppm: 7.54-5.48 (2H, m), 7.34-7.17 (5H, m), 6.57 (1H, d, J=7 Hz), 4.54 (1H, s), 4.42 (2H, s), 3.82 (2H, t, J=6 Hz), 3.64 (2H, t, J=9 Hz), 3.38 (2H, t, J=6 Hz), 3.00 (2H, t, J=9 Hz).

Reference Example 14

5-[(3-chloropropyl)sulfonyl]indoline

Triethylamine (283 μL, 2.02 mmol) and di(tert-butyl) dicarbonate (331 mg, 1.52 mmol) were added to a dichloromethane (10 mL) solution of the 5-[(3-chloropropyl)thio]indoline (230 mg, 1.01 mmol) produced in Reference Example 5, and the mixture was stirred at room temperature for 40 minutes. To the reaction solution, dimethylaminopyridine (25 mg, 0.245 mmol) was added, and the mixture was stirred at room temperature for 1.5 hours. To the reaction solution, di(tert-butyl) dicarbonate (110 mg, 0.504 mmol) was added, and the mixture was stirred at room temperature for 30 minutes. To the reaction solution, a saturated aqueous solution of ammonium chloride was added, followed by extraction with ethyl acetate twice. The obtained organic layer was dried over anhydrous sodium sulfate, and the solvent was distilled off under reduced pressure. The obtained residue was purified by silica gel column chromatography (hexane:ethyl acetate=49:1-4:1, V/V) to obtain a colorless oil compound.

To a dichloromethane (10 mL) solution of the obtained compound, m-chloroperbenzoic acid (428 mg, 2.48 mmol) was added at 0° C., and the mixture was stirred at 0° C. for 1 hour. To the reaction solution, a saturated aqueous solution of sodium sulfite was added, followed by extraction with ethyl acetate three times. The obtained organic layer was dried over anhydrous sodium sulfate, and the solvent was distilled off under reduced pressure. The obtained residue was purified by silica gel column chromatography (hexane:ethyl acetate=9:1-1:1, V/V) to obtain the title compound as white powder (193 mg).

$^1$H-NMR (400 MHz, CDCl$_3$) δ ppm: 7.97 (1H, brs), 7.71 (1H, dd, J=7 Hz, 1 Hz), 7.64 (1H, d, J=1 Hz), 4.07 (2H, t, J=9 Hz), 3.62 (2H, t, J=6 Hz), 3.23 (2H, t, J=7 Hz), 3.17 (2H, t, J=9 Hz), 2.19 (2H, m), 1.58 (9H, s).

Reference Example 15

5-(cyclopropylsulfonyl)indoline

Potassium hexamethyldisilazide (0.5 M solution in toluene, 892 μL, 0.446 mmol) was added at −78° C. to a THF (5 mL) solution of the 5-[(3-chloropropyl)sulfonyl]indoline (80.2 mg, 0.223 mmol) produced in Reference Example 5, and the mixture was stirred for 1 hour with heating to room temperature. To the reaction solution, a saturated aqueous solution of ammonium chloride was added, followed by extraction with ethyl acetate three times. The obtained organic layer was dried over anhydrous sodium sulfate, and the solvent was distilled off under reduced pressure. The obtained residue was purified by silica gel column chromatography (hexane:ethyl acetate=7:3, V/V) to obtain a white powdery compound.

To a dichloromethane (4 mL) solution of the obtained compound, trifluoroacetic acid (1 mL) was added, and the mixture was stirred at room temperature for 1 hour. From the reaction solution, the solvent was distilled off under reduced pressure. The obtained residue was purified by silica gel column chromatography (hexane:ethyl acetate=3:2, V/V) to obtain the title compound as white powder (20.8 mg, yield: 42%).

$^1$H-NMR (400 MHz, CDCl$_3$) δ ppm: 7.58-7.50 (2H, m), 6.61 (1H, m), 4.16 (1H, s), 3.70 (2H, t, J=8 Hz), 3.09 (2H, t, J=7 Hz), 2.42 (1H, m), 1.28 (2H, m), 0.98 (2H, m).

Reference Example 16

5-[(cyclopropylmethyl)sulfonyl]indoline

The same reaction as in Reference Example 11 was performed using the 5-[(cyclopropylmethyl)thio]indoline (81.4 mg, 0.396 mmol) produced in Reference Example 8 to obtain the title compound as white powder (57 mg, yield: 59%).

$^1$H-NMR (500 MHz, DMSO-d$_6$) δ ppm: 7.51 (1H, brs), 7.42 (1H, s), 7.41 (1H, d, J=9 Hz), 6.57 (1H, d, J=8 Hz), 3.57 (2H, t, J=8 Hz), 3.04 (2H, d, J=7 Hz), 3.01 (2H, t, J=9 Hz), 0.86-0.77 (1H, m), 0.45-0.42 (2H, m), 0.12-0.09 (2H, m).

Reference Example 17

5-(cyclobutylsulfonyl)indoline

The same reaction as in Reference Example 11 was performed using the 5-(cyclobutylthio)indoline (62.9 mg, 0.306 mmol) produced in Reference Example 8 to obtain the title compound as white powder (57.0 mg, yield: 69%).

$^1$H-NMR (500 MHz, DMSO-d$_6$) δ ppm: 7.37 (1H, s), 7.36 (1H, d, J=7 Hz), 6.55 (1H, d, J=8 Hz), 6.42 (1H, brs), 3.87 (1H, quint, J=8 Hz), 3.56 (2H, t, J=8 Hz), 3.00 (2H, t, J=9 Hz), 2.29-2.21 (2H, m), 2.11-2.04 (2H, m), 1.92-1.77 (2H, m).

Reference Example 18

1-acetyl-N,N-dibenzylindoline-5-sulfonamide

Dibenzylamine (302 μL, 1.57 mmol) was added to a dichloromethane (10 mL) solution of 1-acetylindoline-5-sulfonyl chloride (273 mg, 1.05 mmol), and the mixture was stirred at room temperature for 1 hour. To the reaction solution, triethylamine (441 μL, 3.15 mmol) was added, and the mixture was stirred at room temperature for 20 minutes. To the reaction solution, triethylamine (147 μL, 1.05 mmol) and dibenzylamine (100 μL, 0.521 mmol) were added, and the mixture was stirred overnight at room temperature. To the reaction solution, water was added, followed by extraction with ethyl acetate three times. The obtained organic layer was dried over anhydrous sodium sulfate, and the solvent was distilled off under reduced pressure. The obtained residue was purified by silica gel column chromatography [(i) hexane:ethyl acetate=1:1, V/V; (ii) ethyl acetate] to obtain a white powdery compound.

To a methanol (10 mL) solution of the obtained compound, potassium hydroxide (277 mg, 4.94 mmol) was added, and the mixture was stirred for 12.5 hours under heating to reflux. To the reaction solution, saturated ammonium chloride was added, followed by extraction with ethyl acetate three times. The obtained organic layer was dried over anhydrous sodium sulfate, and the solvent was distilled off under reduced pressure. The obtained residue was purified by silica gel column chromatography (hexane:ethyl acetate=3:2, V/V) to obtain the title compound as white powder (386 mg, yield: 100%).

$^1$H-NMR (500 MHz, CDCl$_3$) δ ppm: 7.54 (1H, d, J=8 Hz), 7.49 (1H, s), 7.25-7.18 (6H, m), 7.13-7.05 (4H, m), 6.58 (1H, dd, J=8 Hz, 1 Hz), 4.28 (4H, s), 4.18 (1H, brs), 3.69 (2H, td, J=8 Hz, 1 Hz), 3.06 (2H, t, J=8 Hz).

Reference Example 19

1-(6-chloropyrimidin-4-yl)-5-(methylsulfonyl)indoline

Concentrated hydrochloric acid (810 μL, 9.86 mmol) was added to an acetone (12 mL)/water (3 mL) mixed solution of 2,4-dichloropyrimidine (1.22 g, 8.19 mmol) and 5-methylthioindoline (compound described in the document J. Med. Chem., 1998, vol. 41, p. 1598; 1.63 g, 9.86 mmol), and the mixture was stirred at 80° C. for 1.5 hours. To the reaction solution, saturated aqueous sodium bicarbonate was added, and the deposit was collected by filtration. The obtained crude product was washed with water and diisopropyl ether to obtain a yellow powdery compound.

To a dichloromethane (95 mL) solution of the obtained compound, m-chloroperbenzoic acid (ca. 65%, 3.96 g, 14.9 mmol) was added at 0° C., and the mixture was stirred for 2 hours. To the reaction solution, a 10% aqueous sodium sulfite solution was added, followed by extraction with dichloromethane three times. The obtained organic layer was washed with saturated aqueous sodium bicarbonate and saturated saline and dried over anhydrous magnesium sulfate, and the solvent was distilled off under reduced pressure. The obtained residue was washed with a mixed solvent of diisopropyl ether and ethyl acetate to obtain the title compound as white powder (2.18 g, yield: 86%).

$^1$H-NMR (400 MHz, CDCl$_3$) δ ppm: 8.67 (1H, s), 8.63 (1H, d, J=9 Hz), 7.83 (1H, dd, J=9 Hz, 2 Hz), 7.77 (1H, m), 6.68 (1H, s), 4.13 (2H, t, J=9 Hz), 3.37 (2H, t, J=9 Hz), 3.06 (3H, s).

Reference Example 20

1-(6-chloropyrimidin-4-yl)-5-(ethylsulfonyl)indoline

The same reaction as in the method described in Reference Example 19 was performed using the 5-(ethylthio)indoline (120 mg, 0.669 mmol) produced in Reference Example 2 to obtain the title compound as white powder (122 mg, yield: 56%).

$^1$H-NMR (500 MHz, DMSO-d$_6$) δ ppm: 8.69 (1H, s), 8.59 (1H, d, J=9 Hz), 7.74 (2H, brs), 7.11 (1H, s), 4.17 (2H, t, J=9 Hz), 3.32 (2H, t, J=9 Hz), 3.23 (2H, q, J=7 Hz), 1.10 (3H, t, J=7 Hz).

Reference Example 21

1-(6-chloropyrimidin-4-yl)-5-(propylsulfonyl)indoline

The same reaction as in the method described in Reference Example 19 was performed using the 5-(propylthio)indoline (148 mg, 0.766 mmol) produced in Reference Example 4 to obtain the title compound as white foam (125 mg, yield: 49%).

$^1$H-NMR (400 MHz, DMSO-d$_6$) δ ppm: 8.69 (1H, s), 8.59 (1H, d, J=9 Hz), 7.76-7.73 (2H, m), 7.11 (1H, s), 4.17 (2H, t, J=9 Hz), 3.34-3.30 (2H, m), 3.24-3.20 (2H, m), 1.61-1.51 (2H, m), 0.91 (3H, t, J=7 Hz).

Reference Example 22

1-(6-chloropyrimidin-4-yl)-5-(isopropylsulfonyl)indoline

The same reaction as in the method described in Reference Example 19 was performed using the 5-(isopropylthio)indoline (100 mg, 0.517 mmol) produced in Reference Example 3 to obtain the title compound as white powder (63 mg, yield: 38%).

$^1$H-NMR (500 MHz, DMSO-d$_6$) δ ppm: 8.69 (1H, s), 8.60 (1H, d, J=9 Hz), 7.71 (1H, d, J=9 Hz), 7.70 (1H, s), 7.11 (1H, s), 4.18 (2H, t, J=9 Hz), 3.37-3.31 (3H, m), 1.16 (6H, d, J=7 Hz).

Reference Example 23

1-(6-chloropyrimidin-4-yl)-6-fluoro-5-(methylsulfonyl)indoline

The same reaction as in the method described in Reference Example 19 was performed using the 6-fluoro-5-(methylthio)indoline (250 mg, 1.36 mmol) produced in Reference Example 9 to obtain the title compound as white foam (289 mg, yield: 65%).

$^1$H-NMR (500 MHz, DMSO-d$_6$) δ ppm: 8.73 (1H, s), 8.40 (1H, d, J=13 Hz), 7.68 (1H, d, J=7 Hz), 7.16 (1H, s), 4.20 (2H, t, J=9 Hz), 3.32 (3H, s), 3.32-3.26 (2H, m).

Reference Example 24

6-chloro-1-(6-chloropyrimidin-4-yl)-5-(methylsulfonyl)indoline

The same reaction as in the method described in Reference Example 19 was performed using 6-chloro-5-(methylthio)indoline (compound described in the document J. Med. Chem., 1997, vol. 40, p. 3494; 380 mg, 1.90 mmol) to obtain the title compound as white powder (454 mg, yield: 69%).

$^1$H-NMR (500 MHz, DMSO-d$_6$) δ ppm: 8.76 (1H, s), 8.67 (1H, s), 7.89 (1H, s), 7.15 (1H, s), 4.19 (2H, t, J=9 Hz), 3.32 (3H, s), 3.31-3.29 (2H, m).

Reference Example 25

1-(6-chloropyrimidin-4-yl)-6-methoxy-5-(methylsulfonyl)indoline

The same reaction as in the method described in Reference Example 19 was performed using the 6-methoxy-5-(methylthio)indoline (532 mg, 2.72 mmol) produced in Reference Example 10 to obtain the title compound as white powder (421 mg, yield: 43%).
$^1$H-NMR (400 MHz, DMSO-d$_6$) δ ppm: 8.70 (1H, s), 8.40 (1H, s), 7.63 (1H, s), 7.10 (1H, s), 4.16 (2H, t, J=9 Hz), 3.97 (3H, s), 3.21 (2H, t, J=9 Hz), 3.19 (3H, s).

Reference Example 26

1-(6-chloro-2-methylpyrimidin-4-yl)-5-(methylsulfonyl)indoline

The same reaction as in the method described in Reference Example 19 was performed using 5-methylthioindoline (compound described in the document J. Med. Chem., 1998, vol. 41, p. 1598; 454 mg, 2.75 mmol) and 4,6-dichloro-2-methylpyrimidine (672 mg, 4.12 mmol) to obtain the title compound as white powder (223 mg, yield: 25%).
$^1$H-NMR (400 MHz, CDCl$_3$) δ ppm: 8.64 (1H, d, J=9 Hz), 7.83 (1H, d, J=9 Hz), 7.76 (1H, s), 6.51 (1H, s), 4.11 (2H, t, J=9 Hz), 3.35 (2H, t, J=9 Hz), 3.05 (3H, s), 2.66 (3H, s).

Reference Example 27

5-(methylsulfonyl)-1-[6-(piperidin-4-yloxy)pyrimidin-4-yl]indoline hydrochloride A 4 N hydrochloric acid-ethyl acetate solution (20 mL) was added to an ethyl acetate (10 mL) suspension of tert-butyl 4-({6-[5-(methylsulfonyl)indolin-1-yl]pyrimidin-4-yl}oxy)piperidine-1-carboxylate (1.04 g, 2.19 mmol) produced in Example 1 below, and the mixture was stirred at room temperature for 1 hour. The reaction solution was filtered, and the obtained crude product was washed with ethyl acetate to obtain the title compound as white powder (898 mg, yield: equivalent).
$^1$H-NMR (400 MHz, DMSO-d$_6$) δ ppm: 8.96 (2H, brs), 8.56-8.53 (2H, m), 7.75-7.73 (2H, m), 6.28 (1H, s), 5.36-5.31 (1H, m), 6.28 (1H, s), 5.36-5.31 (1H, m), 4.10 (2H, t, J=9 Hz), 3.29 (2H, t, J=9 Hz), 3.27-3.23 (2H, m), 3.15 (3H, s), 3.15-3.10 (2H, m), 2.19-2.14 (2H, m), 1.95-1.87 (2H, m).

Reference Example 28

5-(methylsulfonyl)-1-[6-(piperidin-4-yloxy)pyrimidin-4-yl]indoline

A 4 N hydrochloric acid-ethyl acetate solution (9.45 mL) was added at 0° C. to an ethyl acetate (3.15 mL) suspension of tert-butyl 4-({6-[5-(methylsulfonyl)indolin-1-yl]pyrimidin-4-yl}oxy)piperidine-1-carboxylate (630 mg, 1.33 mmol) produced in Example 1 below, and the mixture was stirred for 1 hour. The solvent was distilled off under reduced pressure. To the obtained residue, a 1 N aqueous sodium hydroxide solution (20 mL) was added, and the deposit was collected by filtration and washed with water to obtain the title compound as white powder (489 mg, yield: 99%).
$^1$H-NMR (500 MHz, DMSO-d$_6$) δ ppm: 8.54 (1H, d, J=9 Hz), 8.52 (1H, s), 7.73 (2H, s), 6.20 (1H, s), 5.15-5.10 (1H, m), 4.09 (2H, t, J=9 Hz), 3.28 (2H, t, J=9 Hz), 3.14 (3H, s), 2.97-2.94 (2H, m), 2.56 (2H, t, J=10 Hz), 1.95-1.93 (2H, m), 1.53-1.45 (2H, m).

Reference Example 29

1-(6-{[1-(1H-imidazol-1-ylcarbonyl)piperidin-4-yl]oxy}pyrimidin-4-yl)-5-(methylsulfonyl)indoline 1,1'-carbonyldiimidazole (67.0 mg, 0.413 mmol) was added to a THF (2.06 mL) solution of the 5-(methylsulfonyl)-1-[6-(piperidin-4-yloxy)pyrimidin-4-yl]indoline (103 mg, 0.275 mmol) produced in Reference Example 28, and the mixture was stirred at room temperature for 1 hour. From the reaction solution, the solvent was distilled off under reduced pressure. To the residue, water was added, and the mixture was stirred. The deposit was collected by filtration and washed with water to obtain the title compound as white powder (105 mg, yield: 82%).
$^1$H-NMR (500 MHz, DMSO-d$_6$) δ ppm: 8.56 (1H, s), 8.55 (1H, d, J=9 Hz), 8.05 (1H, s), 7.74 (1H, s), 7.73 (1H, d, J=7 Hz), 7.49 (1H, s), 7.04 (1H, s), 6.25 (1H, s), 5.39-5.35 (1H, m), 4.10 (2H, t, J=9 Hz), 3.79-3.74 (2H, m), 3.49-3.44 (2H, m), 3.30-3.27 (2H, m), 3.15 (3H, s), 2.13-2.07 (2H, m), 1.83-1.75 (2H, m).

Reference Example 30

5-(ethylsulfonyl)-1-[6-(piperidin-4-yloxy)pyrimidin-4-yl]indoline

The same reaction as in the method described in Reference Example 28 was performed using tert-butyl 4-({6-[5-(ethylsulfonyl)indolin-1-yl]pyrimidin-4-yl}oxy)piperidine-1-carboxylate (2.58 g, 5.58 mmol) produced in Example 30 below to obtain the title compound as white powder (1.72 g, yield: 79%).
$^1$H-NMR (500 MHz, DMSO-d$_6$) δ ppm: 8.55 (1H, d, J=9 Hz), 8.52 (1H, s), 7.69 (1H, d, J=9 Hz), 7.68 (1H, s), 6.21 (1H, s), 5.15-5.10 (1H, m), 4.09 (2H, t, J=9 Hz), 3.30-3.26 (3H, m), 3.22 (2H, q, J=7 Hz), 2.96 (2H, dt, J=13 Hz, 4 Hz), 2.57 (2H, td, J=11 Hz, 1 Hz), 1.97-1.94 (2H, m), 1.49 (2H, t, J=9 Hz, 4 Hz), 1.10 (3H, t, J=7 Hz).

Reference Example 31

5-(ethylsulfonyl)-1-(6-{[1-(1H-imidazol-1-ylcarbonyl)piperidin-4-yl]oxy}pyrimidin-4-yl)indoline The same reaction as in the method described in Reference Example 29 was performed using the 5-(ethylsulfonyl)-1-[6-(piperidin-4-yloxy)pyrimidin-4-yl]indoline (1.96 g, 5.05 mmol) produced in Reference Example 30 to obtain the title compound as white powder (1.98 g, yield: 81%).
$^1$H-NMR (500 MHz, DMSO-d$_6$) δ ppm: 8.56 (1H, d, J=9 Hz), 8.56 (1H, s), 8.05 (1H, s), 7.69 (1H, d, J=7 Hz), 7.68 (1H, s), 7.49 (1H, s), 7.04 (1H, s), 6.25 (1H, s), 5.40-5.35 (1H, m), 4.10 (2H, t, J=9 Hz), 3.79-3.74 (2H, m), 3.49-3.44 (2H, m), 3.29 (2H, t, J=9 Hz), 3.21 (2H, q, J=7 Hz), 2.13-2.08 (2H, m), 1.83-1.75 (2H, m), 1.10 (3H, t, J=7 Hz).

Reference Example 32

1-[6-(piperidin-4-yloxy)pyrimidin-4-yl]-5-(propylsulfonyl)indoline hydrochloride The same reaction as in the method described in Reference Example 27 was performed using tert-butyl 4-({6-[5-(propylsulfonyl)indolin-1-yl]pyrimidin-4-yl}oxy)piperidine-1-carboxylate (1.19 g, 2.37 mmol) produced in Example 36 to obtain the title compound as white powder (1.07 g, yield: equivalent).
$^1$H-NMR (400 MHz, DMSO-d$_6$) δ ppm: 8.96 (2H, brs), 8.56-8.54 (2H, m), 7.71-7.68 (2H, m), 6.28 (1H, s), 5.36-5.30 (1H, m), 6.28 (1H, s), 5.36-5.30 (1H, m), 4.10 (2H, t, J=9 Hz), 3.31-3.08 (8H, m), 2.19-2.14 (2H, m), 1.99-1.87 (2H, m), 1.60-1.50 (2H, m), 0.91 (3H, t, J=7 Hz).

Reference Example 33

1-(6-{[1-(1H-imidazol-1-ylcarbonyl)piperidin-4-yl]oxy}pyrimidin-4-yl)-5-(propylsulfonyl)indoline Triethylamine (286 μL, 2.05 mmol) and 1,1'-carbonyldiimidazole (249 mg, 1.54 mmol) were added to a THF (9.00 mL) solution of the 1-[6-(piperidin-4-yloxy)pyrimidin-4-yl]-5-(propylsulfonyl)indoline hydrochloride (450 mg, 1.03 mmol) produced in Reference Example 32, and the mixture was stirred at room temperature for 3 hours. From the reaction solution, the solvent was distilled off under reduced pressure. To the residue, water was added, and the mixture was stirred. The deposit was collected by filtration and washed with water to obtain the title compound as white powder (291 mg, yield: 57%).
$^1$H-NMR (400 MHz, DMSO-$d_6$) δ ppm: 8.56 (1H, s), 8.55 (1H, d, J=9 Hz), 8.05 (1H, s), 7.69 (1H, d, J=7 Hz), 7.68 (1H, s), 7.49 (1H, s), 7.05 (1H, s), 6.25 (1H, s), 5.40-5.34 (1H, m), 4.10 (2H, t, J=9 Hz), 3.80-3.74 (2H, m), 3.49-3.43 (2H, m), 3.31-3.27 (2H, m), 3.21-3.18 (2H, m), 2.14-2.07 (2H, m), 1.84-1.76 (2H, m), 1.60-1.51 (2H, m), 0.91 (3H, t, J=7 Hz).

Reference Example 34

1-[6-(piperidin-4-yloxy)pyrimidin-4-yl]-5-(propylsulfonyl)indoline

A 2 N aqueous sodium hydroxide solution (363 mL, 0.726 mmol) was added to an ethylene glycol (3.6 mL) solution of the 1-(6-{[1-(1H-imidazol-1-ylcarbonyl)piperidin-4-yl]oxy}pyrimidin-4-yl)-5-(propylsulfonyl)indoline (180 mg, 0.363 mmol) produced in Reference Example 33, and the mixture was stirred at 100° C. for 2.5 hours. To the reaction solution, water was added, followed by extraction with ethyl acetate three times. The obtained organic layer was washed with water and dried over anhydrous sodium sulfate, and the solvent was distilled off under reduced pressure to obtain the title compound as white powder (106 mg, yield: 73%).
$^1$H-NMR (500 MHz, DMSO-$d_6$) δ ppm: 8.54 (1H, d, J=9 Hz), 8.53 (1H, s,), 7.69 (1H, d, J=6 Hz), 7.68 (1H, s), 6.21 (1H, s), 5.18-5.11 (1H, m), 4.09 (2H, t, J=9 Hz), 3.21-3.17 (4H, m), 2.99 (2H, dt, J=13 Hz, 5 Hz), 2.67-2.60 (2H, m), 2.00-1.95 (2H, m), 1.60-1.49 (4H, m), 0.91 (3H, t, J=7 Hz).

Reference Example 35

1-(6-{[1-(1H-imidazol-1-ylcarbonyl)piperidin-4-yl]oxy}pyrimidin-4-yl)-5-(isopropylsulfonyl)indoline The same reaction as in the method described in Reference Example 28 was performed using tert-butyl 4-({6-[5-(isopropylsulfonyl)indolin-1-yl]pyrimidin-4-yl}oxy)piperidine-1-carboxylate (272 mg, 0.541 mmol) produced in Example 32 below to obtain a white powdery compound.
The same reaction as in the method described in Reference Example 33 was performed using the obtained compound to obtain the title compound as white powder (240 mg, yield: 91%).
$^1$H-NMR (500 MHz, DMSO-$d_6$) δ ppm: 8.57 (1H, d, J=9 Hz), 8.56 (1H, s), 8.05 (1H, s), 7.66 (1H, d, J=8 Hz), 7.65 (1H, s), 7.49 (1H, s), 7.04 (1H, s), 6.25 (1H, s), 5.40-5.35 (1H, m), 4.10 (2H, t, J=9 Hz), 3.79-3.74 (2H, m), 3.49-3.44 (2H, m), 3.31-3.28 (3H, m), 2.13-2.07 (2H, m), 1.83-1.75 (2H, m), 1.16 (6H, d, J=7 Hz).

Reference Example 36

5-(isobutylsulfonyl)-1-[6-(piperidin-4-yloxy)pyrimidin-4-yl]indoline

The same reaction as in the method described in Reference Example 30 was performed using tert-butyl 4-({6-[5-(isobutylsulfonyl)indolin-1-yl]pyrimidin-4-yl}oxy)piperidine-1-carboxylate (2.08 g, 4.03 mmol) produced in Example 25 below to obtain the title compound as white powder (1.60 g, yield: 95%).
$^1$H-NMR (500 MHz, DMSO-$d_6$) δ ppm: 8.54 (1H, d, J=9 Hz), 8.52 (1H, s), 7.70-7.69 (2H, m), 6.20 (1H, s), 5.15-5.10 (1H, m), 4.09 (2H, t, J=9 Hz), 3.28 (2H, t, J=9 Hz), 3.13 (2H, d, J=7 Hz), 2.98-2.94 (2H, m), 2.59-2.54 (2H, m), 2.03-1.93 (3H, m), 1.53-1.45 (2H, m), 0.97 (6H, d, J=6 Hz).

Reference Example 37

1-(6-{[1-(1H-imidazol-1-ylcarbonyl)piperidin-4-yl]oxy}pyrimidin-4-yl)-5-(isobutylsulfonyl)indoline The same reaction as in the method described in Reference Example 33 was performed using the 5-(isobutylsulfonyl)-1-[6-(piperidin-4-yloxy)pyrimidin-4-yl]indoline (900 mg, 2.16 mmol) produced in Reference Example 36 to obtain the title compound as white powder (965 mg, yield: 88%).
$^1$H-NMR (500 MHz, DMSO-$d_6$) δ ppm: 8.56 (1H, s), 8.55 (1H, d, J=9 Hz), 8.05 (1H, s), 7.71 (1H, d, J=9 Hz), 7.70 (1H, s), 7.49 (1H, s), 7.04 (1H, s), 6.25 (1H, s), 5.40-5.35 (1H, m), 4.10 (2H, t, J=9 Hz), 3.79-3.74 (2H, m), 3.49-3.44 (2H, m), 3.31-3.27 (2H, m), 3.13 (2H, d, J=6 Hz), 2.13-2.07 (2H, m), 2.03-1.95 (1H, m), 1.83-1.77 (2H, m), 0.96 (6H, d, J=7 Hz).

Reference Example 38

5-[(cyclopropylmethyl)sulfonyl]-1-[6-(piperidin-4-yloxy)pyrimidin-4-yl]indoline

The same reaction as in the method described in Reference Example 30 was performed using tert-butyl 4-[(6-{5-[(cyclopropylmethyl)sulfonyl]indolin-1-yl}pyrimidin-4-yl]oxy)piperidine-1-carboxylate (1.36 g, 2.64 mmol) produced in Example 56 below to obtain a white powdery compound (621 mg, yield: 57%).
$^1$H-NMR (400 MHz, DMSO-$d_6$) δ ppm: 8.55 (1H, d, J=9 Hz), 8.52 (1H, s,), 7.69 (1H, d, J=8 Hz), 7.68 (1H, s), 6.20 (1H, s), 5.16-5.09 (1H, m), 4.09 (2H, t, J=9 Hz), 3.28 (2H, t, J=9 Hz), 3.17 (2H, d, J=7 Hz), 2.96 (2H, dt, J=13 Hz, 4 Hz), 2.60-2.54 (2H, m), 1.98-1.92 (2H, m), 1.54-1.45 (2H, m), 0.88-0.79 (1H, m), 0.47-0.43 (2H, m), 0.13-0.09 (2H, m).

Reference Example 39

5-[(cyclopropylmethyl)sulfonyl]-1-(6-{[1-(1H-imidazol-1-ylcarbonyl)piperidin-4-yl]oxy}pyrimidin-4-yl)indoline The same reaction as in the method described in Reference Example 33 was performed using the 5-[(cyclopropylmethyl)sulfonyl]-1-[6-(piperidin-4-yloxy)pyrimidin-4-yl]indoline (122 mg, 0.293 mmol) produced in Reference Example 38 to obtain the title compound as white powder (121 mg, yield: 81%).
$^1$H-NMR (500 MHz, DMSO-$d_6$) δ ppm: 8.56 (1H, s), 8.55 (1H, d, J=9 Hz), 8.05 (1H, s), 7.70 (1H, d, J=8 Hz), 7.69 (1H, s), 7.49 (1H, s), 7.04 (1H, s), 6.25 (1H, s), 5.40-5.35 (1H, m), 4.11 (2H, t, J=9 Hz), 3.79-3.74 (2H, m), 3.49-3.44 (2H, m), 3.31-3.27 (2H, m), 3.18 (2H, d, J=7 Hz), 2.12-2.08 (2H, m), 1.83-1.77 (2H, m), 0.87-0.80 (1H, m), 0.47-0.43 (2H, m), 0.13-0.10 (2H, m).

Reference Example 40 tert-butyl 4-[(6-chloro-5-methylpyrimidin-4-yl)oxy]piperidine-1-carboxylate

Tert-butyl 4-hydroxypiperidine-1-carboxylate (2.47 g, 12.3 mmol) and potassium tert-butoxide (1.42 g, 12.7 mmol) were added to a THF (20 mL) solution of 2,4-dichloro-3-methylpyrimidine (1.60 g, 9.82 mmol), and the mixture was stirred for 2 hours. To the reaction solution, water was added, followed by extraction with ethyl acetate three times. The obtained organic layer was washed with saturated saline and dried over anhydrous sodium sulfate, and the solvent was distilled off under reduced pressure. The obtained residue was purified by silica gel column chromatography (hexane:ethyl acetate=80:20-60:40, V/V) to obtain the title compound as colorless oil (3.07 g, yield: 95%).

$^1$H-NMR (400 MHz, CDCl$_3$) δ ppm: 8.39 (1H, s), 5.36-5.31 (1H, m), 3.75-3.69 (2H, m), 3.75-3.69 (2H, m), 3.39-3.33 (2H, m), 2.23 (3H, s), 2.02-1.95 (2H, m), 1.80-1.72 (2H, m), 1.48 (9H, s).

Reference Example 41 tert-butyl 4-[(6-chloropyrimidin-4-yl)oxy]piperidine-1-carboxylate

The same reaction as in the method described in Reference Example 40 was performed using 2,4-dichloropyrimidine (3.14 g, 15.6 mmol) to obtain the title compound as white powder (3.22 g, yield: 66%).

$^1$H-NMR (400 MHz, CDCl$_3$) δ ppm: 8.55 (1H, s), 6.76 (1H, s), 5.34-5.28 (1H, m), 3.79-3.75 (2H, m), 3.32-3.26 (2H, m), 2.02-1.96 (2H, m), 1.78-1.69 (2H, m), 1.48 (9H, s).

Reference Example 42 isopropyl 4-[(6-chloropyrimidin-4-yl)oxy]piperidine-1-carboxylate

The same reaction as in the method described in Reference Example 40 was performed using 2,4-dichloropyrimidine (4.19 g, 28.1 mmol) and, instead of tert-butyl 4-hydroxypiperidine-1-carboxylate, isopropyl 4-hydroxypiperidine-1-carboxylate (5.25 g, 28.1 mmol) to obtain the title compound as white powder (5.88 g, yield: 70%).

$^1$H-NMR (500 MHz, CDCl$_3$) δ ppm: 8.55 (1H, s), 6.76 (1H, s), 5.35-5.31 (1H, m), 4.93 (1H, sept, J=6 Hz), 3.81-3.79 (2H, m), 3.36-3.31 (2H, m), 2.01-1.96 (2H, m), 1.78-1.72 (2H, m), 1.26 (6H, d, J=6 Hz).

Reference Example 43 tert-butyl 4-[(6-chloro-5-methoxypyrimidin-4-yl)oxy]piperidine-1-carboxylate

The same reaction as in the method described in Reference Example 40 was performed using 2,4-dichloro-5-methoxypyrimidine (302 mg, 1.50 mmol) to obtain the title compound as white powder (357 mg, yield: 69%).

$^1$H-NMR (400 MHz, CDCl$_3$) δ ppm: 8.27 (1H, s), 5.40-5.34 (1H, m), 3.91 (3H, s), 3.78-3.72 (2H, m), 3.39-3.33 (2H, m), 2.04-1.97 (2H, m), 1.48 (9H, s).

Reference Example 44 tert-butyl 4-{[6-(5-{[2-(benzyloxy)ethyl]sulfonyl}indolin-1-yl)pyrimidin-4-yl]oxy}piperidine-1-carboxylate The same reaction as in the method described in Example 56 was performed using the tert-butyl 4-[(6-chloropyrimidin-4-yl)oxy]piperidine-1-carboxylate (397 mg, 1.27 mmol) produced in Reference Example 41 and, instead of 5-[(cyclopropylmethyl)sulfonyl]indoline, the 5-{[2-(benzyloxy)ethyl]sulfonyl}indoline (316 mg, 0.998 mmol) produced in Reference Example 13 to obtain the title compound as pale yellow oil (486 mg, yield: 82%).

$^1$H-NMR (400 MHz, CDCl$_3$) δ ppm: 8.53 (1H, d, J=9 Hz), 8.51 (1H, d, J=1 Hz), 7.74 (1H, dd, J=9 Hz, 2 Hz), 7.63 (1H, m), 7.27-7.21 (3H, m), 7.18-7.13 (2H, m), 5.98 (1H, d, J=1 Hz), 5.32 (1H, m), 4.40 (2H, s), 3.99 (2H, t, J=9 Hz), 3.85 (2H, t, J=6 Hz), 3.81 (2H, m), 3.42 (2H, t, J=6 Hz), 3.28 (2H, m), 3.16 (2H, t, J=9 Hz), 2.01 (2H, m), 1.73 (2H, m), 1.48 (9H, s).

Reference Example 45 tert-butyl 4-[(6-{5-[(dibenzylamino)sulfonyl]indolin-1-yl}pyrimidin-4-yl) oxy]piperidine-1-carboxylate The same reaction as in the method described in Example 56 was performed using the tert-butyl 4-[(6-chloropyrimidin-4-yl)oxy]piperidine-1-carboxylate (185 mg, 0.591 mmol) produced in Reference Example 41 and, instead of 5-[(cyclopropylmethyl)sulfonyl]indoline, the 1-acetyl-N,N-dibenzylindoline-5-sulfonamide (187 mg, 0.493 mmol) produced in Reference Example 18 to obtain the title compound as colorless oil (269 mg, yield: 83%).

$^1$H-NMR (400 MHz, CDCl$_3$) δ ppm: 8.52 (1H, d, J=8 Hz), 8.51 (1H, s), 7.74 (1H, dd, J=9 Hz, 2 Hz), 7.57 (1H, s), 7.25-7.20 (6H, m), 7.12-7.07 (4H, m), 5.98 (1H, s), 5.32 (1H, m), 4.31 (4H, s), 4.05 (2H, t, J=9 Hz), 3.81 (2H, m), 3.33-3.22 (4H, m), 2.01 (2H, m), 1.73 (2H, m), 1.48 (9H, s).

Example 1 tert-butyl 4-({6-[5-(methylsulfonyl)indolin-1-yl]pyrimidin-4-yl}oxy)piperidine-1-carboxylate (exemplary compound No: 8)

Tert-butyl 4-hydroxypiperidine-1-carboxylate (1.24 g, 6.16 mmol) was added at 0° C. to a THF (15 mL) suspension of sodium hydride (63% dispersion in mineral oil; hereinafter, referred to as sodium hydride (63%); 281 mg, 7.38 mmol), and the mixture was stirred at room temperature for 1 hour. To the reaction solution, the 1-(6-chloropyrimidin-4-yl)-5-(methylsulfonyl)indoline (1.87 g, 6.04 mmol) produced in Reference Example 19 and THF (5 mL) were added, and the mixture was stirred at 70° C. for 4 hours. To the reaction solution, a saturated aqueous solution of ammonium chloride was added, followed by extraction with ethyl acetate three times. The obtained organic layer was washed with saturated saline and dried over anhydrous magnesium sulfate, and the solvent was distilled off under reduced pressure. The obtained residue was purified by silica gel column chromatography [(i) hexane:ethyl acetate=50:50, V/V; (ii) ethyl acetate]. The obtained crude product was washed with water and diisopropyl ether to obtain the title compound as white powder (2.03 g, yield: 71%).

$^1$H-NMR (400 MHz, CDCl$_3$) δ ppm: 8.58 (1H, d, J=9 Hz), 8.51 (1H, d, J=1 Hz), 7.79 (1H, dd, J=9 Hz, 2 Hz), 7.72 (1H, d, J=2 Hz), 5.98 (1H, d, J=1 Hz), 5.35-5.29 (1H, m), 4.07 (2H, t, J=9 Hz), 3.83-3.77 (2H, m), 3.33-3.25 (4H, m), 3.04 (3H, s), 2.03-1.97 (2H, m), 1.77-1.69 (2H, m), 1.48 (9H, s);

MS (ESI) m/z: 475 [M+H]$^+$.

Example 2 isopropyl 4-({6-[5-(methylsulfonyl)indolin-1-yl]pyrimidin-4-yl}oxy)piperidine-1-carboxylate (exemplary compound No: 4)

Trifluoroacetic acid (1 mL) was added to a dichloromethane (1 mL) solution of the tert-butyl 4-({6-[5-(methylsulfonyl)indolin-1-yl]pyrimidin-4-yl}oxy)piperidine-1-carboxylate (188 mg, 0.396 mmol) produced in Example 1, and the mixture was stirred at room temperature for 2 hours. From the reaction solution, the solvent was distilled off under reduced pressure. To a dichloromethane (2.5 mL) solution of the obtained residue, isopropyl chloroformate (68 μL, 0.60 mmol) and triethylamine (276 μL, 1.98 mmol) were added at 0° C., and the mixture was stirred at room temperature. After 1.5 hours, isopropyl chloroformate (100 μL, 0.878 mmol) and triethylamine (410 μL, 2.94 mmol) were added to the reaction solution, and the mixture was further stirred for 1 hour. To the reaction solution, water was added, followed by extraction with ethyl acetate three times. The obtained organic layer was washed with saturated saline and dried over anhydrous magnesium sulfate, and the solvent was distilled off under reduced pressure. The obtained residue was purified by silica gel column chromatography [(i) hexane:ethyl acetate=70:30-50:50, V/V; (ii) ethyl acetate] to obtain the title compound as white powder (82.8 mg, yield: 45%).

$^1$H-NMR (400 MHz, CDCl$_3$) δ ppm: 8.57 (1H, d, J=9 Hz), 8.51 (1H, d, J=1 Hz), 7.79 (1H, dd, J=9 Hz, 2 Hz), 7.72 (1H, d, J=2 Hz), 5.98 (1H, d, J=1 Hz), 5.36-5.30 (1H, m), 4.94 (1H, sept, J=6 Hz), 4.07 (2H, t, J=9 Hz), 3.87-3.80 (2H, m), 3.36-3.29 (4H, m), 3.06 (3H, s), 2.03-1.98 (2H, m), 1.78-1.70 (2H, m), 1.26 (6H, d, J=6 Hz);

MS (ESI) m/z: 461 [M+H]$^+$.

Example 3

2-fluoroethyl 4-({6-[5-(methylsulfonyl)indolin-1-yl]pyrimidin-4-yl}oxy)piperidine-1-carboxylate (exemplary compound No: 34)

Diisopropylethylamine (178 μL, 0.997 mmol) and (2-fluoroethyl) chloroformate (33 μL, 0.350 mmol) were added at 0° C. to a dichloromethane (2 mL) suspension of the 5-(methylsulfonyl)-1-[6-(piperidin-4-yloxy)pyrimidin-4-yl]indoline hydrochloride (188 mg, 0.396 mmol) produced in Reference Example 27, and the mixture was stirred at room temperature for 80 minutes. To the reaction solution, water was added, followed by extraction with ethyl acetate three times. The obtained organic layer was washed with water and saturated saline and dried over anhydrous magnesium sulfate, and the solvent was distilled off under reduced pressure. The obtained residue was purified by silica gel column chromatography [(i) hexane:dichloromethane=1:1, V/V; (ii) hexane:ethyl acetate:dichloromethane=2:1:2-1:1:1-2:2:1, V/V; (iii) ethyl acetate:dichloromethane=1:1, V/V] to obtain the title compound as white powder (58.8 mg, yield: 38%).

$^1$H-NMR (400 MHz, CDCl$_3$) δ ppm: 8.58 (1H, d, J=9 Hz), 8.51 (1H, d, J=1 Hz), 7.79 (1H, dd, J=9 Hz, 2 Hz), 7.72 (1H, d, J=2 Hz), 5.99 (1H, d, J=1 Hz), 5.38-5.35 (1H, m), 4.70-4.68 (1H, m), 4.58-4.56 (1H, m), 4.40-4.38 (1H, m), 4.33-4.31 (1H, m), 4.07 (2H, t, J=9 Hz), 3.88-3.82 (2H, m), 3.44-3.38 (2H, m), 3.32 (2H, t, J=9 Hz), 3.04 (3H, s), 2.06-2.00 (2H, m), 1.82-1.74 (2H, m);

MS (ESI) m/z: 465 [M+H]$^+$.

Example 4

4-[4-({6-[5-(methylsulfonyl)indolin-1-yl]pyrimidin-4-yl}oxy)piperidin-1-yl]-4-oxobutan-2-ol (exemplary compound No: 97)

3-hydroxybutanoic acid (61 μL, 0.66 mmol), diisopropylethylamine (102 μL, 0.571 mmol), and 4-(dimethoxy-1,3,5-triazin-2-yl)-4-methylmorpholinium chloride (235 mg, 0.849 mmol) were added to an ethanol (3 mL) suspension of the 5-(methylsulfonyl)-1-[6-(piperidin-4-yloxy)pyrimidin-4-yl]indoline hydrochloride (224 mg, 0.545 mmol) produced in Reference Example 27, and the mixture was stirred at room temperature for 3 days. To the reaction solution, water was added, followed by extraction with dichloromethane three times. The obtained organic layer was washed with saturated saline and dried over anhydrous magnesium sulfate, and the solvent was distilled off under reduced pressure. The obtained residue was purified by thin-layer silica gel chromatography (dichloromethane:methanol=1:1, V/V). The obtained crude product was washed with diisopropyl ether to obtain the title compound as grayish white foam (174 mg, yield: 69%).

$^1$H-NMR (400 MHz, CDCl$_3$) δ ppm: 8.57 (1H, d, J=9 Hz), 8.51 (1H, brs), 7.79 (1H, dd, J=9 Hz, 2 Hz), 7.72 (1H, d, J=2 Hz), 5.99 (1H, brs), 5.42-5.37 (1H, m), 4.24-3.30 (9H, m), 3.04 (3H, s), 2.55-2.31 (2H, m), 2.08-2.00 (2H, m), 1.84-1.76 (2H, m), 1.24 (3H, d, J=7 Hz);

MS (FAB) m/z: 461 [M+H]$^+$.

Example 5 benzyl 4-({6-[5-(methylsulfonyl)indolin-1-yl]pyrimidin-4-yl}oxy)piperidine-1-carboxylate (exemplary compound No: 49)

Diisopropylethylamine (93 μL, 0.53 mmol) and benzyl chloroformate (57 μL, 0.40 mmol) were added at 0° C. to a dichloromethane (5 mL) solution of the 5-(methylsulfonyl)-1-[6-(piperidin-4-yloxy)pyrimidin-4-yl]indoline (100 mg, 0.267 mmol) produced in Reference Example 28, and the mixture was stirred at room temperature for 1 hour. To the reaction solution, water was added, followed by extraction with dichloromethane three times. The obtained organic layer was washed with saturated saline and dried over anhydrous magnesium sulfate, and the solvent was distilled off under reduced pressure. The obtained residue was purified by silica gel column chromatography (hexane:ethyl acetate=5:1-1:1, V/V). The obtained crude product was washed with diisopropyl ether to obtain the title compound as white powder (67.3 mg, yield: 50%).

$^1$H-NMR (400 MHz, CDCl$_3$) δ ppm: 8.58 (1H, d, J=9 Hz), 8.51 (1H, d, J=1 Hz), 7.79 (1H, dd, J=9 Hz, 2 Hz), 7.72 (1H, brs), 7.38-7.37 (5H, m), 5.98 (1H, d, J=1 Hz), 5.37-5.31 (1H, m), 5.15 (2H, m), 4.07 (2H, t, J=9 Hz), 3.89-3.82 (2H, m), 3.43-3.37 (2H, m), 3.31 (2H, t, J=9 Hz), 3.04 (3H, s), 2.05-1.98 (2H, m), 1.80-1.72 (2H, m);

MS (CI) m/z: 509 [M+H]$^+$.

Example 6 butyl 4-({6-[5-(methylsulfonyl)indolin-1-yl]pyrimidin-4-yl}oxy)piperidine-1-carboxylate (exemplary compound No: 5)

Diisopropylethylamine (186 μL, 1.07 mmol) and butyl chloroformate (51 μL, 0.40 mmol) were added at 0° C. to a dichloromethane (5 mL) solution of the 5-(methylsulfonyl)-1-[6-(piperidin-4-yloxy)pyrimidin-4-yl]indoline (100 mg, 0.267 mmol) produced in Reference Example 28, and the mixture was stirred at room temperature for 1 hour. To the reaction solution, water was added, followed by extraction with ethyl acetate three times. The obtained organic layer was washed with saturated saline and dried over anhydrous magnesium sulfate, and the solvent was distilled off under reduced pressure. The obtained residue was purified by silica gel column chromatography (hexane:ethyl acetate=5:1-1:2, V/V) to obtain the title compound as white powder (53.9 mg, yield: 43%).

$^1$H-NMR (400 MHz, CDCl$_3$) δ ppm: 8.58 (1H, d, J=9 Hz), 8.51 (1H, d, J=1 Hz), 7.79 (1H, dd, J=9 Hz, 2 Hz), 7.72 (1H, brs), 5.98 (1H, d, J=1 Hz), 5.36-5.31 (1H, m), 4.10 (2H, t, J=7 Hz), 4.07 (2H, t, J=9 Hz), 3.87-3.80 (2H, m), 3.38-3.29 (4H, m), 3.04 (3H, s), 2.05-1.98 (2H, m), 1.79-1.71 (2H, m), 1.67-1.60 (2H, m), 1.45-1.35 (2H, m), 0.95 (3H, t, J=7 Hz);

MS (CI) m/z: 475 [M+H]$^+$.

Example 7 propyl 4-({6-[5-(methylsulfonyl)indolin-1-yl]pyrimidin-4-yl}oxy)piperidine-1-carboxylate (exemplary compound No: 3)

The same reaction as in the method described in Example 6 was performed using the 5-(methylsulfonyl)-1-[6-(piperidin-4-yloxy)pyrimidin-4-yl]indoline (100 mg, 0.267 mmol) produced in Reference Example 28 and, instead of butyl chloroformate, propyl chloroformate (45 μL, 0.40 mmol) to obtain the title compound as white powder (58.6 mg, yield: 48%).

$^1$H-NMR (400 MHz, CDCl$_3$) δ ppm: 8.58 (1H, d, J=9 Hz), 8.52 (1H, d, J=1 Hz), 7.79 (1H, dd, J=9 Hz, 2 Hz), 7.72 (1H, brs), 5.99 (1H, s), 5.37-5.32 (1H, m), 4.10-4.05 (4H, m), 3.05 (3H, s), 2.05-1.98 (2H, m), 1.80-1.63 (4H, m), 0.96 (3H, t, J=7 Hz);

MS (CI) m/z: 461 [M+H]$^+$.

Example 8

2-methoxyethyl 4-({6-[5-(methylsulfonyl)indolin-1-yl]pyrimidin-4-yl}oxy)piperidine-1-carboxylate (exemplary compound No: 40)

The same reaction as in the method described in Example 6 was performed using the 5-(methylsulfonyl)-1-[6-(piperidin-4-yloxy)pyrimidin-4-yl]indoline (100 mg, 0.267 mmol) produced in Reference Example 28 and, instead of butyl chloroformate, methoxyethyl chloroformate (46 μL, 0.40 mmol) to obtain the title compound as white powder (79.6 mg, yield: 63%).

$^1$H-NMR (400 MHz, CDCl$_3$) δ ppm: 8.58 (1H, d, J=9 Hz), 8.51 (1H, brs), 7.79 (1H, dd, J=9 Hz, 2 Hz), 7.72 (1H, brs), 5.99 (1H, s), 5.37-5.31 (1H, m), 4.28-4.25 (2H, m), 4.07 (2H, t, J=9 Hz), 3.88-3.82 (2H, m), 3.64-3.61 (2H, m), 3.41-3.30 (4H, m), 3.41 (3H, s), 3.05 (3H, s), 2.05-1.98 (2H, m), 1.81-1.72 (4H, m);

MS (CI) m/z: 477 [M+H]$^+$.

Example 9 sec-butyl 4-({6-[5-(methylsulfonyl)indolin-1-yl]pyrimidin-4-yl}oxy)piperidine-1-carboxylate (exemplary compound No: 7)

Potassium tert-butoxide (174 mg, 1.55 mmol) was added to a THF (3.5 mL) solution of 2-butanol (86 mg, 0.93 mmol), and the mixture was stirred at room temperature for 30 minutes. Then, a THF (3 mL) solution of the 1-(6-{[1-(1H-imidazol-1-ylcarbonyl)piperidin-4-yl]oxy}pyrimidin-4-yl)-5-(methylsulfonyl)indoline (150 mg, 0.311 mmol) produced in Reference Example 29 was added thereto, and the mixture was stirred at room temperature for 2 hours. To the reaction solution, a saturated aqueous solution of ammonium chloride and water were added, followed by extraction with ethyl acetate three times. The obtained organic layer was washed with saturated saline and dried over anhydrous magnesium sulfate, and the solvent was distilled off under reduced pressure. The obtained residue was purified by silica gel column chromatography (hexane:ethyl acetate=5:1-1:2, V/V) to obtain the title compound as white foam (20.0 mg, yield: 14%).

$^1$H-NMR (500 MHz, CDCl$_3$) δ ppm: 8.59 (1H, d, J=9 Hz), 8.52 (1H, s), 7.80 (1H, dd, J=9 Hz, 2 Hz), 7.73 (1H, d, J=2 Hz), 5.99 (1H, d, J=1 Hz), 5.37-5.32 (1H, m), 4.80-4.76 (1H, m), 4.08 (2H, t, J=9 Hz), 3.87-3.82 (2H, m), 3.37-3.30 (4H, m), 3.05 (3H, s), 2.04-1.99 (2H, m), 1.79-1.71 (2H, m), 1.55 (2H, m), 1.24 (3H, d, J=6 Hz), 0.93 (3H, t, J=7 Hz);

MS (CI) m/z: 475 [M+H]$^+$.

Example 10

2-cyclopropylethyl 4-({6-[5-(methylsulfonyl)indolin-1-yl]pyrimidin-4-yl}oxy)piperidine-1-carboxylate (exemplary compound No: 30)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (150 mg, 0.311 mmol) produced in Reference Example 29 and, instead of 2-butanol, 2-cyclopropylethanol (56 μL, 0.93 mmol) to obtain the title compound as white powder (44.7 mg, yield: 30%).

$^1$H-NMR (400 MHz, CDCl$_3$) δ ppm: 8.58 (1H, d, J=9 Hz), 8.51 (1H, s), 7.79 (1H, dd, J=9 Hz, 2 Hz), 7.73-7.72 (1H, m), 5.99 (1H, s), 5.37-5.31 (1H, m), 4.18 (2H, t, J=7 Hz), 4.07 (2H, t, J=9 Hz), 3.88-3.81 (2H, m), 3.40-3.30 (4H, m), 3.05 (3H, s), 2.06-1.99 (2H, m), 1.80-1.73 (2H, m), 1.58-1.53 (2H, m), 0.76-0.70 (1H, m), 0.49-0.45 (2H, m), 0.11-0.07 (2H, m);

MS (CI) m/z: 487 [M+H]$^+$.

Example 11

(1-methylcyclopropyl)methyl 4-({6-[5-(methylsulfonyl)indolin-1-yl]pyrimidin-4-yl}oxy)piperidine-1-carboxylate (exemplary compound No: 24)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (150 mg, 0.311 mmol) produced in Reference Example 29 and, instead of 2-butanol, (1-methylcyclopropyl)methanol (91 μL, 0.93 mmol) to obtain the title compound as white powder (50.3 mg, yield: 33%).

$^1$H-NMR (500 MHz, CDCl$_3$) δ ppm: 8.58 (1H, d, J=9 Hz), 8.52 (1H, d, J=1 Hz), 7.79 (1H, dd, J=9 Hz, 2 Hz), 7.72 (1H, brs), 5.99 (1H, d, J=1 Hz), 5.38-5.32 (1H, m), 4.07 (2H, t, J=9 Hz), 3.90 (2H, s), 3.90-3.83 (2H, m), 3.41-3.29 (4H, m), 3.04 (3H, s), 2.06-2.00 (2H, m), 1.81-1.72 (2H, m), 1.14 (3H, s), 0.51-0.48 (2H, m), 0.37-0.34 (2H, m);

MS (CI) m/z: 487 [M+H]$^+$.

Example 12

2,2-difluoroethyl 4-({6-[5-(methylsulfonyl)indolin-1-yl]pyrimidin-4-yl}oxy)piperidine-1-carboxylate (exemplary compound No: 53)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl) indoline (150 mg, 0.311 mmol) produced in Reference Example 29 and, instead of 2-butanol, 2,2-difluoroethanol (76.5 mg, 0.933 mmol) to obtain the title compound as white powder (105 mg, yield: 70%).

$^1$H-NMR (500 MHz, CDCl$_3$) δ ppm: 8.58 (1H, d, J=9 Hz), 8.51 (1H, s), 7.79 (1H, dd, J=9 Hz, 2 Hz), 7.72 (1H, brs), 5.99 (1H, s), 5.97 (1H, tt, J=55 Hz, 4 Hz), 5.38-5.34 (1H, m), 4.30 (2H, td, J=14 Hz, 4 Hz), 4.07 (2H, t, J=9 Hz), 3.85-3.79 (2H, m), 3.45-3.40 (2H, m), 3.32 (2H, t, J=9 Hz), 3.04 (3H, s), 2.06-1.99 (2H, m), 1.82-1.75 (2H, m);

MS (CI) m/z: 483 [M+H]$^+$.

Example 13 cycloheptyl 4-({6-[5-(methylsulfonyl)indolin-1-yl]pyrimidin-4-yl}oxy)piperidine-1-carboxylate (exemplary compound No: 23)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl) indoline 150 mg, 0.311 mmol) produced in Reference Example 29 and, instead of 2-butanol, cycloheptanol (149 μL, 1.24 mmol) to obtain a crude product. The obtained crude product was purified by preparative HPLC [Inertsil ODS-3 (30 mm i.d.×250 mm), GL Sciences Inc., water:acetonitrile=95:5-0:100 (gradient)] to obtain the title compound as white powder (18.0 mg, yield: 8%).

$^1$H-NMR (500 MHz, CDCl$_3$) δ ppm: 8.58 (1H, d, J=9 Hz), 8.52 (1H, s), 7.80 (1H, dd, J=9 Hz, 2 Hz), 7.73 (1H, brs), 5.99 (1H, s), 5.36-5.32 (1H, m), 4.90-4.85 (1H, m), 4.07 (2H, t, J=9 Hz), 3.87-3.83 (2H, m), 3.37-3.30 (4H, m), 3.05 (3H, s), 2.03-2.00 (2H, m), 1.95-1.89 (2H, m), 1.75-1.45 (12H, m);

MS (CI) m/z: 515 [M+H]$^+$.

Example 14 cyclohexyl 4-({6-[5-(methylsulfonyl)indolin-1-yl]pyrimidin-4-yl}oxy)piperidine-1-carboxylate (exemplary compound No: 22)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl) indoline (150 mg, 0.311 mmol) produced in Reference Example 29 and, instead of 2-butanol, cyclohexanol (131 μL, 1.24 mmol) to obtain a crude product. The obtained crude product was purified by preparative HPLC [Inertsil ODS-3 (30' mm i.d.×250 mm), GL Sciences Inc., water:acetonitrile=95:5-0:100 (gradient)] to obtain the title compound as white powder (22.2 mg, yield: 11%).

$^1$H-NMR (400 MHz, CDCl$_3$) δ ppm: 8.58 (1H, d, J=9 Hz), 8.51 (1H, d, J=1 Hz), 7.79 (1H, dd, J=9 Hz, 2 Hz), 7.72 (1H, d, J=2 Hz), 5.98 (1H, d, J=1 Hz), 5.36-5.31 (1H, m), 4.73-4.67 (1H, m), 4.07 (2H, t, J=9 Hz), 3.87-3.81 (2H, m), 3.37-3.29 (4H, m), 3.04 (3H, s), 2.05-1.98 (2H, m), 1.90-1.84 (2H, m), 1.79-1.68 (4H, m), 1.55-1.25 (6H, m);

MS (FAB) m/z: 501 [M+H]$^+$.

Example 15

1-cyclopropylethyl 4-({6-[5-(methylsulfonyl)indolin-1-yl]pyrimidin-4-yl}oxy)piperidine-1-carboxylate (exemplary compound No: 28)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl) indoline (150 mg, 0.311 mmol) produced in Reference Example 29 and, instead of 2-butanol, 1-cyclopropylethanol (90 μL, 0.93 mmol) to obtain the title compound as white foam (56.1 mg, yield: 37%).

$^1$H-NMR (500 MHz, CDCl$_3$) δ ppm: 8.58 (1H, d, J=9 Hz), 8.51 (1H, d, J=1 Hz), 7.79 (1H, dd, J=9 Hz, 2 Hz), 7.72 (1H, d, J=2 Hz), 5.98 (1H, d, J=1 Hz), 5.37-5.31 (1H, m), 4.09 (2H, t, J=9 Hz), 3.88-3.82 (2H, m), 3.38-3.29 (4H, m), 3.04 (3H, s), 2.05-1.98 (2H, m), 1.79-1.71 (2H, m), 1.32 (3H, d, J=6 Hz), 1.02-0.94 (1H, m), 0.54-0.39 (3H, m), 0.27-0.22 (1H, m);

MS (CI) m/z: 487 [M+H]$^+$.

Example 16

2-furylmethyl 4-({6-[5-(methylsulfonyl)indolin-1-yl]pyrimidin-4-yl}oxy)piperidine-1-carboxylate (exemplary compound No: 25)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl) indoline (150 mg, 0.311 mmol) produced in Reference Example 29 and, instead of 2-butanol, 2-furylmethanol (81 μL, 0.93 mmol) to obtain the title compound as white foam (18.0 mg, yield: 2%).

$^1$H-NMR (400 MHz, CDCl$_3$) δ ppm: 8.57 (1H, d, J=9 Hz), 8.50 (1H, d, J=1 Hz), 7.78 (1H, dd, J=9 Hz, 2 Hz), 7.72 (1H, brs), 6.42-6.36 (2H, m), 5.97 (1H, d, J=1 Hz), 5.36-5.30 (1H, m), 5.09 (2H, s), 4.06 (2H, t, J=9 Hz), 3.86-3.77 (2H, m), 3.40-3.29 (4H, m), 3.04 (3H, s), 2.05-1.86 (2H, m), 1.80-1.70 (2H, m);

MS (CI) m/z: 499 [M+H]$^+$.

Example 17 dicyclopropylmethyl 4-({6-[5-(methylsulfonyl)indolin-1-yl]pyrimidin-4-yl}oxy)piperidine-1-carboxylate (exemplary compound No: 29)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl) indoline (150 mg, 0.311 mmol) produced in Reference Example 29 and, instead of 2-butanol, dicyclopropylmethanol (72 μL, 0.93 mmol) to obtain the title compound as white powder (45.7 mg, yield: 29%).

$^1$H-NMR (400 MHz, CDCl$_3$) δ ppm: 8.58 (1H, d, J=9 Hz), 8.51 (1H, d, J=1 Hz), 7.79 (1H, dd, J=9 Hz, 2 Hz), 7.72 (1H, brs), 5.99 (1H, s), 5.37-5.32 (1H, m), 4.07 (2H, t, J=9 Hz), 3.91-3.83 (3H, m), 3.38-3.29 (4H, m), 3.04 (3H, s), 2.05-1.99 (2H, m), 1.80-1.71 (2H, m), 1.11-1.04 (2H, m), 0.58-0.41 (6H, m), 0.36-0.30 (2H, m);
MS (FAB) m/z: 513 [M+H]$^+$.

Example 18

1-phenylethyl 4-({6-[5-(methylsulfonyl)indolin-1-yl]pyrimidin-4-yl}oxy)piperidine-1-carboxylate (exemplary compound No: 52)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (150 mg, 0.311 mmol) produced in Reference Example 29 and, instead of 2-butanol, DL-1-phenylethanol (113 µL, 0.933 mmol) to obtain the title compound as white powder (60.5 mg, yield: 37%).

$^1$H-NMR (500 MHz, CDCl$_3$) δ ppm: 8.58 (1H, d, J=9 Hz), 8.51 (1H, s), 7.79 (1H, dd, J=9 Hz, 2 Hz), 7.73 (1H, brs), 7.37-7.36 (5H, m), 5.98 (1H, s), 5.84 (1H, q, J=6 Hz), 5.36-5.32 (1H, m), 4.07 (2H, t, J=9 Hz), 3.90-3.83 (2H, m), 3.44-3.30 (4H, m), 3.05 (3H, s), 2.04-1.99 (2H, m), 1.80-1.72 (2H, m), 1.56 (3H, d, J=6 Hz);
MS (CI) m/z: 523 [M+H]$^+$.

Example 19

3-furylmethyl 4-({6-[5-(methylsulfonyl)indolin-1-yl]pyrimidin-4-yl}oxy)piperidine-1-carboxylate (exemplary compound No: 26)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (150 mg, 0.311 mmol) produced in Reference Example 29 and, instead of 2-butanol, 3-furylmethanol (81 µL, 0.93 mmol) to obtain the title compound as white foam (11.6 mg, yield: 7%).

$^1$H-NMR (400 MHz, CDCl$_3$) δ ppm: 8.58 (1H, d, J=9 Hz), 8.50 (1H, d, J=1 Hz), 7.79 (1H, dd, J=9 Hz, 2 Hz), 7.72 (1H, brs), 7.48 (1H, brs), 7.41-7.40 (1H, m), 6.45 (1H, brs), 5.98 (1H, s), 5.36-5.31 (1H, m), 5.02 (2H, s), 4.06 (2H, t, J=9 Hz), 3.86-3.78 (2H, m), 3.40-3.29 (4H, m), 3.04 (3H, s), 2.05-1.97 (2H, m), 1.79-1.71 (2H, m);
MS (FAB) m/z: 499 [M+H]$^+$.

Example 20 cyclopentylmethyl 4-({6-[5-(methylsulfonyl)indolin-1-yl]pyrimidin-4-yl}oxy)piperidine-1-carboxylate (exemplary compound No: 21)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (150 mg, 0.311 mmol) produced in Reference Example 29 and, instead of 2-butanol, cyclopentylmethanol (101 µL, 0.933 mmol) to obtain the title compound as white powder (36.8 mg, yield: 24%).

$^1$H-NMR (500 MHz, CDCl$_3$) δ ppm: 8.58 (1H, d, J=9 Hz), 8.50 (1H, d, J=1 Hz), 7.78 (1H, dd, J=9 Hz, 2 Hz), 7.72 (1H, d, J=2 Hz), 5.98 (1H, s), 5.36-5.31 (1H, m), 4.07 (2H, t, J=9 Hz), 3.98 (2H, d, J=7 Hz), 3.86-3.81 (2H, m), 3.38-3.29 (4H, m), 3.04 (3H, s), 2.22 (1H, quintet, J=7 Hz), 2.05-1.98 (2H, m), 1.79-1.64 (8H, m), 1.32-1.25 (2H, m);
MS (CI) m/z: 501 [M+H]$^+$.

Example 21

2-fluoro-1-(fluoromethyl)ethyl 4-({6-[5-(methylsulfonyl)indolin-1-yl]pyrimidin-4-yl}oxy)piperidine-1-carboxylate (exemplary compound No: 55)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (150 mg, 0.311 mmol) produced in Reference Example 29 and, instead of 2-butanol, 1,3-difluoropropan-2-ol (72 µL, 0.93 mmol) to obtain the title compound as white powder (65.8 mg, yield: 43%).

$^1$H-NMR (400 MHz, CDCl$_3$) δ ppm: 8.58 (1H, d, J=9 Hz), 8.51 (1H, d, J=1 Hz), 7.79 (1H, dd, J=9 Hz, 2 Hz), 7.73 (1H, d, J=2 Hz), 5.98 (1H, s), 5.39-5.33 (1H, m), 5.15 (1H, tt, J=20 Hz, 5 Hz), 4.70-4.57 (4H, m), 4.07 (2H, t, J=9 Hz), 3.86-3.80 (2H, m), 3.45-3.39 (2H, m), 3.32 (2H, t, J=9 Hz), 3.04 (3H, s), 2.06-2.00 (2H, m), 1.83-1.76 (2H, m);
MS (CI) m/z: 497 [M+H]$^+$.

Example 22 isobutyl 4-({6-[5-(ethylsulfonyl)indolin-1-yl]pyrimidin-4-yl}oxy)piperidine-1-carboxylate (exemplary compound No: 307)

The same reaction as in the method described in Example 2 was performed using tert-butyl 4-({6-[5-(ethylsulfonyl)indolin-1-yl]pyrimidin-4-yl}oxy)piperidine-1-carboxylate (154 mg, 0.315 mmol) produced in Example 30 and, instead of isopropyl chloroformate and triethylamine, isobutyl chloroformate (130 µL, 1.00 mmol) and diisopropylethylamine (560 µL, 3.14 mmol), respectively, to obtain the title compound as grayish white powder (94.2 mg, yield: 61%).

$^1$H-NMR (500 MHz, CDCl$_3$) δ ppm: 8.57 (1H, d, J=9 Hz), 8.51 (1H, d, J=1 Hz), 7.75 (1H, dd, J=8 Hz, 2 Hz), 7.68 (1H, d, J=2 Hz), 5.98 (1H, d, J=1 Hz), 5.36-5.32 (1H, m), 4.07 (2H, t, J=9 Hz), 3.88 (2H, d, J=6 Hz), 3.88-3.82 (2H, m), 3.39-3.30 (4H, m), 3.10 (2H, q, J=7 Hz), 2.05-1.99 (2H, m), 1.95 (1H, sept, J=7 Hz), 1.79-1.72 (2H, m), 1.28 (3H, t, J=7 Hz), 0.95 (6H, d, J=7 Hz);
MS (ESI) m/z: 489 [M+H]$^+$.

Example 23 cyclobutyl 4-({6-[5-(ethylsulfonyl)indolin-1-yl]pyrimidin-4-yl}oxy)piperidine-1-carboxylate (exemplary compound No: 310)

Cyclobutanol (90 µL, 1.15 mmol) and potassium tert-butoxide (50 mg, 0.446 mmol) were added to a THF (2.5 mL) suspension of the 5-(ethylsulfonyl)-1-(6-{[1-(1H-imidazol-1-ylcarbonyl)piperidin-4-yl]oxy}pyrimidin-4-yl)indoline (109 mg, 0.226 mmol) produced in Reference Example 31, and the mixture was stirred at room temperature for 1 hour. To the reaction solution, water was added, followed by extraction with ethyl acetate three times. The obtained organic layer was washed with water and saturated saline and dried over anhydrous magnesium sulfate, and the solvent was distilled off under reduced pressure. The obtained residue was purified by silica gel column chromatography [(i) hexane:ethyl acetate=50:50, V/V; (ii) ethyl acetate]. The obtained crude product was washed with diisopropyl ether to obtain the title compound as white powder (34.6 mg, yield: 32%).

$^1$H-NMR (400 MHz, CDCl$_3$) δ ppm: 8.58 (1H, d, J=9 Hz), 8.51 (1H, d, J=1 Hz), 7.75 (1H, dd, J=9 Hz, 2 Hz), 7.68 (1H, d, J=2 Hz), 5.98 (1H, d, J=1 Hz), 5.36-5.30 (1H, m), 4.98-4.91 (1H, m), 4.07 (2H, t, J=9 Hz), 3.85-3.80 (2H, m), 3.38-3.29 (4H, m), 3.10 (2H, q, J=7 Hz), 2.39-2.31 (2H, m), 2.12-1.98 (4H, m), 1.81-1.55 (4H, m), 1.28 (3H, t, J=7 Hz);

MS (ESI) m/z: 487 [M+H]$^+$.

Example 24 sec-butyl 4-({6-[5-(ethylsulfonyl)indolin-1-yl]pyrimidin-4-yl}oxy)piperidine-1-carboxylate (exemplary compound No: 308)

The same reaction as in the method described in Example 23 was performed using the 5-(ethylsulfonyl)-1-(6-{[1-(1H-imidazol-1-ylcarbonyl)piperidin-4-yl]oxy}pyrimidin-4-yl)indoline (179 mg, 0.371 mmol) produced in Reference Example 31 and, instead of cyclobutanol, 2-butanol (170 μL, 1.85 mmol) to obtain the title compound as white foam (55.1 mg, yield: 30%).

$^1$H-NMR (400 MHz, CDCl$_3$) δ ppm: 8.58 (1H, d, J=9 Hz), 8.51 (1H, d, J=1 Hz), 7.75 (1H, dd, J=9 Hz, 2 Hz), 7.68 (1H, d, J=2 Hz), 5.98 (1H, d, J=1 Hz), 5.37-5.31 (1H, m), 4.77 (1H, sext, J=6 Hz), 4.07 (2H, t, J=9 Hz), 3.87-3.82 (2H, m), 3.37-3.25 (4H, m), 3.10 (2H, q, J=7 Hz), 2.04-1.99 (2H, m), 1.79-1.73 (2H, m), 1.66-1.52 (2H, m), 1.28 (3H, t, J=7 Hz), 1.23 (3H, d, J=6 Hz), 0.92 (3H, t, J=7 Hz);

MS (ESI) m/z: 489 [M+H]$^+$.

Example 25 tert-butyl 4-({6-[5-(isobutylsulfonyl)indolin-1-yl]pyrimidin-4-yl}oxy)piperidine-1-carboxylate (exemplary compound No: 481)

Palladium acetate (11.3 mg, 0.0503 mmol) was added to a 1,4-dioxane (7.5 mL) solution of 2-dicyclohexylphosphino-2'-(N,N-dimethylamino)biphenyl (37.2 mg, 0.0945 mmol), and the mixture was stirred at room temperature for 10 minutes. The solution was added to a 1,4-dioxane (7.5 mL) suspension of the tert-butyl 4-[(6-chloro-5-methylpyrimidin-4-yl)oxy]piperidine-1-carboxylate (143 mg, 0.456 mmol) produced in Reference Example 41, the 5-isobutanesulfonylindoline hydrochloride (123 mg, 0.446 mmol) produced in Reference Example 11, and potassium carbonate (1.12 g, 8.10 mmol), and the mixture was stirred at 100° C. for 1 hour and at 120° C. for 1 hour. The reaction solution was filtered through Celite (trade name). The filtrate was washed with 10% hydrochloric acid, water, and saturated saline and dried over anhydrous magnesium sulfate, and the solvent was distilled off under reduced pressure. The obtained residue was purified by silica gel column chromatography [(i) hexane: ethyl acetate=50:50, V/V; (ii) ethyl acetate] and thin-layer silica gel chromatography (hexane:ethyl acetate=1:1, V/V) to obtain the title compound as white powder (12.6 mg, yield: 5%).

$^1$H-NMR (400 MHz, CDCl$_3$) δ ppm: 8.57 (1H, d, J=9 Hz), 8.51 (1H, d, J=1 Hz), 7.75 (1H, dd, J=9 Hz, 2 Hz), 7.68 (1H, d, J=2 Hz), 5.98 (1H, d, J=1 Hz), 5.35-5.28 (1H, m), 4.06 (2H, t, J=9 Hz), 3.82-3.77 (2H, m), 3.33-3.25 (4H, m), 2.97 (2J, d, J=6 Hz), 2.25-2.17 (1H, m), 2.03-1.97 (2H, m), 1.77-1.69 (2H, m), 1.48 (9H, s), 1.05 (6H, d, J=7 Hz);

MS (ESI) m/z: 517 [M+H]$^+$.

Example 26 tert-butyl 4-({5-methyl-6-[5-(methylsulfonyl)indolin-1-yl]pyrimidin-4-yl}oxy)piperidine-1-carboxylate (exemplary compound No: 202)

The same reaction as in the method described in Example 25 was performed using the tert-butyl 4-[(6-chloro-5-methylpyrimidin-4-yl)oxy]piperidine-1-carboxylate (291 mg, 0.888 mmol) produced in Reference Example 40 and 5-methanesulfonylindoline (162 mg, 0.821 mmol) to obtain the title compound as white powder (365 mg, yield: 91%).

$^1$H-NMR (400 MHz, CDCl$_3$) δ ppm: 8.43 (1H, s), 7.71-7.67 (2H, m), 6.70 (1H, d, J=8 Hz), 5.40-5.34 (1H, m), 4.20 (2H, t, J=9 Hz), 3.78-3.72 (2H, m), 3.42-3.35 (2H, m), 3.22 (2H, t, J=8 Hz), 3.03 (3H, s), 2.05 (3H, s), 2.05-1.99 (2H, m), 1.84-1.76 (2H, m), 1.49 (9H, s);

MS (ESI) m/z: 489 [M+H]$^+$.

Example 27 isobutyl 4-({6-[5-(propylsulfonyl)indolin-1-yl]pyrimidin-4-yl}oxy)piperidine-1-carboxylate (exemplary compound No: 390)

The same reaction as in the method described in Example 6 was performed using the 1-[6-(piperidin-4-yloxy)pyrimidin-4-yl]-5-(propylsulfonyl)indoline hydrochloride (199 mg, 0.453 mmol) produced in Reference Example 32 and, instead of butyl chloroformate, isobutyl chloroformate to obtain the title compound as white foam (193 mg, yield: 85%).

$^1$H-NMR (400 MHz, CDCl$_3$) δ ppm: 8.57 (1H, d, J=9 Hz), 8.51 (1H, s), 7.75 (1H, dd, J=9 Hz, 2 Hz), 7.68 (1H, s), 5.98 (1H, s), 5.37-5.31 (1H, m), 4.06 (2H, t, J=9 Hz), 3.88 (2H, d, J=7 Hz), 3.88-3.81 (2H, m), 3.39-3.29 (4H, m), 3.07-3.03 (2H, m), 2.05-1.90 (3H, m), 1.80-1.69 (4H, m), 0.99 (3H, t, J=7 Hz), 0.95 (6H, d, J=7 Hz);

MS (ESI) m/z: 503 [M+H]$^+$.

Example 28 isopropyl 4-({5-methyl-6-[5-(methylsulfonyl)indolin-1-yl]pyrimidin-4-yl}oxy)piperidine-1-carboxylate (exemplary compound No: 200)

The same reaction as in the method described in Example 2 was performed using the tert-butyl 4-({5-methyl-6-[5-(methylsulfonyl)indolin-1-yl]pyrimidin-4-yl}oxy)piperidine-1-carboxylate (208 mg, 0.426 mmol) produced in Example 26 and, instead of triethylamine, diisopropylethylamine (380 μL, 2.13 mmol) to obtain the title compound as white foam (177 mg, yield: 88%).

$^1$H-NMR (400 MHz, CDCl$_3$) δ ppm: 8.43 (1H, s), 7.71-7.67 (2H, m), 6.70 (1H, d, J=8 Hz), 5.42-5.36 (1H, m), 4.95 (1H, sept, J=6 Hz), 4.19 (2H, t, J=8 Hz), 3.81-3.76 (2H, m), 3.46-3.40 (2H, m), 3.22 (2H, t, J=8 Hz), 3.03 (3H, s), 2.06-2.00 (2H, m), 2.05 (3H, s), 1.85-1.77 (2H, m), 1.27 (6H, d, J=6 Hz);

MS (FAB) m/z: 475 [M+H]$^+$.

Example 29

2,2,2-trifluoroethyl 4-({6-[5-(isobutylsulfonyl)indolin-1-yl]pyrimidin-4-yl}oxy)piperidine-1-carboxylate (exemplary compound No: 486)

The same reaction as in the method described in Example 23 was performed using the 1-(6-{[1-(1H-imidazol-1-ylcarbonyl)piperidin-4-yl]oxy}pyrimidin-4-yl)-5-(isobutylsulfonyl)indoline (260 mg, 0.509 mmol) produced in Reference Example 37 and, instead of cyclobutanol, 2,2,2-trifluoroethanol (185 μL, 2.54 mmol) to obtain the title compound as white powder (217 mg, yield: 79%).

$^1$H-NMR (400 MHz, CDCl$_3$) δ ppm: 8.57 (1H, d, J=9 Hz), 8.51 (1H, s), 7.75 (1H, dd, J=9 Hz, 2 Hz), 7.69 (1H, s), 5.99 (1H, s), 5.40-5.34 (1H, m), 4.54-4.47 (2H, m), 4.07 (2H, t, J=8 Hz), 3.86-3.80 (2H, m), 3.48-3.42 (2H, m), 3.31 (2H, t, J=9 Hz), 2.97 (2H, d, J=7 Hz), 2.26-2.16 (1H, m), 2.06-2.01 (2H, m), 1.84-1.77 (2H, m), 1.05 (6H, d, J=7 Hz);

MS (ESI) m/z: 543 [M+H]$^+$.

Example 30 tert-butyl 4-({6-[5-(ethylsulfonyl)indolin-1-yl]pyrimidin-4-yl}oxy)piperidine-1-carboxylate (exemplary compound No: 309)

The same reaction as in the method described in Example 1 was performed using the 1-(6-chloropyrimidin-4-yl)-5-(ethylsulfonyl)indoline (114 mg, 0.551 mmol) produced in Reference Example 20 to obtain the title compound as white powder (79.0 mg, yield: 35%).

$^1$H-NMR (500 MHz, DMSO-d$_6$) δ ppm: 8.55 (1H, d, J=9 Hz), 8.54 (1H, s), 7.69 (1H, d, J=9 Hz), 7.68 (1H, s), 6.23 (1H, s), 5.29-5.24 (1H, m), 4.09 (2H, t, J=9 Hz), 4.03 (2H, q, J=7 Hz), 3.71 (2H, dt, J=14 Hz, 5 Hz), 3.28 (2H, t, J=9 Hz), 3.21 (2H, q, J=7 Hz), 1.99-1.95 (2H, m), 1.60-1.53 (2H, m), 1.41 (9H, s), 1.10 (3H, t, J=7 Hz);

MS (ESI) m/z: 489 [M+H]$^+$.

Example 31 isopropyl 4-({6-[5-(ethylsulfonyl)indolin-1-yl]pyrimidin-4-yl}oxy)piperidine-1-carboxylate (exemplary compound No: 305)

The same reaction as in the method described in Example 6 was performed using the 5-(ethylsulfonyl)-1-[6-(piperidin-4-yloxy)pyrimidin-4-yl]indoline (56.0 mg, 0.143 mmol) produced in Reference Example 30 and, instead of butyl chloroformate, isopropyl chloroformate (20.0 mg, 0.158 mmol) to obtain the title compound as white foam (65.0 mg, yield: 96%).

$^1$H-NMR (400 MHz, DMSO-d$_6$) δ ppm: 8.56 (1H, d, J=9 Hz), 8.54 (1H, s), 7.69 (1H, d, J=9 Hz), 7.68 (1H, s), 6.23 (1H, s), 5.31-5.25 (1H, m), 4.78 (1H, sept, J=6 Hz), 4.09 (2H, t, J=9 Hz), 3.74 (2H, dt, J=14 Hz, 6 Hz), 3.30-3.18 (6H, m), 2.01-1.94 (2H, m), 1.62-1.54 (2H, m), 1.20 (6H, d, J=6 Hz), 1.10 (3H, t, J=7 Hz);

MS (FAB) m/z: 475 [M+H]$^+$.

Example 32 tert-butyl 4-({6-[5-(isopropylsulfonyl)indolin-1-yl]pyrimidin-4-yl}oxy)piperidine-1-carboxylate (exemplary compound No: 414)

The same reaction as in the method described in Example 1 was performed using the 1-(6-chloropyrimidin-4-yl)-5-(isopropylsulfonyl)indoline (60.0 mg, 0.178 mmol) produced in Reference Example 22 to obtain the title compound as white powder (84.0 mg, yield: 94%).

$^1$H-NMR (400 MHz, DMSO-d$_6$) δ ppm: 8.56 (1H, d, J=9 Hz), 8.54 (1H, s), 7.65 (1H, d, J=9 Hz), 7.64 (1H, s), 6.24 (1H, s), 5.30-5.24 (1H, m), 4.09 (2H, t, J=9 Hz), 3.75-3.69 (2H, m), 3.41-3.25 (3H, m), 3.19-3.14 (2H, m), 1.99-1.95 (2H, m), 1.60-1.53 (2H, m), 1.41 (9H, s), 1.15 (6H, d, J=7 Hz);

MS (ESI) m/z: 503 [M+H]$^+$.

Example 33 isopropyl 4-({6-[5-(isopropylsulfonyl)indolin-1-yl]pyrimidin-4-yl}oxy)piperidine-1-carboxylate (exemplary compound No: 412)

The same reaction as in the method described in Example 28 was performed using the tert-butyl 4-({6-[5-(isopropylsulfonyl)indolin-1-yl]pyrimidin-4-yl}oxy)piperidine-1-carboxylate (80.0 mg, 0.159 mmol) produced in Example 32 to obtain the title compound as white foam (64.0 mg, yield: 82%).

$^1$H-NMR (400 MHz, DMSO-d$_6$) δ ppm: 8.56 (1H, d, J=9 Hz), 8.55 (1H, s), 7.66 (1H, d, J=9 Hz), 7.65 (1H, s), 6.24 (1H, s), 5.31-5.25 (1H, m), 4.78 (1H, sept, J=6 Hz), 4.10 (2H, t, J=9 Hz), 3.78-3.72 (2H, m), 3.38-3.19 (5H, m), 2.01-1.96 (2H, m), 1.63-1.54 (2H, m), 1.20 (6H, d, J=6 Hz), 1.16 (6H, d, J=7 Hz);

MS (FAB) m/z: 488 [M+H]$^+$.

Example 34 tert-butyl 4-({6-[6-fluoro-5-(methylsulfonyl)indolin-1-yl]pyrimidin-4-yl}oxy)piperidine-1-carboxylate (exemplary compound No: 133)

The same reaction as in the method described in Example 1 was performed using the 1-(6-chloropyrimidin-4-yl)-6-fluoro-5-(methylsulfonyl)indoline (286 mg, 0.873 mmol) produced in Reference Example 23 to obtain the title compound as white foam (141 mg, yield: 33%).

$^1$H-NMR (500 MHz, DMSO-d$_6$) δ ppm: 8.58 (1H, s), 8.38 (1H, d, J=13H), 7.62 (1H, d, J=8 Hz), 6.28 (1H, s), 5.30-5.25 (1H, m), 4.12 (2H, t, J=9 Hz), 3.73-3.69 (2H, m), 3.27-3.14 (7H, m), 1.99-1.95 (2H, m), 1.69-1.64 (2H, m), 1.38 (9H, s);

MS (ESI) m/z: 492 [M+H]$^+$.

Example 35 isopropyl 4-({6-[6-fluoro-5-(methylsulfonyl)indolin-1-yl]pyrimidin-4-yl}oxy)piperidine-1-carboxylate (exemplary compound No: 131)

The same reaction as in the method described in Example 28 was performed using the tert-butyl 4-({6-[6-fluoro-5-(methylsulfonyl)indolin-1-yl]pyrimidin-4-yl}oxy)piperidine-1-carboxylate (86.0 mg, 0.175 mmol) produced in Example 34 to obtain the title compound as white powder (56.0 mg, yield: 68%).

$^1$H-NMR (500 MHz, DMSO-d$_6$) δ ppm: 8.58 (1H, s), 8.37 (1H, d, J=13H), 7.62 (1H, d, J=7 Hz), 6.28 (1H, s), 5.31-5.26 (1H, m), 4.78 (1H, sept, J=6 Hz), 4.12 (2H, t, J=9 Hz), 3.74 (2H, dt, J=14 Hz, 5 Hz), 3.28 (2H, t, J=9 Hz), 3.25 (3H, s), 3.21-3.13 (2H, m), 2.00-1.94 (2H, m), 1.61-1.50 (2H, m), 1.41 (6H, d, J=6 Hz);

MS (FAB) m/z: 479 [M+H]$^+$.

Example 36 tert-butyl 4-({6-[5-(propylsulfonyl)indolin-1-yl]pyrimidin-4-yl}oxy)piperidine-1-carboxylate (exemplary compound No: 391)

The same reaction as in the method described in Example 1 was performed using the 1-(6-chloropyrimidin-4-yl)-5-

(propylsulfonyl)indoline (122 mg, 0.542 mmol) produced in Reference Example 21 to obtain the title compound as white powder (84.0 mg, yield: 46%).

$^1$H-NMR (400 MHz, DMSO-d$_6$) δ ppm: 8.55 (1H, d, J=9 Hz), 8.54 (1H, s), 7.69 (1H, d, J=9 Hz), 7.68 (1H, s), 6.23 (1H, s), 5.27 (1H, sept, J=4 Hz), 4.09 (2H, t, J=9 Hz), 3.72 (2H, dt, J=14 Hz, 5 Hz), 3.28 (2H, t, J=9 Hz), 3.21-3.13 (4H, m), 2.00-1.94 (2H, m), 1.61-1.50 (4H, m), 1.41 (9H, s), 0.91 (3H, t, J=7 Hz);

MS (ESI) m/z: 503 [M+H]$^+$.

Example 37

2,2-dimethylpropyl 4-({6-[5-(methylsulfonyl)indo-lin-1-yl]pyrimidin-4-yl}oxy)piperidine-1-carboxy-late (exemplary compound No: 18)

The same reaction as in the method described in Example 6 was performed using the 5-(methylsulfonyl)-1-[6-(piperi-din-4-yloxy)pyrimidin-4-yl]indoline (45.0 mg, 0.151 mmol) produced in Reference Example 28 and, instead of butyl chloroformate, neopentyl chloroformate (26 mg, 0.17 mmol) to obtain the title compound as white powder (32.0 mg, yield: 54%).

$^1$H-NMR (500 MHz, DMSO-d$_6$) δ ppm: 8.54 (1H, s), 8.54 (1H, d, J=9 Hz), 7.74 (1H, s), 7.73 (1H, d, J=9 Hz), 6.24 (1H, s), 5.32-5.27 (1H, m), 4.09 (2H, t, J=9 Hz), 3.77 (2H, brs), 3.72 (2H, s), 3.30-3.22 (4H, m), 3.15 (3H, s), 2.02-1.99 (2H, m), 1.63-1.57 (2H, m), 0.91 (9H, s);

MS (ESI) m/z: 489 [M+H]$^+$.

Example 38 phenyl 4-({6-[5-(methylsulfonyl)indolin-1-yl]pyri-midin-4-yl}oxy)piperidine-1-carboxylate (exemplary compound No: 46)

The same reaction as in the method described in Example 6 was performed using the 5-(methylsulfonyl)-1-[6-(piperi-din-4-yloxy)pyrimidin-4-yl]indoline (49.0 mg, 0.162 mmol) produced in Reference Example 28 and, instead of butyl chloroformate, phenyl chloroformate (28 mg, 0.18 mmol) to obtain the title compound as white powder (23.0 mg, yield: 36%).

$^1$H-NMR (500 MHz, DMSO-d$_6$) δ ppm: 8.56 (1H, s), 8.55 (1H, d, J=9 Hz), 7.74 (1H, s), 7.73 (1H, d, J=9 Hz), 7.39 (2H, t, J=7 Hz), 7.23 (1H, t, J=8 Hz), 7.14 (2H, d, J=8 Hz), 6.27 (1H, s), 5.38-5.33 (1H, m), 4.11 (2H, t, J=9 Hz), 3.95 (1H, brs), 3.81 (1H, brs), 3.50 (1H, brs), 3.37-3.27 (3H, m), 3.15 (3H, s), 2.09 (2H, brs), 1.73 (2H, brs);

MS (ESI) m/z: 495 [M+H]$^+$.

Example 39 isobutyl 4-({6-[5-(methylsulfonyl)indolin-1-yl]pyri-midin-4-yl}oxy)piperidine-1-carboxylate (exemplary compound No: 6)

The same reaction as in the method described in Example 6 was performed using the 5-(methylsulfonyl)-1-[6-(piperi-din-4-yloxy)pyrimidin-4-yl]indoline (47.0 mg, 0.154 mmol) produced in Reference Example 28 and, instead of butyl chloroformate, isobutyl chloroformate (23 mg, 0.17 mmol) to obtain the title compound as white powder (30.0 mg, yield: 51%).

$^1$H-NMR (500 MHz, DMSO-d$_6$) δ ppm: 8.54 (1H, s), 8.54 (1H, d, J=9 Hz), 7.73 (1H, s), 7.72 (1H, d, J=9 Hz), 6.24 (1H, s), 5.31-5.26 (1H, m), 4.09 (2H, t, J=9 Hz), 3.79 (2H, d, J=6 Hz), 3.79-3.74 (2H, m), 3.29-3.21 (4H, m), 3.15 (3H, s), 2.02-1.97 (2H, m), 1.87 (1H, sept, J=6 Hz), 1.63-1.56 (2H, m), 0.90 (6H, d, J=6 Hz);

MS (ESI) m/z: 475 [M+H]$^+$.

Example 40 isopropyl 4-({6-[5-(propylsulfonyl)indolin-1-yl]pyri-midin-4-yl}oxy)piperidine-1-carboxylate (exemplary compound No: 389)

The same reaction as in the method described in Example 28 was performed using the tert-butyl 4-({6-[5-(propylsulfo-nyl)indolin-1-yl]pyrimidin-4-yl}oxy)piperidine-1-carboxy-late (65.0 mg, 0.129 mmol) produced in Example 36 to obtain the title compound as white powder (42.0 mg, yield: 66%).

$^1$H-NMR (500 MHz, DMSO-d$_6$) δ ppm: 8.55 (1H, d, J=8 Hz), 8.54 (1H, s), 7.69 (1H, d, J=8 Hz), 7.68 (1H, s), 6.23 (1H, s), 5.30-5.26 (1H, m), 4.78 (1H, sept, J=6 Hz), 4.09 (2H, t, J=9 Hz), 3.77-3.72 (2H, m), 3.32-3.18 (6H, m), 2.00-1.95 (2H, m), 1.62-1.51 (4H, m), 1.19 (6H, d, J=6 Hz), 0.91 (3H, t, J=8 Hz);

MS (ESI) m/z: 489 [M+H]$^+$.

Example 41

5-(methylsulfonyl)-1-(6-{[1-(3,3,3-trifluoropro-panoyl)piperidin-4-yl]oxy}pyrimidin-4-yl)indoline (exemplary compound No: 81)

Oxalyl chloride (65 µL, 0.74 mmol) and a drop of DMF were added at 0° C. to a dichloromethane (1.9 mL) solution of 3,3,3-trifluoropropionic acid (63 mg, 0.50 mmol), and the mixture was stirred at room temperature for 3.5 hours. From the reaction solution, the solvent was then distilled off. The obtained residue is referred to as an acid chloride compound.

Trifluoroacetic acid (2.35 mL) was added at 0° C. to a dichloromethane (9.38 mL) solution of the tert-butyl 4-({6-[5-(methylsulfonyl)indolin-1-yl]pyrimidin-4-yl}oxy)piperi-dine-1-carboxylate (469 mg, 0.988 mmol) produced in Example 1, and the mixture was stirred at room temperature for 1 hour. From the reaction solution, the solvent was then distilled off. To a THF (450 µL) solution of a portion (150 mg) of the obtained residue and diisopropylethylamine (431 µL, 2.48 mmol), a THF (3.0 mL) solution of the preceding pro-duced acid chloride compound was added at 0° C., and the mixture was stirred at room temperature for 3 hours. To the reaction solution, a saturated aqueous solution of ammonium chloride and water were added, followed by extraction with ethyl acetate three times. The obtained organic layer was dried over anhydrous sodium sulfate, and the solvent was distilled off under reduced pressure. The obtained residue was purified by preparative thin-layer silica gel chromatography (hexane:ethyl acetate=1:2, V/V) to obtain the title compound as white foam (13 mg, yield: 11%).

$^1$H-NMR (500 MHz, DMSO-d$_6$) δ ppm: 8.55 (1H, s), 8.55 (1H, d, J=9 Hz), 7.74 (1H, s), 7.73 (1H, d, J=9 Hz), 6.25 (1H, s), 5.35-5.31 (1H, m), 4.09 (2H, t, J=9 Hz), 3.95-3.90 (1H, m), 3.74-3.66 (3H, m), 3.40-3.35 (1H, m), 3.30-3.25 (3H, m), 3.15 (3H, s), 2.06-1.96 (2H, m), 1.72-1.65 (1H, m), 1.61-1.54 (1H, m);

MS (FAB) m/z: 485 [M+H]$^+$.

Example 42

1-(6-{[1-(butylsulfonyl)piperidin-4-yl]oxy}pyrimidin-4-yl)-5-(methylsulfonyl)indoline (exemplary compound No: 126)

Trifluoroacetic acid (727 μL) was added at 0° C. to a dichloromethane (2.90 mL) solution of the tert-butyl 4-({6-[5-(methylsulfonyl)indolin-1-yl]pyrimidin-4-yl}oxy)piperidine-1-carboxylate (145 mg, 0.306 mmol) produced in Example 1, and the mixture was stirred at room temperature for 1 hour. The solvent was distilled off under reduced pressure. To a dichloromethane (3.70 mL) solution of the obtained residue and diisopropylethylamine (1.07 mL, 6.14 mmol), a dichloromethane (1.85 mL) solution of 1-butanesulfonyl chloride (72.0 mg, 0.461 mmol) was added at 0° C., and the mixture was stirred at 0° C. for 1 hour and then at 80° C. for 3 hours. The solvent was distilled off under reduced pressure. To the residue, methanol was added, and the deposit was collected by filtration. The obtained crude product was washed with methanol to obtain the title compound as white powder (125 mg, yield: 82%).

$^1$H-NMR (400 MHz, DMSO-$d_6$) δ ppm: 8.55 (1H, s), 8.54 (1H, d, J=9 Hz), 7.74 (1H, s), 7.73 (1H, d, J=9 Hz), 6.25 (1H, s), 5.29-5.22 (1H, m), 4.10 (2H, t, J=9 Hz), 3.49-3.43 (2H, m), 3.28 (2H, t, J=9 Hz), 3.21-3.15 (2H, m), 3.15 (3H, s), 3.08-3.04 (2H, m), 2.10-2.03 (2H, m), 1.78-1.62 (4H, m), 1.46-1.37 (2H, m), 0.91 (3H, t, J=7 Hz);

MS (FAB) m/z: 495 [M+H]$^+$.

Example 43 isopropyl 4-({6-[6-chloro-5-(methylsulfonyl)indolin-1-yl]pyrimidin-4-yl}oxy)piperidine-1-carboxylate (exemplary compound No: 155)

The same reaction as in the method described in Example 1 was performed using the 6-chloro-1-(6-chloropyrimidin-4-yl)-5-(methylsulfonyl)indoline (353 mg, 1.03 mmol) produced in Reference Example 24 and, instead of tert-butyl 4-hydroxypiperidine-1-carboxylate, isopropyl 4-hydroxypiperidine-1-carboxylate (288 mg, 1.54 mmol) to obtain the title compound as white powder (446 mg, yield: 88%).

$^1$H-NMR (500 MHz, DMSO-$d_6$) δ ppm: 8.65 (1H, s), 8.60 (1H, s), 7.83 (1H, s), 6.27 (1H, s), 5.31-5.26 (1H, m), 4.78 (1H, sept, J=6 Hz), 4.11 (2H, t, J=9 Hz), 3.74 (2H, dt, J=13 Hz, 5 Hz), 3.30 (3H, s), 3.29-3.18 (4H, m), 2.00-1.96 (2H, m), 1.61-1.55 (2H, m), 1.20 (6H, d, J=6 Hz);

MS (FAB) m/z: 495 [M+H]$^+$.

Example 44 cyclopropylmethyl 4-({6-[5-(methylsulfonyl)indolin-1-yl]pyrimidin-4-yl}oxy)piperidine-1-carboxylate (exemplary compound No: 19)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (102 mg, 0.218 mmol) produced in Reference Example 29 and, instead of 2-butanol, cyclopropylmethanol (26 μL, 0.33 mmol) to obtain the title compound as white powder (49.0 mg, yield: 48%).

$^1$H-NMR (500 MHz, DMSO-$d_6$) δ ppm: 8.55 (1H, s), 8.54 (1H, d, J=9 Hz), 7.74-7.72 (2H, m), 6.24 (1H, s), 5.31-5.26 (1H, m), 4.09 (2H, t, J=9 Hz), 3.86 (2H, d, J=7 Hz), 3.76 (2H, dt, J=14 Hz, 5 Hz), 3.33-3.20 (4H, m), 3.15 (3H, s), 2.01-1.98 (2H, m), 1.64-1.57 (2H, m), 1.14-1.06 (1H, m), 0.52-0.48 (2H, m), 0.28-0.25 (2H, m);

MS (ESI) m/z: 473 [M+H]$^+$.

Example 45

1-{6-[(1-benzoylpiperidin-4-yl)oxy]pyrimidin-4-yl}-5-(methylsulfonyl)indoline (exemplary compound No: 84)

The same reaction as in the method described in Example 6 was performed using the 5-(methylsulfonyl)-1-[6-(piperidin-4-yloxy)pyrimidin-4-yl]indoline (50.0 mg, 0.134 mmol) produced in Reference Example 28 and, instead of butyl chloroformate, benzoyl chloride (19 μL, 0.16 mmol) to obtain the title compound as white powder (24.0 mg, yield: 38%).

$^1$H-NMR (500 MHz, DMSO-$d_6$) δ ppm: 8.55 (1H, s), 8.54 (1H, d, J=9 Hz), 7.74 (1H, s), 7.73 (1H, d, J=7 Hz), 7.46-7.45 (3H, m), 7.43-7.40 (2H, m), 6.24 (1H, s), 5.39-5.34 (1H, m), 4.09 (2H, t, J=9 Hz), 4.06 (1H, brs), 3.56 (1H, brs), 3.41 (1H, brs), 3.30-3.25 (3H, m), 3.15 (3H, s), 2.08 (1H, brs), 1.99 (1H, brs), 1.68 (2H, brs);

MS (ESI) m/z: 479 [M+H]$^+$.

Example 46 ethyl 4-({6-[5-(methylsulfonyl)indolin-1-yl]pyrimidin-4-yl}oxy)piperidine-1-carboxylate (exemplary compound No: 2)

The same reaction as in the method described in Example 6 was performed using the 5-(methylsulfonyl)-1-[6-(piperidin-4-yloxy)pyrimidin-4-yl]indoline (90.0 mg, 0.240 mmol) produced in Reference Example 28 and, instead of butyl chloroformate, ethyl chloroformate (34 μL, 0.36 mmol) to obtain the title compound as white powder (75.0 mg, yield: 70%).

$^1$H-NMR (500 MHz, DMSO-$d_6$) δ ppm: 8.54 (1H, s), 8.54 (1H, d, J=9 Hz), 7.74 (1H, s), 7.73 (1H, d, J=7 Hz), 6.24 (1H, s), 5.30-5.25 (1H, m), 4.09 (2H, t, J=8 Hz), 4.05 (2H, q, J=7 Hz), 3.75 (2H, dt, J=14 Hz, 5 Hz), 3.28 (2H, t, J=9 Hz), 3.24 (2H, brs), 3.15 (3H, s), 2.01-1.96 (2H, m), 1.63-1.56 (2H, m), 1.19 (3H, t, J=7 Hz);

MS (ESI) m/z: 447 [M+H]$^+$.

Example 47

2-chloroethyl 4-({6-[5-(methylsulfonyl)indolin-1-yl]pyrimidin-4-yl}oxy)piperidine-1-carboxylate (exemplary compound No: 36)

The same reaction as in the method described in Example 6 was performed using the 5-(methylsulfonyl)-1-[6-(piperidin-4-yloxy)pyrimidin-4-yl]indoline (250 mg, 0.668 mmol) produced in Reference Example 28 and, instead of butyl chloroformate, 2-chloroethyl chloroformate (103 μL, 1.00 mmol) to obtain the title compound as white powder (229 mg, yield: 71%).

$^1$H-NMR (400 MHz, DMSO-$d_6$) δ ppm: 8.54 (1H, s), 8.54 (1H, d, J=9 Hz), 7.73-7.72 (2H, m), 6.24 (1H, s), 5.33-5.27 (1H, m), 4.27 (2H, t, J=5 Hz), 4.09 (2H, t, J=9 Hz), 3.82 (2H, dd, J=6 Hz, 5 Hz), 3.80-3.74 (2H, m), 3.31-3.24 (4H, m), 3.15 (3H, s), 2.03-1.95 (2H, m), 1.66-1.57 (2H, m);

MS (ESI) m/z: 481 [M+H]$^+$.

Example 48

1-(6-{[1-(cyclopropylacetyl)piperidin-4-yl]oxy}pyrimidin-4-yl)-5-(methylsulfonyl)indoline (exemplary compound No: 78)

4-(4,4-dimethoxy-1,3,5-triazin-2-yl)-4-methylmorpholinium chloride (72 mg, 0.262 mmol) was added at room temperature to a DMF (4.20 mL) solution of the 5-(methylsulfonyl)-1-[6-(piperidin-4-yloxy)pyrimidin-4-yl]indoline (70.0 mg, 0.187 mmol) produced in Reference Example 28 and cyclopropylacetic acid (28.0 mg, 0.280 mmol), and the mixture was stirred at room temperature for 6 hours. To the reaction solution, water was added, followed by extraction with ethyl acetate three times. The obtained organic layer was washed with water and dried over anhydrous sodium sulfate, and the solvent was distilled off under reduced pressure. The obtained residue was purified by silica gel column chromatography [(i) hexane:ethyl acetate=9:1, V/V; (ii) ethyl acetate] to obtain the title compound as white foam (71.0 mg, yield: 84%).

$^1$H-NMR (500 MHz, DMSO-$d_6$) δ ppm: 8.55 (1H, s), 8.54 (1H, d, J=9 Hz), 7.74-7.72 (2H, m), 6.24 (1H, s), 5.34-5.29 (1H, m), 4.09 (2H, t, J=9 Hz), 3.98-3.94 (1H, m), 3.75-3.70 (1H, m), 3.36-3.26 (3H, m), 3.22-3.17 (1H, m), 3.15 (3H, s), 2.28 (2H, d, J=7 Hz), 2.04-1.95 (2H, m), 1.67-1.51 (2H, m), 1.00-0.92 (1H, m), 0.47-0.43 (2H, m), 0.13-0.11 (2H, m);

MS (FAB) m/z: 457 [M+H]$^+$.

Example 49 cyclopentyl 4-({6-[5-(methylsulfonyl)indolin-1-yl]pyrimidin-4-yl}oxy)piperidine-1-carboxylate (exemplary compound No: 11)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (162 mg, 0.346 mmol) produced in Reference Example 29 and, instead of 2-butanol, cyclopentanol (94 μL, 1.04 mmol) to obtain the title compound as white powder (104 mg, yield: 62%).

$^1$H-NMR (500 MHz, DMSO-$d_6$) δ ppm: 8.54 (1H, s), 8.54 (1H, d, J=9 Hz), 7.74-7.72 (2H, m), 6.23 (1H, s), 5.30-5.25 (1H, m), 5.01-4.98 (1H, m), 4.09 (2H, t, J=9 Hz), 3.75-3.70 (2H, m), 3.28 (2H, t, J=9 Hz), 3.24-3.18 (2H, m), 3.15 (3H, s), 1.99-1.95 (2H, m), 1.82-1.77 (2H, m), 1.67-1.53 (8H, m);

MS (ESI) m/z: 487 [M+H]$^+$.

Example 50

1-(6-{[1-(cyclopropylcarbonyl)piperidin-4-yl]oxy}pyrimidin-4-yl)-5-(methylsulfonyl)indoline (exemplary compound No: 67)

The same reaction as in the method described in Example 48 was performed using the 5-(methylsulfonyl)-1-[6-(piperidin-4-yloxy)pyrimidin-4-yl]indoline (100 mg, 0.267 mmol) produced in Reference Example 28 and, instead of cyclopropylacetic acid, cyclopropanecarboxylic acid (32 μL, 0.40 mmol) to obtain the title compound as white powder (61.0 mg, yield: 52%).

$^1$H-NMR (500 MHz, DMSO-$d_6$) δ ppm: 8.55 (1H, s), 8.55 (1H, d, J=9 Hz), 7.74-7.72 (2H, m), 6.24 (1H, s), 5.36-5.31 (1H, m), 4.09 (2H, t, J=9 Hz), 4.06-3.95 (2H, m), 3.52 (1H, brs), 3.28 (2H, t, J=9 Hz), 3.21 (1H, brs), 3.15 (3H, s), 2.09-1.96 (3H, m), 1.66 (1H, brs), 1.54 (1H, brs), 0.73-0.69 (4H, m);

MS (ESI) m/z: 443 [M+H]$^+$.

Example 51

1-(6-{[1-(isobutylsulfonyl)piperidin-4-yl]oxy}pyrimidin-4-yl)-5-(methylsulfonyl)indoline (exemplary compound No: 127)

The same reaction as in the method described in Example 42 was performed using the 5-(methylsulfonyl)-1-[6-(piperidin-4-yloxy)pyrimidin-4-yl]indoline (100 mg, 0.267 mmol) produced in Reference Example 28 and, instead of 1-butanesulfonyl chloride, isobutanesulfonyl chloride (54 μL, 0.40 mmol) to obtain the title compound as white powder (117 mg, yield: 89%).

$^1$H-NMR (500 MHz, DMSO-$d_6$) δ ppm: 8.55 (1H, s), 8.55 (1H, d, J=9 Hz), 7.74-7.72 (2H, m), 6.25 (1H, s), 5.28-5.23 (1H, m), 4.09 (2H, t, J=9 Hz), 3.46-3.42 (2H, m), 3.28 (2H, t, J=9 Hz), 3.18-3.14 (2H, m), 3.15 (3H, s), 2.93 (2H, d, J=7 Hz), 2.17-2.03 (3H, m), 1.78-1.72 (2H, m), 1.05 (6H, d, J=7 Hz);

MS (ESI) m/z: 495 [M+H]$^+$.

Example 52 cyclobutyl 4-({6-[5-(methylsulfonyl)indolin-1-yl]pyrimidin-4-yl}oxy)piperidine-1-carboxylate (exemplary compound No: 9)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (170 mg, 0.363 mmol) produced in Reference Example 29 and, instead of 2-butanol, cyclobutanol (86 μL, 1.1 mmol) to obtain the title compound as white powder (109 mg, yield: 64%).

$^1$H-NMR (500 MHz, DMSO-$d_6$) δ ppm: 8.55 (1H, s), 8.55 (1H, d, J=9 Hz), 7.74 (1H, s), 7.73 (1H, d, J=6 Hz), 6.24 (1H, s), 5.30-5.25 (1H, m), 4.86-4.80 (1H, m), 4.09 (2H, t, J=9 Hz), 3.76-3.73 (2H, m), 3.28 (2H, t, J=9 Hz), 3.23 (2H, brs), 3.15 (3H, s), 2.27-2.22 (2H, m), 2.03-1.95 (4H, m), 1.71 (1H, q, J=10 Hz), 1.63-1.51 (3H, m);

MS (FAB) m/z: 473 [M+H]$^+$.

Example 53

1-ethylpropyl 4-({6-[5-(methylsulfonyl)indolin-1-yl]pyrimidin-4-yl}oxy)piperidine-1-carboxylate (exemplary compound No: 13)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (176 mg, 0.376 mmol) produced in Reference Example 29 and, instead of 2-butanol, 3-pentanol (122 μL, 1.13 mmol) to obtain the title compound as white foam (93.0 mg, yield: 51%).

$^1$H-NMR (500 MHz, DMSO-$d_6$) δ ppm: 8.54 (1H, s), 8.54 (1H, d, J=9 Hz), 7.74 (1H, s), 7.73 (1H, d, J=5 Hz), 6.24 (1H, s), 5.32-5.27 (1H, m), 4.56-4.51 (1H, m), 4.09 (2H, t, J=9 Hz), 3.79-3.76 (2H, m), 3.28 (2H, t, J=9 Hz), 3.24 (2H, brs), 3.15

(3H, s), 2.01-1.97 (2H, m), 1.61-1.46 (6H, m), 0.85 (3H, d, J=7 Hz), 0.84 (3H, d, J=7 Hz);
MS (FAB) m/z: 489 [M+H]+.

Example 54

1-(6-{[1-(ethylsulfonyl)piperidin-4-yl]oxy}pyrimidin-4-yl)-5-(methylsulfonyl)indoline (exemplary compound No: 122)

The same reaction as in the method described in Example 42 was performed using the 5-(methylsulfonyl)-1-[6-(piperidin-4-yloxy)pyrimidin-4-yl]indoline (100 mg, 0.267 mmol) produced in Reference Example 28 and, instead of 1-butanesulfonyl chloride, ethanesulfonyl chloride (38 µL, 0.40 mmol) to obtain the title compound as white powder (102 mg, yield: 82%).
$^1$H-NMR (500 MHz, DMSO-$d_6$) δ ppm: 8.55 (1H, s), 8.55 (1H, d, J=9 Hz), 7.74 (1H, s), 7.73 (1H, d, J=7 Hz), 6.26 (1H, s), 5.28-5.24 (1H, m), 4.09 (2H, t, J=8 Hz), 3.49-3.45 (2H, m), 3.28 (2H, t, J=9 Hz), 3.21-3.16 (2H, m), 3.15 (3H, s), 3.09 (2H, q, J=7 Hz), 2.08-2.03 (2H, m), 1.77-1.70 (2H, m), 1.23 (3H, t, J=6 Hz);
MS (FAB m/z: 467 [M+H]+.

Example 55 cyclobutylmethyl 4-({6-[5-(methylsulfonyl)indolin-1-yl]pyrimidin-4-yl}oxy)piperidine-1-carboxylate (exemplary compound No: 20)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (176 mg, 0.376 mmol) produced in Reference Example 29 and, instead of 2-butanol, cyclobutylmethanol (107 µL, 1.13 mmol) to obtain the title compound as white powder (136 mg, yield: 74%).
$^1$H-NMR (400 MHz, DMSO-$d_6$) δ ppm: 8.54 (1H, s), 8.54 (1H, d, J=9 Hz), 7.74-7.71 (2H, m), 6.24 (1H, s), 5.31-5.25 (1H, m), 4.09 (2H, t, J=9 Hz), 3.98 (2H, d, J=7 Hz), 3.76 (2H, dt, J=14 Hz, 5 Hz), 3.28 (2H, t, J=9 Hz), 3.24 (2H, brs), 3.15 (3H, s), 2.62-2.50 (1H, m), 2.03-1.96 (4H, m), 1.92-1.69 (4H, m), 1.63-1.54 (2H, m);
MS (FAB) m/z: 487 [M+H]+.

Example 56 tert-butyl 4-[(6-{5-[(cyclopropylmethyl)sulfonyl]-indolin-1-yl}pyrimidin-4-yl)oxy)piperidine-1-carboxylate (exemplary compound No: 537)

Palladium acetate (5.0 mg, 0.020 mmol) was added to a 1,4-dioxane (10.0 mL) suspension of the 5-[(cyclopropylmethyl)sulfonyl]indoline (55.0 mg, 0.201 mmol) produced in Reference Example 16, the tert-butyl 4-[(6-chloropyrimidin-4-yl)oxy]piperidine-1-carboxylate (76.0 mg, 0.241 mmol) produced in Reference Example 41, potassium carbonate (555 mg, 4.02 mmol), and 2-dicyclohexylphosphino-2'-(N,N-dimethylamino)biphenyl (16.0 mg, 0.040 mmol), and the mixture was heated to reflux for 1 hour in a nitrogen atmosphere. The reaction solution was filtered. To the filtrate, an aqueous ammonium chloride solution was added, followed by extraction with acetic acid three times. The organic layer was dried over anhydrous sodium sulfate, and the solvent was distilled off under reduced pressure. The obtained residue was purified by silica gel column chromatography (hexane:ethyl acetate=9:1-3:2, V/V) to obtain the title compound as white powder (102 mg, yield: 99%).
$^1$H-NMR (500 MHz, DMSO-$d_6$) δ ppm: 8.55 (1H, d, J=9 Hz), 8.54 (1H, s), 7.70 (1H, d, J=8 Hz), 7.69 (1H, s), 6.23 (1H, s), 5.29-5.24 (1H, m), 4.09 (2H, t, J=9 Hz), 3.75-3.70 (2H, m), 3.28 (2H, t, J=9 Hz), 3.17 (2H, d, J=7 Hz), 3.17 (2H, brs), 2.00-1.95 (2H, m), 1.60-1.53 (2H, m), 1.41 (9H, s), 0.87-0.80 (1H, m), 0.47-0.43 (2H, m), 0.13-0.10 (2H, m);
MS (FAB) m/z: 515 [M+H]+.

Example 57 tert-butyl 4-({6-[5-(cyclobutylsulfonyl)indolin-1-yl]pyrimidin-4-yl}oxy)piperidine-1-carboxylate (exemplary compound No: 503)

The same reaction as in the method described in Example 56 was performed using the 5-(cyclobutylsulfonyl)indoline (55.0 mg, 0.208 mmol) produced in Reference Example 17 to obtain the title compound as white powder (73.0 mg, yield: 71%).
$^1$H-NMR (500 MHz, DMSO-$d_6$) δ ppm: 8.55 (1H, d, J=9 Hz), 8.54 (1H, s), 7.66 (1H, d, J=9 Hz), 7.65 (1H, s), 6.23 (1H, s), 5.29-5.24 (1H, m), 4.09 (2H, t, J=9 Hz), 4.04-3.97 (1H, m), 3.75-3.70 (2H, m), 3.28 (2H, t, J=9 Hz), 3.17 (2H, brs), 2.35-2.27 (2H, m), 2.15-2.08 (2H, m), 2.00-1.81 (4H, m), 1.60-1.53 (2H, m), 1.41 (9H, s);
MS (FAB) m/z: 515 [M+H]+.

Example 58 tert-butyl 4-({6-[6-methoxy-5-(methylsulfonyl)indolin-1-yl]pyrimidin-4-yl}oxy)piperidine-1-carboxylate (exemplary compound No: 251)

The same reaction as in the method described in Example 1 was performed using the 1-(6-chloropyrimidin-4-yl)-6-methoxy-5-(methylsulfonyl)indoline (200 mg, 0.589 mmol) produced in Reference Example 25 to obtain the title compound as white powder (184 mg, yield: 62%).
$^1$H-NMR (400 MHz, DMSO-$d_6$) δ ppm: 8.55 (1H, s), 8.38 (1H, s), 7.58 (1H, s), 6.23 (1H, s), 5.30-5.24 (1H, m), 4.07 (2H, t, J=9 Hz), 3.95 (3H, s), 3.72 (2H, dt, J=14 Hz, 5 Hz), 3.22-3.12 (4H, m), 3.17 (3H, s), 2.00-1.94 (2H, m), 1.61-1.52 (2H, m), 1.41 (9H, s);
MS (FAB) m/z: 505 [M+H]+.

Example 59 isopropyl 4-({6-[6-methoxy-5-(methylsulfonyl)indolin-1-yl]pyrimidin-4-yl}oxy)piperidine-1-carboxylate (exemplary compound No: 249)

The same reaction as in the method described in Reference Example 28 was performed using the tert-butyl 4-({6-[6-methoxy-5-(methylsulfonyl)indolin-1-yl]pyrimidin-4-yl}oxy)piperidine-1-carboxylate (153 mg, 0.303 mmol) produced in Example 58 to obtain a white powdery compound. The same reaction as in the method described in Example 31 was performed using the obtained compound to obtain the title compound as white powder (120 mg, yield: 82%).
$^1$H-NMR (500 MHz, DMSO-$d_6$) δ ppm: 8.55 (1H, s), 8.38 (1H, s), 7.58 (1H, s), 6.23 (1H, s), 5.31-5.26 (1H, m), 4.78 (1H, sept, J=6 Hz), 4.07 (2H, t, J=9 Hz), 3.95 (3H, s), 3.74

(2H, dt, J=14 Hz, 5 Hz), 3.26-3.16 (4H, m), 3.17 (3H, s), 2.01-1.94 (2H, m), 1.61-1.54 (2H, m), 1.19 (6H, d, J=6 Hz);

MS (FAB) m/z: 491 [M+H]⁺.

Example 60

2,2-difluoroethyl 4-({6-[5-(ethylsulfonyl)indolin-1-yl]pyrimidin-4-yl}oxy)piperidine-1-carboxylate (exemplary compound No: 325)

The same reaction as in the method described in Example 12 was performed using the 5-(ethylsulfonyl)-1-(6-{[1-(1H-imidazol-1-ylcarbonyl)piperidin-4-yl]oxy}pyrimidin-4-yl)indoline (300 mg, 0.622 mmol) produced in Reference Example 31 to obtain the title compound as white powder (233 mg, yield: 76%).

$^1$H-NMR (500 MHz, DMSO-$d_6$) δ ppm: 8.56 (1H, d, J=9 Hz), 8.55 (1H, s), 7.69 (1H, d, J=6 Hz), 7.68 (1H, s), 6.25 (1H, tt, J=55 Hz, 3 Hz), 6.24 (1H, s), 5.33-5.28 (1H, m), 4.31 (2H, td, J=16 Hz, 3 Hz), 4.09 (2H, t, J=9 Hz), 3.76 (2H, dt, J=14 Hz, 5 Hz), 3.34-3.27 (4H, m), 3.21 (2H, q, J=7 Hz), 2.03-1.99 (2H, m), 1.66-1.59 (2H, m), 1.10 (3H, t, J=7 Hz);

MS (ESI) m/z: 497 [M+H]⁺.

Example 61

2,2,2-trifluoroethyl 4-({6-[5-(ethylsulfonyl)indolin-1-yl]pyrimidin-4-yl}oxy)piperidine-1-carboxylate (exemplary compound No: 326)

The same reaction as in the method described in Example 9 was performed using the 5-(ethylsulfonyl)-1-(6-{[1-(1H-imidazol-1-ylcarbonyl)piperidin-4-yl]oxy}pyrimidin-4-yl)indoline (300 mg, 0.622 mmol) produced in Reference Example 31 and, instead of 2-butanol, 2,2,2-trifluoroethanol (187 mg, 1.87 mmol) to obtain the title compound as white powder (233 mg, yield: 58%).

$^1$H-NMR (500 MHz, DMSO-$d_6$) δ ppm: 8.56 (1H, d, J=9 Hz), 8.55 (1H, s), 7.69 (1H, d, J=7 Hz), 7.68 (1H, s), 6.25 (1H, s), 5.34-5.29 (1H, m), 4.72 (2H, q, J=9 Hz), 4.09 (2H, t, J=9 Hz), 3.76 (2H, dt, J=14 Hz, 5 Hz), 3.34-3.27 (4H, m), 3.21 (2H, q, J=7 Hz), 2.04-1.99 (2H, m), 1.67-1.60 (2H, m), 1.10 (3H, t, J=7 Hz);

MS (ESI) m/z: 515 [M+H]⁺.

Example 62

3-furylmethyl 4-({6-[5-(ethylsulfonyl)indolin-1-yl]pyrimidin-4-yl}oxy)piperidine-1-carboxylate (exemplary compound No: 315)

The same reaction as in the method described in Example 19 was performed using the 5-(ethylsulfonyl)-1-(6-{[1-(1H-imidazol-1-ylcarbonyl)piperidin-4-yl]oxy}pyrimidin-4-yl)indoline (200 mg, 0.414 mmol) produced in Reference Example 31 to obtain the title compound as white foam (107 mg, yield: 50%).

$^1$H-NMR (500 MHz, DMSO-$d_6$) δ ppm: 8.56 (1H, d, J=9 Hz), 8.54 (1H, s), 7.73 (1H, s), 7.69 (1H, d, J=7 Hz), 7.68 (1H, s), 7.65 (1H, s), 6.53 (1H, s), 6.23 (1H, s), 5.30-5.25 (1H, m), 4.94 (2H, s), 4.09 (2H, t, J=9 Hz), 3.77-3.74 (2H, m), 3.30-3.19 (6H, m), 1.99-1.97 (2H, m), 1.62-1.56 (2H, m), 1.10 (3H, t, J=7 Hz);

MS (ESI) m/z: 513 [M+H]⁺.

Example 63

5-(ethylsulfonyl)-1-(6-{[1-(3-methylbutanoyl)piperidin-4-yl]oxy}pyrimidin-4-yl)indoline (exemplary compound No: 328)

The same reaction as in the method described in Example 6 was performed using the 5-(ethylsulfonyl)-1-[6-(piperidin-4-yloxy)pyrimidin-4-yl]indoline (200 mg, 0.515 mmol) produced in Reference Example 30 and, instead of butyl chloroformate, isovaleric acid chloride (69 μL, 0.57 mmol) to obtain the title compound as white powder (195 mg, yield: 80%).

$^1$H-NMR (500 MHz, DMSO-$d_6$) δ ppm: 8.56 (1H, d, J=9 Hz), 8.55 (1H, s), 7.69 (1H, d, J=7 Hz), 7.68 (1H, s), 6.24 (1H, s), 5.34-5.29 (1H, m), 4.09 (2H, t, J=9 Hz), 4.00-3.95 (1H, m), 3.79-3.74 (1H, m), 3.37-3.16 (6H, m), 2.22 (2H, d, J=7 Hz), 2.04-1.95 (3H, m), 1.65-1.49 (2H, m), 1.10 (3H, t, J=7 Hz), 0.91 (6H, d, J=7 Hz);

MS (ESI) m/z: 473 [M+H]⁺.

Example 64

2,2,2-trifluoroethyl 4-({6-[5-(propylsulfonyl)indolin-1-yl]pyrimidin-4-yl}oxy)piperidine-1-carboxylate (exemplary compound No: 396)

The same reaction as in the method described in Example 61 was performed using the 1-(6-{[1-(1H-imidazol-1-ylcarbonyl)piperidin-4-yl]oxy}pyrimidin-4-yl)-5-(propylsulfonyl)indoline (140 mg, 0.282 mmol) produced in Reference Example 33 to obtain the title compound as white powder (89.0 mg, yield: 60%).

$^1$H-NMR (500 MHz, DMSO-$d_6$) δ ppm: 8.55 (1H, d, J=9 Hz), 8.55 (1H, s), 7.69 (1H, d, J=7 Hz), 7.68 (1H, s), 6.24 (1H, s), 5.33-5.29 (1H, m), 4.72 (2H, q, J=9 Hz), 4.09 (2H, t, J=9 Hz), 3.76 (2H, dt, J=14 Hz, 5 Hz), 3.36-3.26 (4H, m), 3.19 (2H, t, J=8 Hz), 2.04-2.00 (2H, m), 1.67-1.60 (2H, m), 1.59-1.51 (2H, m), 0.91 (3H, t, J=7 Hz);

MS (ESI) m/z: 529 [M+H]⁺.

Example 65

1-(6-{[1-(3-methylbutanoyl)piperidin-4-yl]oxy}pyrimidin-4-yl)-5-(propylsulfonyl)indoline (exemplary compound No: 397)

The same reaction as in the method described in Example 63 was performed using the 1-[6-(piperidin-4-yloxy)pyrimidin-4-yl]-5-(propylsulfonyl)indoline hydrochloride (200 mg, 0.456 mmol) produced in Reference Example 32 to obtain the title compound as white powder (107 mg, yield: 48%).

$^1$H-NMR (500 MHz, DMSO-$d_6$) δ ppm: 8.55 (1H, d, J=9 Hz), 8.55 (1H, s), 7.69 (1H, d, J=7 Hz), 7.68 (1H, s), 6.24 (1H, s), 5.34-5.29 (1H, m), 4.09 (2H, t, J=9 Hz), 4.00-3.95 (1H, m), 3.79-3.74 (1H, m), 3.37-3.26 (3H, m), 3.21-3.16 (3H, m), 2.22 (2H, d, J=7 Hz), 2.04-1.95 (3H, m), 1.65-1.49 (4H, m), 0.91 (3H, t, J=6 Hz), 0.90 (6H, d, J=6 Hz);

MS (ESI) m/z: 487 [M+H]⁺.

Example 66

2,2,2-trifluoroethyl 4-({6-[5-(isopropylsulfonyl)indolin-1-yl]pyrimidin-4-yl}oxy)piperidine-1-carboxylate (exemplary compound No: 419)

The same reaction as in the method described in Example 61 was performed using the 1-(6-{([1-(1H-imidazol-1-ylcarbonyl)piperidin-4-yl]oxy}pyrimidin-4-yl)-5-(propylsulfonyl)indoline (140 mg, 0.282 mmol) produced in Reference Example 35 to obtain the title compound as white powder (136 mg, yield: 91%).

$^1$H-NMR (500 MHz, DMSO-$d_6$) δ ppm: 8.56 (1H, d, J=9 Hz), 8.55 (1H, s), 7.65 (1H, d, J=7 Hz), 7.64 (1H, s), 6.25 (1H, s), 5.33-5.29 (1H, m), 4.72 (2H, q, J=9 Hz), 4.09 (2H, t, J=9 Hz), 3.76 (2H, dt, J=14 Hz, 5 Hz), 3.37-3.27 (5H, m), 2.05-2.00 (2H, m), 1.67-1.60 (2H, m), 1.16 (6H, d, J=6 Hz);

MS (ESI) m/z: 529 [M+H]$^+$.

Example 67

1-(6-{[1-(3,3-dimethylbutanoyl)piperidin-4-yl]oxy}pyrimidin-4-yl)-5-(methylsulfonyl)indoline (exemplary compound No: 73)

The same reaction as in the method described in Example 3 was performed using the 5-(methylsulfonyl)-1-[6-(piperidin-4-yloxy)pyrimidin-4-yl]indoline hydrochloride (150 mg, 0.365 mmol) produced in Reference Example 27 and, instead of (2-fluoroethyl) chloroformate, tert-butylacetyl chloride (76 μL, 0.55 mmol) to obtain the title compound as white foam (149 mg, yield: 86%).

$^1$H-NMR (500 MHz, DMSO-$d_6$) δ ppm: 8.55 (1H, d, J=9 Hz), 8.55 (1H, s), 7.74 (1H, s), 7.73 (1H, d, J=7 Hz), 6.24 (1H, s), 5.34-5.29 (1H, m), 4.09 (2H, t, J=9 Hz), 4.02-3.97 (1H, m), 3.85-3.80 (1H, m), 3.41-3.36 (1H, m), 3.29 (2H, t, J=9 Hz), 3.22-3.17 (1H, m), 3.15 (3H, s), 2.26 (2H, s), 2.05-1.94 (2H, m), 1.66-1.50 (2H, m), 1.00 (9H, s);

MS (ESI) m/z: 473 [M+H]$^+$.

Example 68 cyclopropylmethyl 4-({6-[5-(propylsulfonyl)indolin-1-yl]pyrimidin-4-yl}oxy)piperidine-1-carboxylate (exemplary compound No: 392)

The same reaction as in the method described in Example 44 was performed using the 1-(6-{[1-(1H-imidazol-1-ylcarbonyl)piperidin-4-yl]oxy}pyrimidin-4-yl)-5-(propylsulfonyl)indoline (205 mg, 0.413 mmol) produced in Reference Example 33 to obtain the title compound as white foam (145 mg, yield: 70%).

$^1$H-NMR (500 MHz, DMSO-$d_6$) δ ppm: 8.55 (1H, d, J=9 Hz), 8.55 (1H, s), 7.69 (1H, d, J=7 Hz), 7.68 (1H, s), 6.24 (1H, s), 5.31-5.26 (1H, m), 4.09 (2H, t, J=9 Hz), 3.86 (2H, d, J=7 Hz), 3.79-3.75 (2H, m), 3.30-3.18 (6H, m), 2.01-1.98 (2H, m), 1.64-1.51 (4H, m), 1.14-1.06 (1H, m), 0.91 (3H, t, J=7 Hz), 0.52-0.48 (2H, m), 0.28-0.25 (2H, m);

MS (ESI) m/z: 501 [M+H]$^+$.

Example 69 cyclopropylmethyl 4-({6-[5-(isopropylsulfonyl)indolin-1-yl]pyrimidin-4-yl}oxy)piperidine-1-carboxylate (exemplary compound No: 415)

The same reaction as in the method described in Example 44 was performed using the 1-(6-{[1-(1H-imidazol-1-ylcarbonyl)piperidin-4-yl]oxy}pyrimidin-4-yl)-5-(isopropylsulfonyl)indoline (184 mg, 0.371 mmol) produced in Reference Example 35 to obtain the title compound as white foam (72.0 mg, yield: 39%).

$^1$H-NMR (500 MHz, DMSO-$d_6$) δ ppm: 8.56 (1H, d, J=9 Hz), 8.54 (1H, s), 7.65 (1H, d, J=7 Hz), 7.64 (1H, s), 6.24 (1H, s), 5.31-5.26 (1H, m), 4.09 (2H, t, J=9 Hz), 3.85 (2H, d, J=7 Hz), 3.79-3.75 (2H, m), 3.34-3.22 (5H, m), 2.01-1.98 (2H, m), 1.64-1.56 (2H, m), 1.15 (6H, d, J=7 Hz), 1.13-1.06 (1H, m), 0.52-0.48 (2H, m), 0.28-0.25 (2H, m);

MS (ESI) m/z: 501 [M+H]$^+$.

Example 70

2-fluoroethyl 4-({6-[5-(ethylsulfonyl)indolin-1-yl]pyrimidin-4-yl}oxy)piperidine-1-carboxylate (exemplary compound No: 317)

The same reaction as in the method described in Example 6 was performed using the 5-(ethylsulfonyl)-1-[6-(piperidin-4-yloxy)pyrimidin-4-yl]indoline (101 mg, 0.260 mmol) produced in Reference Example 30 and, instead of butyl chloroformate, (2-fluoroethyl) chloroformate (28 μL, 0.29 mmol) to obtain the title compound as white foam (108 mg, yield: 87%).

$^1$H-NMR (500 MHz, DMSO-$d_6$) δ ppm: 8.56 (1H, d, J=9 Hz), 8.55 (1H, s), 7.69 (1H, d, J=7 Hz), 7.68 (1H, s), 6.24 (1H, s), 5.32-5.27 (1H, m), 4.61 (2H, dt, J=48 Hz, 4 Hz), 4.26 (2H, dt, J=30 Hz, 4 Hz), 4.09 (2H, t, J=9 Hz), 3.77 (2H, dt, J=14 Hz, 5 Hz), 3.30-3.19 (6H, m), 2.03-1.97 (2H, m), 1, 65-1.58 (2H, m), 1.10 (3H, t, J=7 Hz);

MS (ESI) m/z: 479 [M+H]$^+$.

Example 71

2-fluoroethyl 4-({6-[5-(propylsulfonyl)indolin-1-yl]pyrimidin-4-yl}oxy)piperidine-1-carboxylate (exemplary compound No: 393)

The same reaction as in the method described in Example 70 was performed using the 1-[6-(piperidin-4-yloxy)pyrimidin-4-yl]-5-(propylsulfonyl)indoline (103 mg, 0.256 mmol) produced in Reference Example 34 to obtain the title compound as white foam (61.0 mg, yield: 48%).

$^1$H-NMR (500 MHz, DMSO-$d_6$) δ ppm: 8.55 (1H, d, J=9 Hz), 8.54 (1H, s), 7.69 (1H, d, J=7 Hz), 7.68 (1H, s), 6.24 (1H, s), 5.32-5.27 (1H, m), 4.61 (2H, dt, J=48 Hz, 4 Hz), 4.26 (2H, dt, J=30 Hz, 4 Hz), 4.09 (2H, t, J=9 Hz), 3.77 (2H, dt, J=14 Hz, 5 Hz), 3.31-3.18 (6H, m), 2.02-1.99 (2H, m), 1, 65-1.51 (4H, m), 0.91 (3H, t, J=7 Hz);

MS (ESI) m/z: 493 [M+H]$^+$.

Example 72

2-fluoroethyl 4-({6-[5-(isobutylsulfonyl)indolin-1-yl]pyrimidin-4-yl}oxy)piperidine-1-carboxylate (exemplary compound No: 483)

The same reaction as in the method described in Example 70 was performed using the 5-(isobutylsulfonyl)-1-[6-(piperidin-4-yloxy)pyrimidin-4-yl]indoline (101 mg, 0.242 mmol) produced in Reference Example 36 to obtain the title compound as white foam (113 mg, yield: 92%).

$^1$H-NMR (500 MHz, DMSO-$d_5$) δ ppm: 8.55 (1H, d, J=9 Hz), 8.55 (1H, s), 7.71 (1H, d, J=6 Hz), 7.70 (1H, s), 6.24 (1H, s), 5.32-5.27 (1H, m), 4.61 (2H, dt, J=48 Hz, 4 Hz), 4.26 (2H, dt, J=30 Hz, 4 Hz), 4.09 (2H, t, J=9 Hz), 3.80-3.75 (2H, m), 3.30-3.26 (4H, m), 3.12 (2H, d, J=6 Hz), 2.03-1.95 (3H, m), 1.65-1.58 (2H, m), 0.97 (6H, d, J=7 Hz);
MS (ESI) m/z: 507 [M+H]⁺.

Example 73 isopropyl 4-({6-[5-(isobutylsulfonyl)indolin-1-yl]pyrimidin-4-yl}oxy)piperidine-1-carboxylate (exemplary compound No: 479)

The same reaction as in the method described in Example 31 was performed using the 5-(isobutylsulfonyl)-1-[6-(piperidin-4-yloxy)pyrimidin-4-yl]indoline (100 mg, 0.240 mmol) produced in Reference Example 36 to obtain the title compound as white foam (119 mg, yield: 99%).
$^1$H-NMR (500 MHz, DMSO-$d_6$) δ ppm: 8.54 (1H, d, J=9 Hz), 8.54 (1H, s), 7.71 (1H, d, J=7 Hz), 7.70 (1H, s), 6.23 (1H, s), 5.30-5.25 (1H, m), 4.78 (1H, sept, J=6 Hz), 4.09 (2H, t, J=9 Hz), 3.74 (2H, dt, J=14 Hz, 5 Hz), 3.30-3.20 (4H, m), 3.12 (2H, d, J=6 Hz), 2.03-1.94 (3H, m), 1.62-1.55 (2H, m), 1.19 (6H, d, J=6 Hz), 0.97 (6H, d, J=6 Hz);
MS (ESI) m/z: 503 [M+H]⁺.

Example 74 isopropyl 4-[(6-{5-[(cyclopropylmethyl)sulfonyl]-indolin-1-yl}pyrimidin-4-yl]oxy)piperidine-1-carboxylate (exemplary compound No: 535)

The same reaction as in the method described in Example 31 was performed using the 5-[(cyclopropylmethyl)sulfonyl]-1-[6-(piperidin-4-yloxy)pyrimidin-4-yl]indoline (150 mg, 0.360 mmol) produced in Reference Example 38 to obtain the title compound as white foam (177 mg, yield: 98%).
$^1$H-NMR (500 MHz, DMSO-$d_6$) δ ppm: 8.55 (1H, d, J=7 Hz), 8.54 (1H, s), 7.70 (1H, d, J=8 Hz), 7.69 (1H, s), 6.23 (1H, s), 5.31-5.26 (1H, m), 4.78 (1H, sept, J=6 Hz), 4.10 (2H, t, J=9 Hz), 3.74 (2H, dt, J=14 Hz, 5 Hz), 3.30-3.26 (2H, m), 3.24-3.20 (2H, m), 3.17 (2H, d, J=7 Hz), 2.01-1.95 (2H, m), 1.62-1.55 (2H, m), 1.19 (6H, d, J=6 Hz), 0.87-0.85 (1H, m), 0.47-0.43 (2H, m), 0.13-0.10 (2H, m);
MS (ESI) m/z: 501 [M+H]⁺.

Example 75

2-fluoroethyl 4-[(6-{5-[(cyclopropylmethyl)sulfonyl]-indolin-1-yl}pyrimidin-4-yl)oxy]piperidine-1-carboxylate (exemplary compound No: 539)

The same reaction as in the method described in Example 70 was performed using the 5-[(cyclopropylmethyl)sulfonyl]-1-[6-(piperidin-4-yloxy)pyrimidin-4-yl]indoline (150 mg, 0.360 mmol) produced in Reference Example 38 to obtain the title compound as white foam (182 mg, yield: 92%).
$^1$H-NMR (500 MHz, DMSO-$d_6$) δ ppm: 8.56 (1H, d, J=6 Hz), 8.55 (1H, s), 7.70 (1H, d, J=8 Hz), 7.69 (1H, s), 6.24 (1H, s), 5.32-5.27 (1H, m), 4.61 (2H, dt, J=48 Hz, 4 Hz), 4.26 (2H, dt, J=30 Hz, 4 Hz), 4.10 (2H, t, J=9 Hz), 3.79-3.75 (2H, m), 3.30-3.26 (4H, m), 3.17 (2H, d, J=7 Hz), 2.03-1.98 (2H, m), 1, 65-1.58 (2H, m), 0.87-0.85 (1H, m), 0.47-0.43 (2H, m), 0.13-0.10 (2H, m);
MS (ESI) m/z: 505 [M+H]⁺.

Example 76

2,2,2-trifluoroethyl 4-[(6-{5-[(cyclopropylmethyl)sulfonyl]-indolin-1-yl}pyrimidin-4-yl]oxy)piperidine-1-carboxylate (exemplary compound No: 542)

The same reaction as in the method described in Example 61 was performed using the 5-[(cyclopropylmethyl)sulfonyl]-1-(6-{[1-(1H-imidazol-1-ylcarbonyl)piperidin-4-yl]oxy}pyrimidin-4-yl)indoline (70.0 mg, 0.696 mmol) produced in Reference Example 39 to obtain the title compound as white foam (99.0 mg, yield: 79%).
$^1$H-NMR (500 MHz, DMSO-$d_6$) δ ppm: 8.55 (1H, d, J=9 Hz), 8.55 (1H, s), 7.70 (1H, d, J=8 Hz), 7.69 (1H, s), 6.24 (1H, s), 5.34-5.29 (1H, m), 4.72 (2H, q, J=9 Hz), 4.10 (2H, t, J=9 Hz), 3.76 (2H, dt, J=14 Hz, 4 Hz), 3.30-3.26 (4H, m), 3.17 (2H, d, J=7 Hz), 2.04-2.00 (2H, m), 1.67-1.60 (2H, m), 0.87-0.85 (1H, m), 0.47-0.43 (2H, m), 0.13-0.10 (2H, m);
MS (ESI) m/z: 541 [M+H]⁺.

Example 77

1-(6-{[1-(methoxyacetyl)piperidin-4-yl]oxy}pyrimidin-4-yl)-5-(methylsulfonyl)indoline (exemplary compound No: 98)

The same reaction as in the method described in Example 6 was performed using the 5-(methylsulfonyl)-1-[6-(piperidin-4-yloxy)pyrimidin-4-yl]indoline (114 mg, 0.304 mmol) produced in Reference Example 28 and, instead of butyl chloroformate, methoxyacetyl chloride (32 μL, 0.34 mmol) to obtain the title compound as white foam (108 mg, yield: 79%).
$^1$H-NMR (500 MHz, DMSO-$d_6$) δ ppm: 8.55 (1H, s), 8.55 (1H, d, J=9 Hz), 7.74 (1H, s), 7.73 (1H, d, J=7 Hz), 6.24 (1H, s), 5.35-5.30 (1H, m), 4.11-4.08 (4H, m), 3.95-3.90 (1H, m), 3.69-3.65 (1H, m), 3.29 (3H, s), 3.29-3.26 (4H, m), 3.15 (3H, s), 2.04-1.96 (2H, m), 1.69-1.52 (2H, m);
MS (ESI) m/z: 469 [M+H]⁺.

Example 78 tert-butyl 4-({6-[5-(cyclopropylsulfonyl)indolin-1-yl]pyrimidin-4-yl}oxy)piperidine-1-carboxylate (exemplary compound No: 437)

The same reaction as in the method described in Example 56 was performed using the 5-(cyclopropylsulfonyl)indoline (30.3 mg, 0.136 mmol) produced in Reference Example 15 to obtain the title compound as white powder (63.2 mg, yield: 93%).
$^1$H-NMR (400 MHz, CDCl$_3$) δ ppm: 8.56 (1H, d, J=9 Hz), 8.50 (1H, s), 7.74 (1H, dd, J=9 Hz, 2 Hz), 7.67 (1H, s), 5.98 (1H, s), 5.31 (1H, m), 4.06 (2H, t, J=8 Hz), 3.80 (2H, m), 3.31 (2H, t, J=8 Hz), 3.28 (2H, m), 2.45 (1H, m), 2.00 (2H, m), 1.73 (2H, m), 1.47 (9H, s), 1.33 (2H, m), 1.00 (2H, m);
MS (ESI) m/z: 501 [M+H]⁺.

Example 79 tert-butyl 4-({6-[5-(cyclopentylsulfonyl)indolin-1-yl]pyrimidin-4-yl}oxy)piperidine-1-carboxylate (exemplary compound No: 526)

The same reaction as in the method described in Example 56 was performed using the 5-(cyclopentylsulfonyl)indoline (102 mg, 0.406 mmol) produced in Reference Example 12 to obtain the title compound as white powder (189 mg, yield: 88%).

$^1$H-NMR (400 MHz, CDCl$_3$) δ ppm: 8.56 (1H, d, J=9 Hz), 8.50 (1H, s), 7.73 (1H, d, J=9 Hz), 7.67 (1H, s), 5.98 (1H, s), 5.31 (1H, m), 4.06 (2H, t, J=9 Hz), 3.80 (2H, m), 3.47 (1H, m), 3.34-3.23 (4H, m), 2.11-1.95 (4H, m), 1.88 (2H, m), 1.81-1.66 (4H, m), 1.60 (2H, m), 1.48 (9H, s);
MS (ESI) m/z: 528 [M+H]$^+$.

Example 80 tert-butyl 4-({6-[5-(methylsulfinyl)indolin-1-yl]pyrimidin-4-yl}oxy)piperidine-1-carboxylate (exemplary compound No: 617)

The same reaction as in the method described in Example 56 was performed using 5-methylsulfinylindoline (116 mg, 0.641 mmol) to obtain the title compound as white powder (146 mg, yield: 50%).

$^1$H-NMR (400 MHz, CDCl$_3$) δ ppm: 8.48 (1H, d, J=9 Hz), 8.43 (1H, s), 7.50 (1H, s), 7.37 (1H, dd, J=9 Hz, 1 Hz), 5.89 (1H, s), 5.26 (1H, m), 3.98 (2H, t, J=9 Hz), 3.75 (2H, m), 3.28-3.18 (4H, m), 2.66 (3H, s), 1.95 (2H, m), 1.68 (2H, m), 1.43 (9H, s);
MS (ESI) m/z: 459 [M+H]$^+$.

Example 81 isopropyl 4-({6-[5-(methylsulfinyl)indolin-1-yl]pyrimidin-4-yl}oxy)piperidine-1-carboxylate (exemplary compound No: 615)

The same reaction as in the method described in Example 56 was performed using 5-methylsulfinylindoline (329 mg, 1.79 mmol) and, instead of tert-butyl 4-hydroxypiperidine-1-carboxylate, the isopropyl 4-[(6-chloropyrimidin-4-yl)oxy]piperidine-1-carboxylate (535 mg, 1.79 mmol) produced in Reference Example 42 to obtain the title compound as white powder (467 mg, yield: 59%).

$^1$H-NMR (400 MHz, CDCl$_3$) δ ppm: 8.42 (1H, d, J=9 Hz), 8.36 (1H, s), 7.42 (1H, s), 7.31 (1H, dd, J=9 Hz, 1 Hz), 5.83 (1H, s), 5.22 (1H, m), 4.83 (1H, m), 3.90 (2H, t, J=9 Hz), 3.73 (2H, m), 3.24 (2H, m), 3.17 (2H, t, J=9 Hz), 2.60 (3H, s), 1.91 (2H, m), 1.64 (2H, m), 1.16 (6H, d, J=6 Hz);
MS (ESI) m/z: 445 [M+H]$^+$.

Example 82 tert-butyl 4-({5-methoxy-6-[5-(methylsulfonyl)indolin-1-yl]pyrimidin-4-yl}oxy)piperidine-1-carboxylate (exemplary compound No: 264)

The same reaction as in the method described in Example 56 was performed using 5-methylsulfonylindoline (199 mg, 1.01 mmol) and, instead of tert-butyl 4-hydroxypiperidine-1-carboxylate, the tert-butyl 4-[(6-chloro-5-methoxypyrimidin-4-yl)oxy]piperidine-1-carboxylate (347 mg, 1.01 mmol) produced in Reference Example 43 to obtain the title compound as grayish white foam (431 mg, yield: 85%).

$^1$H-NMR (400 MHz, CDCl$_3$) δ ppm: 8.23 (1H, s), 7.73-7.70 (3H, m), 5.38 (1H, m), 4.34 (2H, t, J=8 Hz), 3.79 (2H, m), 3.77 (3H, s), 3.36 (2H, m), 3.24 (2H, t, J=9 Hz), 3.03 (3H, s), 2.04 (2H, m), 1.83 (2H, m), 1.48 (9H, s);
MS (ESI) m/z: 505 [M+H]$^+$.

Example 83 isopropyl 4-({5-methoxy-6-[5-(methylsulfonyl)indolin-1-yl]pyrimidin-4-yl}oxy)piperidine-1-carboxylate (exemplary compound No: 262)

The same reaction as in the method described in Example 28 was performed using the tert-butyl 4-({5-methoxy-6-[5-(methylsulfonyl)indolin-1-yl]pyrimidin-4-yl}oxy)piperidine-1-carboxylate (369 mg, 0.731 mmol) produced in Example 82 to obtain the title compound as white foam (209 mg, yield: 58%).

$^1$H-NMR (400 MHz, CDCl$_3$) δ ppm: 8.23 (1H, s), 7.73-7.71 (3H, m), 5.39 (1H, m), 4.94 (1H, m), 4.34 (2H, t, J=8 Hz), 3.83 (2H, m), 3.77 (3H, s), 3.40 (2H, m), 3.24 (2H, t, J=9 Hz), 3.03 (3H, s), 2.05 (2H, m), 1.84 (2H, m), 1.27 (6H, d, J=6 Hz);
MS (ESI) m/z: 491 [M+H]$^+$.

Example 84 tert-butyl 4-[(6-{5-[(2-hydroxyethyl)sulfonyl]indolin-1-yl}pyrimidin-4-yl)oxy]piperidine-1-carboxylate (exemplary compound No: 373)

Palladium hydroxide (100 mg) was added to a methanol (10 mL)/ethyl acetate (10 mL) mixed solution of the tert-butyl 4-{[6-(5-{[2-(benzyloxy)ethyl]sulfonyl}indolin-1-yl)pyrimidin-4-yl]oxy}piperidine-1-carboxylate (486 mg, 0.817 mmol) produced in Reference Example 44, and the mixture was stirred for 19.5 hours in a hydrogen atmosphere. The reaction solution was filtered through Celite (trade name), and the solvent was distilled off under reduced pressure. The obtained residue was purified by silica gel column chromatography (hexane:ethyl acetate=3:2-4:1, V/V) to obtain the title compound as white foam (330 mg, yield: 80%).

$^1$H-NMR (400 MHz, CDCl$_3$) δ ppm: 8.61 (1H, d, J=9 Hz), 8.51 (1H, s), 7.76 (1H, dd, J=9 Hz, 2 Hz), 7.70 (1H, s), 5.99 (1H, s), 5.32 (1H, m), 4.07 (2H, t, J=9 Hz), 3.99 (2H, m), 3.80 (2H, m), 3.36-3.23 (6H, m), 2.85 (1H, t, J=6 Hz), 2.00 (2H, m), 1.73 (2H, m), 1.48 (9H, s);
MS (ESI) m/z: 505 [M+H]$^+$.

Example 85 tert-butyl 4-[(6-{5-[(2-fluoroethyl)sulfonyl]indolin-1-yl}pyrimidin-4-yl)oxy]piperidine-1-carboxylate (exemplary compound No: 355)

(Diethylamino)sulfur trifluoride (DAST, 34 μL, 0.260 mmol) was added at −78° C. to a dichloromethane (5 mL) solution of the tert-butyl 4-[(6-{5-[(2-hydroxyethyl)sulfonyl]indolin-1-yl}pyrimidin-4-yl)oxy]piperidine-1-carboxylate (43.1 mg, 0.0855 mmol) produced in Example 84, and the mixture was stirred at −78° C. for 1 hour and further stirred for 30 minutes with heating to 0° C. To the reaction solution, a saturated aqueous solution of sodium bicarbonate was added, followed by extraction with ethyl acetate three times. The obtained organic layer was dried over anhydrous sodium sulfate, and the solvent was distilled off under reduced pressure. The obtained residue was purified by silica gel column chromatography (hexane:ethyl acetate=4:1-7:3, V/V) to obtain the title compound as white foam (17.0 mg, yield: 39%).

$^1$H-NMR (400 MHz, CDCl$_3$) δ ppm: 8.59 (1H, d, J=8 Hz), 8.51 (1H, d, J=1 Hz), 7.77 (1H, d, J=9 Hz, 2 Hz), 7.70 (1H, s), 5.98 (1H, s), 5.32 (1H, m), 4.81 (2H, dt, J=47 Hz, 5 Hz), 4.07

(2H, t, J=9 Hz), 3.80 (2H, m), 3.50 (2H, dt, J=22 Hz, 5 Hz), 3.35-3.23 (4H, m), 2.00 (2H, m), 1.73 (2H, m), 1.48 (9H, s);
MS (ESI) m/z: 507 [M+H]$^+$.

Example 86 tert-butyl 4-[(6-{5-[(2-chloroethyl)sulfonyl]indolin-1-yl}pyrimidin-4-yl)oxy]piperidine-1-carboxylate (exemplary compound No: 364)

Carbon tetrachloride (58 µL, 0.601 mmol) and triphenylphosphine (52 mg, 0.198 mmol) were added to a dichloromethane (5 mL) solution of the tert-butyl 4-[(6-{5-[(2-hydroxyethyl)sulfonyl]indolin-1-yl}pyrimidin-4-yl)oxy]piperidine-1-carboxylate (49.9 mg, 0.0990 mmol) produced in Example 84, and the mixture was stirred overnight at room temperature. From the reaction solution, the solvent was distilled off under reduced pressure. The obtained residue was purified by silica gel column chromatography (hexane:ethyl acetate=9:1-7:3, V/V) to obtain the title compound as white foam (32.3 mg, yield: 62%).
$^1$H-NMR (400 MHz, CDCl$_3$) δ ppm: 8.60 (1H, d, J=9 Hz), 8.51 (1H, s), 7.74 (1H, dd, J=9 Hz, 2 Hz), 7.67 (1H, s), 5.99 (1H, s), 5.32 (1H, m), 4.08 (2H, t, J=9 Hz), 3.80 (2H, m), 3.74 (2H, t, J=7 Hz), 3.51 (2H, t, J=7 Hz), 3.36-3.23 (4H, m), 2.00 (2H, m), 1.73 (2H, m), 1.48 (9H, s);
MS (ESI) m/z: 524 [M+H]$^+$.

Example 87 tert-butyl 4-({6-[5-(aminosulfonyl)indolin-1-yl]pyrimidin-4-yl}oxy)piperidine-1-carboxylate (exemplary compound No: 562)

A concentrated sulfuric acid (5 mL) solution of the tert-butyl 4-[(6-{5-[(dibenzylamino)sulfonyl]indolin-1-yl}pyrimidin-4-yl)oxy]piperidine-1-carboxylate (269 mg, 0.410 mmol) produced in Reference Example 45 was stirred overnight at room temperature. To the reaction solution, a 2 N aqueous sodium hydroxide solution and di(tert-butyl) dicarbonate (1.1 g, 5.0 mmol) were added at 0° C., and the mixture was stirred at room temperature. After 3 hours, THF (100 mL) and di(tert-butyl) dicarbonate (1.1 g, 5.0 mmol) were added thereto, and the mixture was stirred at room temperature for 30 minutes. The reaction solution was subjected to extraction with ethyl acetate three times. The obtained organic layer was dried over anhydrous sodium sulfate, and the solvent was distilled off under reduced pressure. The obtained residue was purified by silica gel column chromatography (hexane:ethyl acetate=1:1, V/V) to obtain the title compound as white powder (151 mg, yield: 77%).
$^1$H-NMR (400 MHz, CDCl$_3$) δ ppm: 8.53 (1H, d, J=9 Hz), 8.51 (1H, d, J=1 Hz), 7.78 (1H, dd, J=9 Hz, 2 Hz), 7.72 (1H, s), 5.97 (1H, d, J=1 Hz), 5.31 (1H, m), 4.72 (2H, s), 4.05 (2H, t, J=8 Hz), 3.80 (2H, m), 3.33-3.24 (4H, m), 2.00 (2H, m), 1.73 (2H, m), 1.48 (9H, s);
MS (ESI) m/z: 476 [M+H]$^+$.

Example 88 isopropyl 4-[(6-{5-[(dimethylamino)sulfonyl]indolin-1-yl}pyrimidin-4-yl)oxy]piperidine-1-carboxylate (exemplary compound No: 604)

Concentrated hydrochloric acid (235 µL, 2.66 mmol) was added to an acetone (8 mL)/water (2 mL) mixed solution of N,N-dimethylindoline-5-sulfonamide (120 mg, 0.531 mmol) and the isopropyl 4-[(6-chloropyrimidin-4-yl)oxy]piperidine-1-carboxylate (79.6 mg, 0.266 mmol) produced in Reference Example 42, and the mixture was stirred at 80° C. for 15 hours. To the reaction solution, a saturated aqueous solution of sodium bicarbonate was added, followed by extraction with ethyl acetate three times. The obtained organic layer was dried over anhydrous sodium sulfate, and the solvent was distilled off under reduced pressure. The obtained residue was purified by silica gel column chromatography (hexane:ethyl acetate=4:1-1:1, V/V) to obtain the title compound as pale yellow powder (77.2 mg, yield: 59%).
$^1$H-NMR (400 MHz, CDCl$_3$) δ ppm: 8.55 (1H, d, J=9 Hz), 8.50 (1H, s), 7.63 (1H, dd, J=9 Hz, 2 Hz), 7.57 (1H, s), 5.97 (1H, s), 5.33 (1H, m), 4.94 (1H, m), 4.05 (2H, t, J=9 Hz), 3.83 (2H, m), 3.38-3.26 (4H, m), 2.70 (6H, s), 2.01 (2H, m), 1.74 (2H, m), 1.26 (6H, d, J=6 Hz);
MS (ESI) m/z: 490 [M+H]$^+$.

Example 89 isopropyl 4-({6-[5-(aminosulfonyl)indolin-1-yl]pyrimidin-4-yl}oxy)piperidine-1-carboxylate (exemplary compound No: 560)

The same reaction as in the method described in Example 88 was performed using the isopropyl 4-[(6-chloropyrimidin-4-yl)oxy]piperidine-1-carboxylate (239 mg, 0.800 mmol) produced in Reference Example 42 and, instead of N,N-dimethylindoline-5-sulfonamide, indoline-5-sulfonamide (106 mg, 0.533 mmol) to obtain the title compound as white powder (17.0 mg, yield: 7%).
$^1$H-NMR (400 MHz, CDCl$_3$) δ ppm: 8.53 (1H, d, J=9 Hz), 8.50 (1H, s), 7.78 (1H, dd, J=9 Hz, 2 Hz), 7.72 (1H, s), 5.97 (1H, s), 5.33 (1H, m), 4.94 (1H, m), 4.72 (2H, s), 4.05 (2H, t, J=9 Hz), 3.83 (2H, m), 3.33 (2H, m), 3.30 (2H, t, J=9 Hz), 2.01 (2H, m), 1.74 (2H, m), 1.26 (6H, d, J=6 Hz);
MS (ESI) m/z: 462 [M+H]$^+$.

Example 90 isopropyl 4-[(6-{5-[(methylamino)sulfonyl]indolin-1-yl}pyrimidin-4-yl)oxy]piperidine-1-carboxylate (exemplary compound No: 583)

The same reaction as in the method described in Example 88 was performed using the isopropyl 4-[(6-chloropyrimidin-4-yl)oxy]piperidine-1-carboxylate (214 mg, 0.714 mmol) produced in Reference Example 42 and, instead of N,N-dimethylindoline-5-sulfonamide, N-methylindoline-5-sulfonamide (101 mg, 0.476 mmol) to obtain the title compound as white powder (20.0 mg, yield: 9%).
$^1$H-NMR (400 MHz, CDCl$_3$) δ ppm: 8.55 (1H, d, J=8 Hz), 8.51 (1H, s), 7.73 (1H, d, J=8 Hz), 7.64 (1H, s), 5.98 (1H, s), 5.37 (1H, m), 4.94 (1H, m), 4.37 (1H, m), 4.06 (2H, t, J=8 Hz), 3.83 (2H, m), 3.38-3.28 (4H, m), 2.66 (3H, d, J=5 Hz), 2.03 (2H, m), 1.76 (2H, m), 1.24 (6H, d, J=7 Hz);
MS (ESI) m/z: 476 [M+H]$^+$.

Example 91 tert-butyl 4-({2-methyl-6-[5-(methylsulfonyl)indolin-1-yl]pyrimidin-4-yl}oxy)piperidine-1-carboxylate (exemplary compound No: 193)

The same reaction as in the method described in Example 1 was performed using the 1-(6-chloro-2-methylpyrimidin-4-yl)-5-(methylsulfonyl)indoline (67.3 mg, 0.203 mmol)

produced in Reference Example 26 to obtain the title compound as white powder (49.1 mg, yield: 72%).

$^1$H-NMR (400 MHz, CDCl$_3$) δ ppm: 8.60 (1H, d, J=9 Hz), 7.78 (1H, dd, J=9 Hz, 2 Hz), 7.70 (1H, s), 5.79 (1H, s), 5.34 (1H, m), 4.04 (2H, t, J=9 Hz), 3.77 (2H, m), 3.34-3.24 (4H, m), 3.03 (3H, m), 2.56 (3H, s), 1.98 (2H, m), 1.72 (2H, m), 1.48 (9H, s);

MS (ESI) m/z: 489 [M+H]$^+$.

Example 92

1-(6-{[1-(3-methylbutanoyl)piperidin-4-yl]oxy}pyrimidin-4-yl)-5-(methylsulfonyl)indoline (exemplary compound No: 69)

The same reaction as in the method described in Example 63 was performed using the 5-(methylsulfonyl)-1-[6-(piperidin-4-yloxy)pyrimidin-4-yl]indoline (843 mg, 2.25 mmol) produced in Reference Example 28 to obtain the title compound as white powder (961 mg, yield: 93%).

$^1$H-NMR (400 MHz, CDCl$_3$) δ ppm: 8.57 (1H, d, J=9 Hz), 8.50 (1H, s), 7.76 (1H, d, J=9 Hz), 7.70 (1H, s), 5.98 (1H, s), 5.38 (1H, m), 4.06 (2H, t, J=9 Hz), 4.04 (1H, m), 3.76 (1H, m), 3.43 (2H, m), 3.30 (2H, t, J=9 Hz), 3.04 (3H, s), 2.25 (2H, d, J=7 Hz), 2.13 (1H, m), 2.05 (2H, m), 1.76 (2H, m), 0.99 (6H, d, J=7 Hz);

MS (ESI) m/z: 459 [M+H]$^+$.

Example 93

4-fluorophenyl 4-({6-[5-(methylsulfonyl)indolin-1-yl]pyrimidin-4-yl}oxy)piperidine-1-carboxylate (exemplary compound No: 47)

The same reaction as in the method described in Example 6 was performed using the 5-(methylsulfonyl)-1-[6-(piperidin-4-yloxy)pyrimidin-4-yl]indoline (133 mg, 0.356 mmol) produced in Reference Example 28 and, instead of butyl chloroformate, 4-fluorophenyl chloroformate (55 μL, 0.430 mmol) to obtain the title compound as white powder (150 mg, yield: 82%).

$^1$H-NMR (400 MHz, CDCl$_3$) δ ppm: 8.59 (1H, d, J=9 Hz), 8.52 (1H, s), 7.79 (1H, d, J=9 Hz), 7.73 (1H, s), 7.12-7.01 (4H, m), 6.01 (1H, s), 5.41 (1H, m), 4.08 (2H, t, J=9 Hz), 4.03-3.84 (2H, m), 3.64-3.43 (2H, m), 3.32 (2H, t, J=9 Hz), 3.04 (3H, s), 2.10 (2H, m), 1.88 (2H, m);

MS (ESI) m/z: 513 [M+H]$^+$.

Example 94

4-methoxyphenyl 4-({6-[5-(methylsulfonyl)indolin-1-yl]pyrimidin-4-yl}oxy)piperidine-1-carboxylate (exemplary compound No: 48)

The same reaction as in the method described in Example 6 was performed using the 5-(methylsulfonyl)-1-[6-(piperidin-4-yloxy)pyrimidin-4-yl]indoline (135 mg, 0.361 mmol) produced in Reference Example 28 and, instead of butyl chloroformate, 4-methoxyphenyl chloroformate (65 μL, 0.437 mmol) to obtain the title compound as white powder (166 mg, yield: 88%).

$^1$H-NMR (500 MHz, CDCl$_3$) δ ppm: 8.58 (1H, d, J=9 Hz), 8.52 (1H, s), 7.79 (1H, d, J=9 Hz), 7.73 (1H, s), 7.03 (2H, d, J=9 Hz), 6.88 (2H, d, J=9 Hz), 6.01 (1H, s), 5.41 (1H, m), 4.08 (2H, t, J=9 Hz), 4.03-3.85 (2H, m), 3.80 (3H, s), 3.63-3.43 (2H, m), 3.32 (2H, t, J=9 Hz), 3.04 (3H, s), 2.09 (2H, m), 1.86 (2H, m);

MS (ESI) m/z: 525 [M+H]$^+$.

Example 95

N,N-dimethyl-4-({6-[5-(methylsulfonyl)indolin-1-yl]pyrimidin-4-yl}oxy)piperidine-1-carboxamide (exemplary compound No: 114)

The same reaction as in the method described in Example 6 was performed using the 5-(methylsulfonyl)-1-[6-(piperidin-4-yloxy)pyrimidin-4-yl]indoline (63.3 mg, 0.169 mmol) produced in Reference Example 28 and, instead of butyl chloroformate, dimethylcarbamyl chloride (19 μL, 0.206 mmol) to obtain the title compound as white powder (66.1 mg, yield: 88%).

$^1$H-NMR (400 MHz, CDCl$_3$) δ ppm: 8.58 (1H, d, J=9 Hz), 8.51 (1H, s), 7.78 (1H, dd, J=9 Hz, 2 Hz), 7.72 (1H, m), 5.98 (1H, s), 5.32 (1H, m), 4.06 (2H, t, J=9 Hz), 3.55 (2H, m), 3.31 (2H, t, J=9 Hz), 3.13 (2H, m), 3.04 (3H, s), 2.85 (6H, s), 2.05 (2H, m), 1.79 (2H, m);

MS (ESI) m/z: 446 [M+H]$^+$.

Example 96

5-(methylsulfonyl)-1-(6-{[1-(3-phenylpropanoyl)piperidin-4-yl]oxy}pyrimidin-4-yl)indoline (exemplary compound No: 93)

The same reaction as in the method described in Example 48 was performed using the 5-(methylsulfonyl)-1-[6-(piperidin-4-yloxy)pyrimidin-4-yl]indoline (118 mg, 0.316 mmol) produced in Reference Example 28 and, instead of cyclopropylacetic acid, 3-phenylpropionic acid (90 mg, 0.602 mmol) to obtain the title compound as white powder (150 mg, yield: 94%).

$^1$H-NMR (400 MHz, CDCl$_3$) δ ppm: 8.57 (1H, d, J=9 Hz), 8.49 (1H, s), 7.77 (1H, dd, J=9 Hz, 2 Hz), 7.70 (1H, s), 7.34-7.18 (5H, m), 5.97 (1H, s), 5.34 (1H, m), 4.05 (2H, t, J=9 Hz), 3.98 (1H, m), 3.66 (1H, m), 3.49 (1H, m), 3.33 (1H, m), 3.29 (2H, t, J=9 Hz), 3.04 (3H, s), 2.99 (2H, t, J=8 Hz), 2.67 (2H, t, J=7 Hz), 2.03-1.87 (2H, m), 1.81-1.61 (2H, m);

MS (ESI) m/z: 507 [M+H]$^+$.

Example 97

1-[6-({1-[3-(4-methoxyphenyl)propanoyl]piperidin-4-yl}oxy)pyrimidin-4-yl]-5-(methylsulfonyl)indoline (exemplary compound No: 95)

The same reaction as in the method described in Example 48 was performed using the 5-(methylsulfonyl)-1-[6-(piperidin-4-yloxy)pyrimidin-4-yl]indoline (148 mg, 0.396 mmol) produced in Reference Example 28 and, instead of cyclopropylacetic acid, 3-(4-methoxyphenyl)propionic acid (107 mg, 0.594 mmol) to obtain the title compound as white powder (178 mg, yield: 84%).

$^1$H-NMR (400 MHz, CDCl$_3$) δ ppm: 8.57 (1H, d, J=9 Hz), 8.50 (1H, s), 7.78 (1H, dd, J=9 Hz, 2 Hz), 7.72 (1H, s), 7.15 (2H, d, J=9 Hz), 6.84 (2H, d, J=9 Hz), 5.98 (1H, s), 5.35 (1H, m), 4.06 (2H, t, J=9 Hz), 4.00 (1H, m), 3.79 (3H, s), 3.66 (1H, m), 3.47 (1H, m), 3.38-3.26 (3H, m), 3.04 (3H, s), 2.93 (2H, t, J=8 Hz), 2.63 (2H, t, J=7 Hz), 2.04-1.89 (2H, m), 1.81-1.61 (2H, m);

MS (ESI) m/z: 537 [M+H]$^+$.

Example 98

1-[6-({1-[3-(4-fluorophenyl)propanoyl]piperidin-4-yl}oxy)pyrimidin-4-yl]-5-(methylsulfonyl)indoline (exemplary compound No: 94)

The same reaction as in the method described in Example 48 was performed using the 5-(methylsulfonyl)-1-[6-(piperidin-4-yloxy)pyrimidin-4-yl]indoline (179 mg, 0.479 mmol) produced in Reference Example 28 and, instead of cyclopropylacetic acid, 3-(4-fluorophenyl)propionic acid (121 mg, 0.720 mmol) to obtain the title compound as white powder (183 mg, yield: 73%).

$^1$H-NMR (400 MHz, CDCl$_3$) δ ppm: 8.57 (1H, d, J=9 Hz), 8.49 (1H, s), 7.78 (1H, dd, J=9 Hz, 2 Hz), 7.71 (1H, s), 7.19 (2H, m), 6.98 (2H, m), 5.98 (1H, s), 5.36 (1H, m), 4.06 (2H, t, J=9 Hz), 4.00 (1H, m), 3.66 (1H, m), 3.48 (1H, m), 3.39-3.26 (3H, m), 3.04 (3H, s), 2.96 (2H, t, J=7 Hz), 2.64 (2H, t, J=7 Hz), 2.04-1.85 (2H, m), 1.81-1.62 (2H, m);

MS (ESI) m/z: 525 [M+H]$^+$.

Example 99

1-(6-{[1-(3-cyclopropylpropanoyl)piperidin-4-yl]oxy}pyrimidin-4-yl)-5-(methylsulfonyl)indoline (exemplary compound No: 79)

The same reaction as in the method described in Example 48 was performed using the 5-(methylsulfonyl)-1-[6-(piperidin-4-yloxy)pyrimidin-4-yl]indoline (112 mg, 0.299 mmol) produced in Reference Example 28 and, instead of cyclopropylacetic acid, 3-cyclopropylpropionic acid (209 mg, 1.83 mmol) to obtain the title compound as white powder (62.9 mg, yield: 44%).

$^1$H-NMR (400 MHz, CDCl$_3$) δ ppm: 8.58 (1H, d, J=9 Hz), 8.51 (1H, s), 7.79 (1H, dd, J=9 Hz, 2 Hz), 7.72 (1H, s), 5.99 (1H, s), 5.38 (1H, m), 4.07 (2H, t, J=9 Hz), 4.03 (1H, m), 3.77 (1H, m), 3.50-3.38 (2H, m), 3.31 (2H, t, J=9 Hz), 3.04 (3H, s), 2.48 (2H, t, J=8 Hz), 2.12-1.96 (2H, m), 1.85-1.68 (2H, m), 1.56 (2H, m), 0.74 (1H, m), 0.45 (2H, m), 0.08 (2H, m);

MS (ESI) m/z: 471 [M+H]$^+$.

Example 100

5-(methylsulfonyl)-1-(6-{[1-(4,4,4-trifluorobutanoyl)piperidin-4-yl]oxy}pyrimidin-4-yl)indoline (exemplary compound No: 82)

The same reaction as in the method described in Example 48 was performed using the 5-(methylsulfonyl)-1-[6-(piperidin-4-yloxy)pyrimidin-4-yl]indoline (220 mg, 0.588 mmol) produced in Reference Example 28 and, instead of cyclopropylacetic acid, 4,4,4-trifluorobutanoic acid (107 mg, 0.754 mmol) to obtain the title compound as white powder (135 mg, yield: 46%).

$^1$H-NMR (400 MHz, CDCl$_3$) δ ppm: 8.58 (1H, d, J=9 Hz), 8.51 (1H, s), 7.79 (1H, dd, J=9 Hz, 2 Hz), 7.73 (1H, s), 5.99 (1H, s), 5.40 (1H, m), 4.07 (2H, t, J=9 Hz), 3.98 (1H, m), 3.73 (1H, m), 3.52 (1H, m), 3.43 (1H, m), 3.32 (2H, t, J=9 Hz), 3.04 (3H, s), 2.65-2.46 (4H, m), 2.13-1.97 (2H, m), 1.88-1.73 (2H, m);

MS (ESI) m/z: 499 [M+H]$^+$.

Example 101

N-isopropyl-4-({6-[5-(methylsulfonyl)indolin-1-yl]pyrimidin-4-yl}oxy)piperidine-1-carboxamide (exemplary compound No: 106)

Isopropyl isocyanate (31 μL, 0.315 mmol) was added to a dichloromethane (5 mL) solution of the 5-(methylsulfonyl)-1-[6-(piperidin-4-yloxy)pyrimidin-4-yl]indoline (78.1 mg, 0.209 mmol) produced in Reference Example 28, and the mixture was stirred at room temperature for 30 minutes. To the reaction solution, water was added, followed by extraction with ethyl acetate three times. The obtained organic layer was dried over anhydrous sodium sulfate, and the solvent was distilled off under reduced pressure. The obtained residue was purified by silica gel column chromatography (ethyl acetate) to obtain the title compound as white powder (87.3 mg, yield: 91%).

$^1$H-NMR (400 MHz, CDCl$_3$) δ ppm: 8.57 (1H, d, J=9 Hz), 8.50 (1H, s), 7.78 (1H, dd, J=9 Hz, 2 Hz), 7.71 (1H, s), 5.98 (1H, s), 5.33 (1H, m), 4.31 (1H, d, J=7 Hz), 4.06 (2H, t, J=9 Hz), 3.99 (1H, m), 3.70 (2H, m), 3.31 (2H, t, J=9 Hz), 3.25 (2H, m), 3.04 (3H, s), 2.03 (2H, m), 1.77 (2H, m), 1.17 (6H, d, J=6 Hz);

MS (ESI) m/z: 460 [M+H]$^+$.

Example 102

1-methylcyclopentyl 4-({6-[5-(methylsulfonyl)indolin-1-yl]pyrimidin-4-yl}oxy)piperidine-1-carboxylate (exemplary compound No: 16)

1,1'-carbonyldiimidazole (1.09 g, 6.70 mmol) was added to a toluene (30 mL) solution of 1-methylcyclopentanol (671 mg, 6.70 mmol), and the mixture was stirred at room temperature for 4.5 hours. From the reaction solution, the solvent was distilled off under reduced pressure. The obtained residue was purified by silica gel column chromatography (hexane:ethyl acetate=4:1, V/V) to obtain a colorless oil compound (417 mg). Hereinafter, this compound is referred to as an imidazole compound.

Potassium carbonate (153 mg, 1.11 mmol) and the imidazole compound (129 mg, 0.665 mmol) were added to a dioxane (10 mL) solution of the 5-(methylsulfonyl)-1-[6-(piperidin-4-yloxy)pyrimidin-4-yl]indoline (82.9 mg, 0.222 mmol) produced in Reference Example 28, and the mixture was heated to reflux for 8 hours. To the reaction solution, a saturated aqueous solution of ammonium chloride was added, followed by extraction with ethyl acetate. The obtained organic layer was dried over anhydrous sodium sulfate, and the solvent was distilled off under reduced pressure. The obtained residue was purified by silica gel column chromatography (hexane:ethyl acetate=4:1-3:2, V/V) to obtain the title compound as white powder (46.8 mg, yield: 42%).

$^1$H-NMR (400 MHz, CDCl$_3$) δ ppm: 8.57 (1H, d, J=9 Hz), 8.50 (1H, s), 7.78 (1H, dd, J=9 Hz, 2 Hz), 7.71 (1H, s), 5.98 (1H, s), 5.32 (1H, m), 4.06 (2H, t, J=9 Hz), 3.80 (2H, m), 3.34-3.24 (4H, m), 3.04 (3H, s), 2.14 (2H, m), 2.00 (2H, m), 1.79-1.60 (8H, m), 1.59 (3H, s);

MS (ESI) m/z: 501 [M+H]$^+$.

Example 103

2-fluoro-1-methylethyl 4-({6-[5-(methylsulfonyl)indolin-1-yl]pyrimidin-4-yl}oxy)piperidine-1-carboxylate (exemplary compound No: 56)

The same reaction as in the method described in Example 102 was performed using the 5-(methylsulfonyl)-1-[6-(piperidin-4-yloxy)pyrimidin-4-yl]indoline (47.7 mg, 0.128 mmol) produced in Reference Example 28 and, instead of 1-methylcyclopentanol, 1-fluoro-2-propanol to obtain the title compound as white powder (27.8 mg, yield: 45%).

$^1$H-NMR (400 MHz, CDCl$_3$) δ ppm: 8.58 (1H, d, J=9 Hz), 8.51 (1H, s), 7.79 (1H, dd, J=9 Hz, 2 Hz), 7.72 (1H, s), 5.98 (1H, s), 5.35 (1H, m), 5.06 (1H, m), 4.44 (2H, m), 4.07 (2H, t, J=9 Hz), 3.84 (2H, m), 3.38 (2H, m), 3.31 (2H, d, J=9 Hz), 3.04 (3H, s), 2.02 (2H, m), 1.77 (2H, m), 1.31 (3H, d, J=7 Hz);

MS (ESI) m/z: 479 [M+H]$^+$.

Example 104

2,2,2-trifluoroethyl 4-({6-[5-(methylsulfonyl)indolin-1-yl]pyrimidin-4-yl}oxy)piperidine-1-carboxylate (exemplary compound No: 54)

The same reaction as in the method described in Example 61 was performed using the 1-(6-{[1-(1H-imidazol-1-ylcarbonyl)piperidin-4-yl]oxy}pyrimidin-4-yl)-5-(methylsulfonyl)indoline (300 mg, 0.640 mmol) produced in Reference Example 29 to obtain the title compound as white foam (217 mg, yield: 68%).

$^1$H-NMR (400 MHz, CDCl$_3$) δ ppm: 8.58 (1H, d, J=9 Hz), 8.51 (1H, s), 7.78 (1H, dd, J=9 Hz, 2 Hz), 7.72 (1H, s), 5.99 (1H, s), 5.37 (1H, m), 4.52 (2H, qd, J=9 Hz, 2 Hz), 4.06 (2H, t, J=9 Hz), 3.83 (2H, m), 3.46 (2H, m), 3.31 (2H, t, J=9 Hz), 3.04 (3H, s), 2.03 (2H, m), 1.81 (2H, m);

MS (ESI) m/z: 501 [M+H]$^+$.

Example 105

1,1-dimethylpropyl 4-({6-[5-(methylsulfonyl)indolin-1-yl]pyrimidin-4-yl}oxy)piperidine-1-carboxylate (exemplary compound No: 14)

Trifluoroacetic acid (2 mL) was added to a dichloromethane (10 mL) solution of the tert-butyl 4-({6-[5-(methylsulfonyl)indolin-1-yl]pyrimidin-4-yl}oxy)piperidine-1-carboxylate (430 mg, 0.881 mmol) produced in Example 1, and the mixture was stirred at room temperature for 2 hours. From the reaction solution, the solvent was distilled off under reduced pressure. The same reaction as in the method described in Example 102 was performed using a portion (201 mg) of the obtained residue and, instead of 1-methylcyclopentanol, 2-methyl-2-butanol to obtain the title compound as white powder (50.4 mg, yield: 19%).

$^1$H-NMR (400 MHz, CDCl$_3$) δ ppm: 8.58 (1H, d, J=9 Hz), 8.51 (1H, s), 7.78 (1H, dd, J=9 Hz, 2 Hz), 7.72 (1H, s), 5.98 (1H, s), 5.32 (1H, m), 4.07 (2H, t, J=9 Hz), 3.80 (2H, m), 3.31 (2H, d, J=9 Hz), 3.29 (2H, m), 3.04 (3H, s), 2.00 (2H, m), 1.80 (2H, q, J=7 Hz), 1.73 (2H, m), 1.45 (6H, s), 0.91 (3H, t, J=7 Hz);

MS (ESI) m/z: 489 [M+H]$^+$.

Example 106

1-methylcyclohexyl 4-({6-[5-(methylsulfonyl)indolin-1-yl]pyrimidin-4-yl}oxy)piperidine-1-carboxylate (exemplary compound No: 17)

The same reaction as in the method described in Example 105 was performed using the tert-butyl 4-({6-[5-(methylsulfonyl)indolin-1-yl]pyrimidin-4-yl}oxy)piperidine-1-carboxylate (430 mg, 0.881 mmol) produced in Example 1 and, instead of 2-methyl-2-butanol, 1-methylcyclohexanol to obtain the title compound as white powder (78.5 mg, yield: 34%).

$^1$H-NMR (400 MHz, CDCl$_3$) δ ppm: 8.58 (1H, d, J=9 Hz), 8.51 (1H, s), 7.79 (1H, dd, J=9 Hz, 2 Hz), 7.72 (1H, s), 5.98 (1H, s), 5.33 (1H, m), 4.07 (2H, t, J=9 Hz), 3.84 (2H, m), 3.36-3.26 (4H, m), 3.04 (3H, s), 2.19 (2H, m), 2.02 (2H, m), 1.74 (2H, m), 1.62-1.23 (8H, m), 1.50 (3H, s);

MS (ESI) m/z: 515 [M+H]$^+$.

Example 107

4-methoxybenzyl 4-({6-[5-(methylsulfonyl)indolin-1-yl]pyrimidin-4-yl}oxy)piperidine-1-carboxylate (exemplary compound No: 51)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (180 mg, 1.60 mmol) produced in Reference Example 29 and, instead of 2-butanol, 4-methoxybenzyl alcohol (100 µL, 0.802 mmol) to obtain the title compound as white powder (167 mg, yield: 81%).

$^1$H-NMR (400 MHz, CDCl$_3$) δ ppm: 8.57 (1H, d, J=9 Hz), 8.50 (1H, d, J=1 Hz), 7.78 (1H, dd, J=9 Hz, 2 Hz), 7.71 (1H, s), 7.32 (2H, m), 6.88 (2H, m), 5.97 (1H, s), 5.33 (1H, m), 5.08 (2H, s), 4.06 (2H, t, J=9 Hz), 3.84 (2H, m), 3.81 (3H, s), 3.37 (2H, m), 3.30 (2H, t, J=9 Hz), 3.04 (3H, s), 2.00 (2H, m), 1.75 (2H, m);

MS (ESI) m/z: 539 [M+H]$^+$.

Example 108

4-fluorobenzyl 4-({6-[5-(methylsulfonyl)indolin-1-yl]pyrimidin-4-yl}oxy)piperidine-1-carboxylate (exemplary compound No: 50)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (170 mg, 0.363 mmol) produced in Reference Example 29 and, instead of 2-butanol, 4-fluorobenzyl alcohol (100 µL, 0.917 mmol) to obtain the title compound as white foam (50.4 mg, yield: 26%).

$^1$H-NMR (400 MHz, CDCl$_3$) δ ppm: 8.57 (1H, d, J=9 Hz), 8.50 (1H, d, J=1 Hz), 7.79 (1H, dd, J=9 Hz, 2 Hz), 7.72 (1H, m), 7.36 (2H, m), 7.05 (2H, m), 5.99 (1H, d, J=1 Hz), 5.34 (1H, m), 5.11 (2H, s), 4.06 (2H, t, J=9 Hz), 3.84 (2H, m), 3.39 (2H, m), 3.31 (2H, t, J=9 Hz), 3.04 (3H, s), 2.02 (2H, m), 1.76 (2H, m);

MS (ESI) m/z: 527 [M+H]$^+$.

Example 109

(2,2-difluorocyclopropyl)methyl 4-({6-[5-(methylsulfonyl)indolin-1-yl]pyrimidin-4-yl}oxy)piperidine-1-carboxylate (exemplary compound No: 57)

The same reaction as in the method described in Example 9 was performed using the 1-(6-{[1-(1H-imidazol-1-ylcarbonyl)piperidin-4-yl]oxy}pyrimidin-4-yl)-5-(methylsulfonyl)indoline (240 mg, 0.513 mmol) produced in Reference Example 29 and, instead of 2-butanol, 2,2-difluorocyclopropylmethanol (199 mg, 1.84 mmol) to obtain the title compound as white powder (194 mg, yield: 74%).

$^1$H-NMR (400 MHz, CDCl$_3$) δ ppm: 8.58 (1H, d, J=9 Hz), 8.51 (1H, d, J=1 Hz), 7.78 (1H, dd, J=9 Hz, 2 Hz), 7.72 (1H, m), 5.99 (1H, d, J=1 Hz), 5.35 (1H, m), 4.28 (1H, m), 4.10-4.02 (3H, m), 3.83 (2H, m), 3.39 (2H, m), 3.31 (2H, t, J=9 Hz), 3.04 (3H, s), 2.08-1.95 (3H, m), 1.77 (2H, m), 1.52 (1H, m), 1.23 (1H, m);

MS (ESI) m/z: 509 [M+H]$^+$.

Example 110 cyclopropylmethyl 4-({6-[5-(ethylsulfonyl)indolin-1-yl]pyrimidin-4-yl}oxy)piperidine-1-carboxylate (exemplary compound No: 313)

The same procedure as in the method described in Example 44 was performed using the 5-(ethylsulfonyl)-1-(6-{[1-(1H-imidazol-1-ylcarbonyl)piperidin-4-yl]oxy}pyrimidin-4-yl)indoline (97.9 mg, 0.203 mmol) produced in Reference Example 31 to obtain the title compound as white powder (44.1 mg, yield: 45%).

$^1$H-NMR (400 MHz, CDCl$_3$) δ ppm: 8.58 (1H, d, J=9 Hz), 8.51 (1H, s), 7.74 (1H, dd, J=9 Hz, 2 Hz), 7.68 (1H, s), 5.99 (1H, s), 5.34 (1H, m), 4.07 (2H, t, J=9 Hz), 3.93 (2H, d, J=7 Hz), 3.86 (2H, m), 3.37 (2H, m), 3.31 (2H, t, J=9 Hz), 3.10 (2H, q, J=7 Hz), 2.03 (2H, m), 1.76 (2H, m), 1.28 (3H, t, J=7 Hz), 1.15 (1H, m), 0.57 (2H, m), 0.29 (2H, m);

MS (ESI) m/z: 487 [M+H]$^+$.

Example 111 cyclopentyl 4-({6-[5-(ethylsulfonyl)indolin-1-yl]pyrimidin-4-yl}oxy)piperidine-1-carboxylate (exemplary compound No: 312)

The same reaction as in the method described in Example 49 was performed using the 5-(ethylsulfonyl)-1-(6-{[1-(1H-imidazol-1-ylcarbonyl)piperidin-4-yl]oxy}pyrimidin-4-yl)indoline (130 mg, 0.269 mmol) produced in Reference Example 31 to obtain the title compound as white powder (85.6 mg, yield: 64%).

$^1$H-NMR (400 MHz, CDCl$_3$) δ ppm: 8.57 (1H, d, J=9 Hz), 8.50 (1H, s), 7.74 (1H, dd, J=9 Hz, 2 Hz), 7.67 (1H, s), 5.98 (1H, s), 5.33 (1H, m), 5.12 (1H, m), 4.06 (2H, t, J=9 Hz), 3.81 (2H, m), 3.37-3.27 (4H, m), 3.10 (2H, q, J=7 Hz), 2.01 (2H, m), 1.86 (2H, m), 1.79-1.66 (6H, m), 1.60 (2H, m), 1.27 (3H, t, J=7 Hz);

MS (ESI) m/z: 501 [M+H]$^+$.

Example 112 benzyl rac-cis-2-methyl-4-({6-[5-(methylsulfonyl)indolin-1-yl]pyrimidin-4-yl}oxy)piperidine-1-carboxylate (exemplary compound No: 299)

Sodium hydride (63%) (49 mg, 1.23 mmol) was added to a THF (10 mL) solution of benzyl rac-cis-4-hydroxy-2-methylpiperidine-1-carboxylate (compound described in the document J. Chem. Soc., Perkin Trans. 1, 1998, vol. 20, p. 3365; 152 mg, 0.610 mmol), and the mixture was stirred at room temperature for 30 minutes. To the reaction solution, the 1-(6-chloropyrimidin-4-yl)-5-(methylsulfonyl)indoline (227 mg, 0.733 mmol) produced in Reference Example 19 was added, and the mixture was stirred for 10.5 hours. To the reaction solution, a saturated aqueous solution of ammonium chloride was added, followed by extraction with ethyl acetate three times. The obtained organic layer was dried over anhydrous sodium sulfate, and the solvent was distilled off under reduced pressure. The obtained residue was purified by silica gel column chromatography (hexane:ethyl acetate=7:3-3:2, V/V) to obtain the title compound as white powder (271 mg, yield: 85%).

$^1$H-NMR (400 MHz, CDCl$_3$) δ ppm: 8.58 (1H, d, J=9 Hz), 8.51 (1H, s), 7.78 (1H, dd, J=9 Hz, 2 Hz), 7.71 (1H, m), 7.39-7.27 (5H, m), 5.96 (1H, s), 5.50 (1H, m), 5.15 (2H, d, J=2 Hz), 4.49 (1H, m), 4.13-3.99 (3H, m), 3.39-3.25 (3H, m), 3.03 (3H, s), 2.05-1.95 (2H, m), 1.87-1.76 (2H, m) 1.33 (3H, d, J=7 Hz);

MS (ESI) m/z: 523 [M+H]$^+$.

Example 113 isopropyl rac-cis-2-methyl-4-({6-[5-(methylsulfonyl)indolin-1-yl]pyrimidin-4-yl}oxy)piperidine-1-carboxylate (exemplary compound No: 295)

Palladium hydroxide (300 mg) was added to a methanol (5 mL)/ethyl acetate (5 mL) mixed solution of the benzyl rac-cis-2-methyl-4-({6-[5-(methylsulfonyl)indolin-1-yl]pyrimidin-4-yl}oxy)piperidine-1-carboxylate (271 mg, 0.519 mmol) produced in Example 112, and the mixture was stirred for 2 hours in a hydrogen atmosphere. The reaction solution was filtered through Celite (trade name), and the solvent was distilled off under reduced pressure. To a dichloromethane (10 mL) solution of the obtained residue, diisopropylethylamine (447 μL, 2.63 mmol) and isopropyl chloroformate (218 μL, 1.56 mmol) were added at 0° C., and the mixture was stirred for 30 minutes with heating to room temperature. To the reaction solution, a saturated aqueous solution of ammonium chloride was added, followed by extraction with ethyl acetate three times. The obtained organic layer was dried over anhydrous sodium sulfate, and the solvent was distilled off under reduced pressure. The obtained residue was purified by silica gel column chromatography (hexane:ethyl acetate=7:3-3:2, V/V) to obtain the title compound as white powder (39.8 mg, yield: 16%).

$^1$H-NMR (400 MHz, CDCl$_3$) δ ppm: 8.59 (1H, d, J=9 Hz), 8.52 (1H, s), 7.79 (1H, dd, J=9 Hz, 2 Hz), 7.73 (1H, m), 5.97 (1H, s), 5.50 (1H, m), 4.95 (1H, m), 4.43 (1H, m), 4.09 (2H, t, J=9 Hz), 3.99 (1H, m), 3.35-3.24 (3H, m), 3.04 (3H, s), 2.02-1.94 (3H, m), 1.87-1.76 (1H, m), 1.30 (3H, d, J=7 Hz), 1.26 (6H, dd, J=6 Hz, 1 Hz);

MS (ESI) m/z: 475 [M+H]$^+$.

Example 114 allyl 4-({6-[5-(methylsulfonyl)indolin-1-yl]pyrimidin-4-yl}oxy)piperidine-1-carboxylate (exemplary compound No: 31)

The same reaction as in the method described in Example 6 was performed using the 5-(methylsulfonyl)-1-[6-(piperidin-4-yloxy)pyrimidin-4-yl]indoline (518 mg, 1.39 mmol) produced in Reference Example 28 and, instead of butyl chloroformate, allyl chloroformate (220 μL, 2.08 mmol) to obtain the title compound as white powder (522 mg, yield: 82%).

$^1$H-NMR (400 MHz, CDCl$_3$) δ ppm: 8.57 (1H, d, J=9 Hz), 8.50 (1H, d, J=1 Hz), 7.77 (1H, dd, J=9 Hz, 2 Hz), 7.71 (1H, s), 5.99 (1H, s), 5.96 (1H, m), 5.34 (1H, m), 5.32 (1H, m), 5.22 (1H, m), 4.62 (2H, m), 4.06 (2H, t, J=9 Hz), 3.85 (2H, m), 3.39 (2H, ddd, J=13 Hz, 9 Hz, 4 Hz), 3.31 (2H, t, J=9 Hz), 3.04 (3H, s), 2.02 (2H, m), 1.77 (2H, m);

MS (ESI) m/z: 459 [M+H]$^+$.

Example 115 prop-2-yn-1-yl 4-({6-[5-(methylsulfonyl)indolin-1-yl]pyrimidin-4-yl}oxy)piperidine-1-carboxylate (exemplary compound No: 33)

The same reaction as in the method described in Example 6 was performed using the 5-(methylsulfonyl)-1-[6-(piperidin-4-yloxy)pyrimidin-4-yl]indoline (408 mg, 1.09 mmol) produced in Reference Example 28 and, instead of butyl chloroformate, propargyl chloroformate (159 μL, 1.63 mmol) to obtain the title compound as pale yellow powder (338 mg, yield: 68%).

$^1$H-NMR (400 MHz, CDCl$_3$) δ ppm: 8.58 (1H, d, J=9 Hz), 8.51 (1H, s), 7.79 (1H, dd, J=9 Hz, 2 Hz), 7.72 (1H, d, J=1 Hz), 5.99 (1H, s), 5.96 (1H, m), 5.35 (1H, m), 4.73 (1H, d, J=2 Hz), 4.07 (2H, t, J=9 Hz), 3.83 (2H, m), 3.42 (2H, ddd, J=13 Hz, 9 Hz, 4 Hz), 3.31 (2H, t, J=9 Hz), 3.04 (3H, s), 2.48 (1H, t, J=2 Hz), 2.02 (2H, m), 1.78 (2H, m);
MS (ESI) m/z: 457 [M+H]$^+$.

Example 116

2,2,2-trifluoroethyl 4-({6-[5-(methylsulfinyl)indolin-1-yl]pyrimidin-4-yl}oxy)piperidine-1-carboxylate (exemplary compound No: 626)

The same reaction as in the method described in Reference Example 32 was performed using the tert-butyl 4-({6-[5-(methylsulfinyl)indolin-1-yl]pyrimidin-4-yl}oxy)piperidine-1-carboxylate (604 mg, 1.32 mmol) produced in Example 80 to obtain a yellow oil compound (511 mg). The same reaction as in the method described in Example 61 was performed using a portion (293 mg) of the obtained oil compound to obtain the title compound as white powder (103 mg, yield: 28%).

$^1$H-NMR (400 MHz, CDCl$_3$) δ ppm: 8.53 (1H, d, J=9 Hz), 8.49 (1H, s), 7.57 (1H, s), 7.43 (1H, d, J=9 Hz), 5.96 (1H, s), 5.39-5.34 (1H, m), 4.54-4.47 (2H, m), 4.04 (2H, t, J=9 Hz), 3.85-3.79 (2H, m), 3.48-3.42 (2H, m), 3.31 (2H, t, J=9 Hz), 2.71 (3H, s), 2.06-1.99 (2H, m), 1.85-1.75 (2H, m);
MS (ESI) m/z: 485 [M+H]$^+$.

Example 117 isopropyl cis-3-fluoro-4-[6-(5-methanesulfonyl-2,3-dihydro-indol-1-yl)-pyrimidin-4-yloxy]-piperidine-1-carboxylate (exemplary compound No: 665)

(117a) tert-butyl cis-3-fluoro-4-[6-(5-methanesulfonyl-2,3-dihydro-indol-1-yl)-pyrimidin-4-yloxy]-piperidine-1-carboxylate Sodium hydride (109 mg, 2.87 mmol) was added to a THF (12 mL) solution of tert-butyl cis-3-fluoro-4-hydroxy-piperidine-1-carboxylate (315 mg, 1.43 mmol) and the 1-(6-chloropyrimidin-4-yl)-5-(methylsulfonyl)indoline (296 mg, 0.956 mmol) produced in Reference Example 19, and the mixture was heated to reflux for 2.5 hours in a nitrogen atmosphere. To the reaction solution, a saturated aqueous solution of ammonium chloride was added, followed by extraction with ethyl acetate three times. The obtained organic layer was washed with saturated saline and dried over anhydrous magnesium sulfate, and the solvent was distilled off under reduced pressure. The obtained residue was washed with diethyl ether and ethyl acetate to obtain the title compound as yellow powder (326.8 mg, yield: 70%).

(117b) isopropyl cis-3-fluoro-4-[6-(5-methanesulfonyl-2,3-dihydro-indol-1-yl)-pyrimidin-4-yloxy]-piperidine-1-carboxylate A 4 N hydrochloric acid-acetic acid solution (10 ml) was added to the compound (311 mg, 0.632 mmol) produced in paragraph (117a), and the mixture was stirred at room temperature for 45 minutes. The deposited solid was collected by filtration and washed with ethyl acetate to obtain a compound (364.9 mg). To a dichloromethane (2 mL) suspension of the obtained compound (130 mg), N,N-diisopropylethylamine (108 μL, 1.13 mmol) and isopropyl chloroformate (38 μL, 0.338 mmol) were added, and the mixture was stirred at room temperature. To the reaction solution, a saturated aqueous solution of ammonium chloride was added, followed by extraction with ethyl acetate three times. The obtained organic layer was washed with saturated saline and dried over anhydrous magnesium sulfate, and the solvent was distilled off under reduced pressure. The obtained residue was purified by silica gel column chromatography (hexane:ethyl acetate=1:2-2:1, V/V). The obtained crude product was washed with methanol to obtain the title compound as white powder (85.7 mg, yield: 80%).

$^1$H-NMR (400 MHz, CDCl$_3$) δ ppm: 8.59 (1H, d, J=8.6 Hz), 8.50 (1H, s), 7.79 (1H, d, J=8.6 Hz), 7.73 (1H, s), 6.08 (1H, s), 5.45-5.34 (1H, m), 4.95 (1H, qu, J=5.9 Hz), 4.91 (1H, d, J=47.7 Hz), 4.33 (1H, brs), 4.18-4.07 (1H, m), 4.07 (2H, t, J=8.8 Hz), 3.37-3.26 (1H, m), 3.32 (2H, t, J=8.8 Hz), 3.15 (1H, brs), 3.05 (3H, s), 2.17-2.06 (1H, m), 1.96-1.88 (1H, m), 1.27 (6H, d, J=5.9 Hz).

Example 118 cyclopropylmethyl 4-({6-[5-(methylsulfinyl)indolin-1-yl]pyrimidin-4-yl}oxy)piperidine-1-carboxylate (exemplary compound No: 620)

The same reaction as in the method described in Reference Example 32 was performed using the tert-butyl 4-({6-[5-(methylsulfinyl)indolin-1-yl]pyrimidin-4-yl}oxy)piperidine-1-carboxylate (604 mg, 1.32 mmol) produced in Example 80 to obtain a yellow foam compound (511 mg). The same reaction as in the method described in Example 44 was performed using a portion (214 mg) of the obtained oil compound to obtain the title compound as white powder (19.3 mg, yield: 8%).

$^1$H-NMR (500 MHz, CDCl$_3$) δ ppm: 8.53 (1H, d, J=9 Hz), 8.49 (1H, s), 7.57 (1H, s), 7.43 (1H, d, J=8 Hz), 5.95 (1H, s), 5.36-5.31 (1H, m), 4.04 (2H, t, J=9 Hz), 3.93 (2H, d, J=7 Hz), 3.88-3.83 (2H, m), 3.39-3.34 (2H, m), 3.31 (2H, t, J=9 Hz), 2.71 (3H, s), 2.04-1.99 (2H, m), 1.79-1.73 (2H, m), 1.17-1.11 (1H, m), 0.57-0.54 (2H, m), 0.30-0.27 (2H, m);
MS (ESI) m/z: 457 [M+H]$^+$.

Example 119 isopropyl 4-({5-methoxy-6-[5-(methylsulfinyl)indolin-1-yl]pyrimidin-4-yl}oxy)piperidine-1-carboxylate (exemplary compound No: 637)

(119a) tert-butyl 4-({5-methoxy-6-[5-(methylsulfinyl)indolin-1-yl]pyrimidin-4-yl}oxy)piperidine-1-carboxylate The same reaction as in the method described in Example 56 was performed using 5-methylsulfinylindoline (276 mg, 1.52 mmol) and, instead of tert-butyl 4-[(6-chloropyrimidin-4-yl)oxy]piperidine-1-carboxylate, the tert-butyl 4-[(6-chloro-5-methoxypyrimidin-4-yl)oxy]piperidine-1-carboxylate (576 mg, 1.68 mmol) produced in Reference Example 43 to obtain a yellow oil compound.

To a dichloromethane (7.5 mL) solution of the obtained oil compound, acetyl chloride (125 µL, 1.76 mmol) and diisopropylethylamine (630 µL, 3.53 mmol) were added at 0° C., and the mixture was stirred at room temperature for 2.5 hours. To the reaction solution, water was added, followed by extraction with ethyl acetate three times. The obtained organic layer was washed with water and saturated saline and dried over anhydrous magnesium sulfate, and the solvent was distilled off under reduced pressure. The obtained residue was purified by silica gel column chromatography [(i) ethyl acetate; (ii) ethyl acetate:methanol=98:2-96:4-93:7-90:10, v/v]. The same reaction as in the method described in Example 61 was performed using a portion (293 mg) of the obtained compound to obtain the title compound as yellow oil (283 mg, yield: 38%).

$^1$H-NMR (400 MHz, CDCl$_3$) δ ppm: 8.21 (1H, s), 7.77 (1H, d, J=9 Hz), 7.55 (1H, s), 7.39 (1H, J=9 Hz), 5.39-5.33 (1H, m), 4.32 (2H, t, J=9 Hz), 3.81-3.74 (2H, m), 3.76 (3H, s), 3.39-3.32 (2H, m), 3.23 (2H, t, J=9 Hz), 2.71 (3H, s), 2.07-2.02 (2H, m), 1.87-1.79 (2H, m), 1.48 (9H, s);

MS (ESI) m/z: 489 [M+H]$^+$.

(119b) isopropyl 4-({5-methoxy-6-[5-(methylsulfinyl)indolin-1-yl]pyrimidin-4-yl}oxy)piperidine-1-carboxylate The same reaction as in the method described in Example 28 was performed using the tert-butyl 4-({5-methoxy-6-[5-(methylsulfinyl)indolin-1-yl]pyrimidin-4-yl}oxy)piperidine-1-carboxylate (108 mg, 0.221 mmol) produced in paragraph (119a) to obtain the title compound as white powder (80.1 mg, yield: 76%).

$^1$H-NMR (400 MHz, CDCl$_3$) δ ppm: 8.21 (1H, s), 7.77 (1H, d, J=9 Hz), 7.55 (1H, s), 7.39 (1H, d, J=9 Hz), 5.40-5.35 (1H, m), 4.94 (1H, sept, J=6 Hz), 4.32 (2H, t, J=9 Hz), 3.86-3.80 (2H, m), 3.76 (3H, s), 3.43-3.36 (2H, m), 3.24 (2H, t, J=9 Hz), 2.71 (3H, s), 2.08-2.02 (2H, m), 1.88-1.80 (2H, m), 1.27 (6H, d, J=6 Hz);

MS (ESI) m/z: 475 [M+H]$^+$.

Preparation Example 5 g of the compound obtained in each Example, 90 g of lactose, 34 g of corn starch, 20 g of crystalline cellulose, and 1 g of magnesium stearate are mixed using a blender and then compressed using a tableting machine to obtain tablets.

Test Example 1

Oral Glucose Tolerance Test (oGTT) Using Mice 2.0 to 8.0 mg of a test compound was weighed and then placed in an agate mortar. While the compound was pulverized, a 0.5% methylcellulose solution was added thereto to prepare a 1 mg/ml suspension. Mice C57/BL6J (6- to 8-week-old male) were purchased from Charles River Laboratories Japan Inc. and raised in a cage until they became 9- to 13-week-old. The mice were fasted after 5 to 6 p.m. of the day before the test. On the test day, blood was collected from the tail vein, and the preceding prepared suspension was orally administered to each of the mice. Thirty minutes after administration, blood was further collected from the tail vein (plasma glucose level in this blood was used as a pre-value), and a 20 to 30% glucose solution was then orally administered thereto at a dose of 10 ml/kg for glucose load. After the glucose load, blood was further collected from the tail vein at time points 15, 30, 60, and 120 minutes. The collected blood was centrifuged to separate plasma. The pre-value and plasma glucose levels at 15, 30, 60, and 120 minutes after the glucose load were measured using Glucoroder GXT (Shino-Test Corp.), and the rate of decrease in blood glucose AUC (%) from a vehicle-administered group was calculated. To this vehicle-administered group, a 0.5% methylcellulose solution was administered instead of the suspension of the compound.

TABLE 2

| Compound | Rate of decrease in AUC (%) |
|---|---|
| Example 1 | 28 |
| Example 2 | 22 |
| Example 22 | 21 |
| Example 31 | 20 |
| Example 44 | 18 |
| Example 60 | 22 |
| Example 80 | 19 |
| Example 83 | 20 |
| Example 85 | 27 |
| Example 92 | 16 |
| Example 93 | 15 |
| Example 104 | 10 |
| Example 116 | 17 |
| Example 117 | 27 |
| Example 118 | 16 |

Test Example 2

Test on Measurement of Compound Concentration in Rat Blood 20 to 50 mg of a test compound is weighed and then placed in an agate mortar. While the compound is pulverized, a 0.5% methylcellulose solution is added thereto to prepare a 2.5 mg/ml suspension. F344 rats (5- to 7-week-old male) are purchased from Charles River Laboratories Japan Inc. and fasted after 5 to 6 p.m. of the day before the test. On the test day, the body weights of the rats are measured, and the test compound is then orally administered at a dose of 10 ml/kg to each of the rats. Blood is collected from the tail vein at time points 0.5, 1, 2, 4, 6, and 24 hours after administration. The collected blood is centrifuged to separate plasma. The plasma is deproteinized and then applied to liquid chromatography/mass spectrometry apparatuses to calculate the compound concentration in the plasma.

Test Example 3

Oral Glucose Tolerance Test (oGTT) Using Rats 200 mg of a test compound is weighed and then placed in an agate mortar. While the compound is pulverized, a 0.5% methylcellulose solution is added thereto to prepare a 7.5 mg/ml suspension. When different doses of suspensions are prepared, the preceding prepared suspension is sequentially diluted with a 0.5% methylcellulose solution to prepare the suspensions of interest. Zucker fatty rats and Zucker Diabetic Fatty rats (8- to 12-week-old male) are purchased from Charles River Laboratories Japan Inc. Before the test, basic blood glucose levels and body weights are adjusted to be equal in level between administered groups. The rats are fasted after 3 to 6 p.m. of the day before the test. On the test day, blood is collected from the tail vein, and the preceding prepared suspension is then orally administered to each of the rats. Thirty minutes after administration, blood is further collected from the tail vein (plasma glucose level in this blood is used as a pre-value), and a 20% glucose solution is then orally administered thereto at a dose of 4 ml/kg for glucose load. After the glucose load, blood is further collected from the tail vein at time points 30 minutes, 1, 2, and 4 hours. The collected blood is centrifuged to separate plasma. The pre-value and plasma glucose levels at 30 minutes, 1, 2, and 4 hours after the glucose load are measured using Glucoroder GXT (Shino-Test Corp.), and the rate of decrease in blood glucose AUC (%) from a vehicle-administered group is calculated. To this vehicle-administered group, a 0.5% methylcellulose solution is administered instead of the suspension of the compound.

Industrial Applicability

A compound of the present invention or a pharmaceutically acceptable salt thereof is useful as an active ingredient in a pharmaceutical composition for treating and/or preventing, for example, type 1 diabetes mellitus, type 2 diabetes mellitus, pregnancy diabetes, hyperglycemia caused by other factors, impaired glucose tolerance (IGT), diabetes-related disease, or complications from diabetes.

The invention claimed is:
1. A compound represented by the general formula (I) or a pharmaceutically acceptable salt thereof:

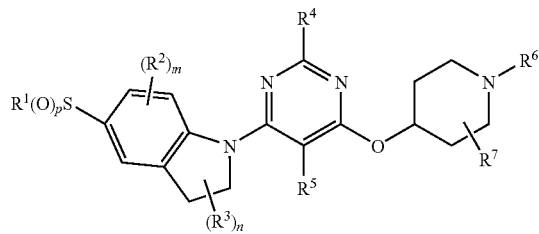

(I)

wherein
p is 1 or 2;
$R^1$ is a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an amino group, or a mono- or di(C1-C6 alkyl)amino group;
substituent group α is the group consisting of a halogen atom, a hydroxyl group, a C1-C6 alkoxy group, a C3-C7 cycloalkyl group which may have 1 to 3 substituents selected from substituent group β, an amino group, a mono- or di(C1-C6 alkyl)amino group, an aryl group which may have 1 to 3 substituents selected from substituent group β, and a heteroaryl group which may have 1 to 3 substituents selected from substituent group β;
substituent group β is the group consisting of a halogen atom, a hydroxyl group, a C1-C6 alkyl group, and a C1-C6 alkoxy group;
m is an integer of 0 to 3;
each $R^2$ may be the same or different and is a halogen atom, a C1-C6 alkyl group, a C1-C6 alkoxy group, or a C1-C6 alkoxy-C1-C6 alkyl group;
n is an integer of 0 to 4;
each $R^3$ may be the same or different and is a halogen atom, a C1-C6 alkyl group, a C1-C6 alkoxy group, or a C1-C6 alkoxy-C1-C6 alkyl group;
$R^4$ and $R^5$ are each independently a hydrogen atom, a halogen atom, a C1-C6 alkyl group, a C1-C6 alkoxy group, or a C1-C6 alkoxy-C1-C6 alkyl group;
$R^6$ is —C(O)O—$R^{6a}$, —C(O)—$R^{6b}$, or —S(O)$_2$—$R^{6c}$;
$R^{6a}$ is a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an aryl group which may have 1 to 3 substituents selected from substituent group β, or a heteroaryl group which may have 1 to 3 substituents selected from substituent group β;
$R^{6b}$ is a hydrogen atom, a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an amino group, a mono- or di(C1-C6 alkyl)amino group, an aryl group which may have 1 to 3 substituents selected from substituent group β, or a heteroaryl group which may have 1 to 3 substituents selected from substituent group β;
$R^{6c}$ is a C1-C6 alkyl group; and
$R^7$ is a hydrogen atom, a halogen atom, or a C1-C6 alkyl group.

2. The compound according to claim 1, wherein $R^1$ is a C1-C6 alkyl group which may have 1 to 3 substituents selected from substituent group α, a C3-C7 cycloalkyl group which may have 1 to 3 substituents selected from substituent group β, an amino group, or a mono- or di(C1-C6 alkyl)amino group.

3. The compound according to claim 1, wherein $R^1$ is a C1-C6 alkyl group which may have 1 to 3 substituents selected from substituent group α or a C3-C7 cycloalkyl which may have 1 to 3 substituents selected from substituent group β.

4. The compound according to claim 1, wherein m is 0.

5. The compound according to claim 1, wherein m is 1, and $R^2$ is a halogen atom.

6. The compound according to claim 1, wherein n is 0.

7. The compound according to claim 1, wherein n is 1, and $R^3$ is a halogen atom.

8. The compound according to claim 1, wherein $R^4$ is a hydrogen atom.

9. The compound according to claim 1, wherein $R^5$ is a hydrogen atom, a C1-C6 alkyl group, or a C1-C6 alkoxy group.

10. The compound according to claim 1, wherein $R^5$ is a hydrogen atom or a C1-C6 alkoxy group.

11. The compound according to claim 1, wherein $R^6$ is —C(O)O—$R^{6a}$.

12. The compound according to claim 1, wherein $R^{6a}$ is a C1-C6 alkyl group which may have 1 to 3 substituents selected from substituent group α, a C3-C7 cycloalkyl group which may have 1 to 3 substituents selected from substituent group β, an aryl group which may have 1 to 3 substituents selected from substituent group β, or a heteroaryl group which may have 1 to 3 substituents selected from substituent group β.

13. The compound according to claim 1, wherein $R^6$ is —C(O)—$R^{6b}$.

14. The compound according to claim 1, wherein $R^{6b}$ is a C1-C6 alkyl group which may have 1 to 3 substituents selected from substituent group α or an aryl group which may have 1 to 3 substituents selected from substituent group β.

15. The compound according to claim 1, wherein $R^{6b}$ is a C1-C6 alkyl group which may have 1 to 3 substituents selected from substituent group α.

16. The compound according to claim 1, wherein $R^6$ is —S(O)$_2$—$R^{6c}$.

17. The compound according to claim 1, wherein $R^{6c}$ is a C1-C4 alkyl group.

18. The compound according to claim 1, wherein $R^7$ is a hydrogen atom, a fluorine atom, or a C1-C3 alkyl group.

19. A compound represented by the general formula (II) or a pharmaceutically acceptable salt thereof:

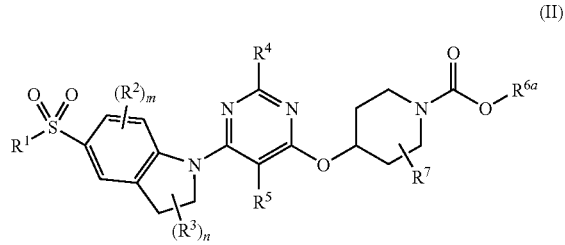

(II)

wherein $R^1$ is a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an amino group, or a mono- or di(C1-C6 alkyl)amino group;

substituent group α is the group consisting of a halogen atom, a hydroxyl group, a C1-C6 alkoxy group, a C3-C7 cycloalkyl group which may have 1 to 3 substituents selected from substituent group β, an amino group, a mono- or di(C1-C6 alkyl)amino group, an aryl group which may have 1 to 3 substituents selected from substituent group β, and a heteroaryl group which may have 1 to 3 substituents selected from substituent group β;

substituent group β is the group consisting of a halogen atom, a hydroxyl group, a C1-C6 alkyl group, and a C1-C6 alkoxy group;

m is an integer of 0 to 3;

each $R^2$ may be the same or different and is a halogen atom, a C1-C6 alkyl group, a C1-C6 alkoxy group, or a C1-C6 alkoxy-C1-C6 alkyl group;

n is an integer of 0 to 4;

each $R^3$ may be the same or different and is a halogen atom, a C1-C6 alkyl group, a C1-C6 alkoxy group, or a C1-C6 alkoxy-C1-C6 alkyl group;

$R^4$ and $R^5$ are each independently a hydrogen atom, a halogen atom, a C1-C6 alkyl group, a C1-C6 alkoxy group, or a C1-C6 alkoxy-C1-C6 alkyl group;

$R^{6a}$ is a C1-C6 alkyl group which may have 1 to 3 substituents selected from substituent group α, a C3-C7 cycloalkyl group which may have 1 to 3 substituents selected from substituent group β, a C2-C6 alkynyl group which may have 1 to 3 substituents selected from substituent group β, a C2-C6 alkenyl group which may have 1 to 3 substituents selected from substituent group β, an aryl group which may have 1 to 3 substituents selected from substituent group β, or a heteroaryl group which may have 1 to 3 substituents selected from substituent group β; and $R^7$ is a hydrogen atom, a halogen atom, or a C1-C6 alkyl group.

20. A compound selected from the group consisting of the following:

isopropyl 4-({6-[5-(methylsulfonyl)indolin-1-yl]pyrimidin-4-yl}oxy)piperidine-1-carboxylate;
isobutyl 4-({6-[5-(methylsulfonyl)indolin-1-yl]pyrimidin-4-yl}oxy)piperidine-1-carboxylate;
tert-butyl 4-({6-[5-(methylsulfonyl)indolin-1-yl]pyrimidin-4-yl}oxy)piperidine-1-carboxylate;
cyclobutyl 4-({6-[5-(methylsulfonyl)indolin-1-yl]pyrimidin-4-yl}oxy)piperidine-1-carboxylate;
cyclopentyl 4-({6-[5-(methylsulfonyl)indolin-1-yl]pyrimidin-4-yl}oxy)piperidine-1-carboxylate;
1-ethylpropyl 4-({6-[5-(methylsulfonyl)indolin-1-yl]pyrimidin-4-yl}oxy)piperidine-1-carboxylate;
cyclopropylmethyl 4-({6-[5-(methylsulfonyl)indolin-1-yl]pyrimidin-4-yl}oxy)piperidine-1-carboxylate;
3-furylmethyl 4-({6-[5-(methylsulfonyl)indolin-1-yl]pyrimidin-4-yl}oxy)piperidine-1-carboxylate;
1-cyclopropylethyl 4-({6-[5-(methylsulfonyl)indolin-1-yl]pyrimidin-4-yl}oxy)piperidine-1-carboxylate;
2-fluoroethyl 4-({6-[5-(methylsulfonyl)indolin-1-yl]pyrimidin-4-yl}oxy)piperidine-1-carboxylate;
2,2-difluoroethyl 4-({6-[5-(methylsulfonyl)indolin-1-yl]pyrimidin-4-yl}oxy)piperidine-1-carboxylate;
2,2,2-trifluoroethyl 4-({6-[5-(methylsulfonyl)indolin-1-yl]pyrimidin-4-yl}oxy)piperidine-1-carboxylate;
1-(6-{[1-(3-methylbutanoyl)piperidin-4-yl]oxy}pyrimidin-4-yl)-5-(methylsulfonyl)indoline;
isopropyl 4-({5-methoxy-6-[5-(methylsulfonyl)indolin-1-yl]pyrimidin-4-yl}oxy)piperidine-1-carboxylate;
tert-butyl 4-({5-methoxy-6-[5-(methylsulfonyl)indolin-1-yl]pyrimidin-4-yl}oxy)piperidine-1-carboxylate;
isopropyl 4-({6-[5-(ethylsulfonyl)indolin-1-yl]pyrimidin-4-yl}oxy)piperidine-1-carboxylate;
isobutyl 4-({6-[5-(ethylsulfonyl)indolin-1-yl]pyrimidin-4-yl}oxy)piperidine-1-carboxylate;
sec-butyl 4-({6-[5-(ethylsulfonyl)indolin-1-yl]pyrimidin-4-yl}oxy)piperidine-1-carboxylate;
cyclobutyl 4-({6-[5-(ethylsulfonyl)indolin-1-yl]pyrimidin-4-yl}oxy)piperidine-1-carboxylate;
cyclopropylmethyl 4-({6-[5-(ethylsulfonyl)indolin-1-yl]pyrimidin-4-yl}oxy)piperidine-1-carboxylate;
2,2-difluoroethyl 4-({6-[5-(ethylsulfonyl)indolin-1-yl]pyrimidin-4-yl}oxy)piperidine-1-carboxylate;
2,2,2-trifluoroethyl 4-({6-[5-(ethylsulfonyl)indolin-1-yl]pyrimidin-4-yl}oxy)piperidine-1-carboxylate;
tert-butyl 4-[(6-{5-[(2-fluoroethyl)sulfonyl]indolin-1-yl}pyrimidin-4-yl)oxy]piperidine-1-carboxylate;
tert-butyl 4-({6-[5-(propylsulfonyl)indolin-1-yl]pyrimidin-4-yl}oxy)piperidine-1-carboxylate;
2,2,2-trifluoroethyl 4-({6-[5-(propylsulfonyl)indolin-1-yl]pyrimidin-4-yl}oxy)piperidine-1-carboxylate;
tert-butyl 4-({6-[5-(cyclobutylsulfonyl)indolin-1-yl]pyrimidin-4-yl}oxy)piperidine-1-carboxylate;
tert-butyl 4-({6-[5-(methylsulfinyl)indolin-1-yl]pyrimidin-4-yl}oxy)piperidine-1-carboxylate;

2,2,2-trifluoroethyl 4-({6-[5-(methylsulfinyl)indolin-1-yl]pyrimidin-4-yl}oxy)piperidine-1-carboxylate;

isopropyl cis-3-fluoro-4-[6-(5-methanesulfonyl-2,3-dihydro-indol-1-yl)-pyrimidin-4-yloxy]-piperidine-1-carboxylate;

cyclopropylmethyl 4-({6-[5-(methylsulfinyl)indolin-1-yl]pyrimidin-4-yl}oxy)piperidine-1-carboxylate; and isopropyl 4-({5-methoxy-6-[5-(methylsulfinyl)indolin-1-yl]pyrimidin-4-yl}oxy)piperidine-1-carboxylate.

21. A pharmaceutical composition comprising a compound according to claim 1 or a pharmaceutically acceptable salt thereof as an active ingredient.

22. A pharmaceutical composition comprising a compound according to claim 19 or a pharmaceutically acceptable salt thereof as an active ingredient.

23. A pharmaceutical composition comprising a compound according to claim 20 or a pharmaceutically acceptable salt thereof as an active ingredient.

24. A method for treating type 1 diabetes mellitus or type 2 diabetes mellitus, comprising administering a pharmacologically effective amount of a compound according to claim 1 to a human.

* * * * *